(12) United States Patent
Li et al.

(10) Patent No.: US 7,834,178 B2
(45) Date of Patent: Nov. 16, 2010

(54) TRIAZINE 11-BETA HYDROXYSTEROID DEHYDROGENASE TYPE 1 INHIBITORS

(75) Inventors: Jun Li, Princeton, NJ (US); Jeffrey A. Robl, Newtown, PA (US); Lawrence J. Kennedy, Titusville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 304 days.

(21) Appl. No.: 11/679,898

(22) Filed: Feb. 28, 2007

(65) Prior Publication Data

US 2007/0207985 A1    Sep. 6, 2007

Related U.S. Application Data

(60) Provisional application No. 60/778,159, filed on Mar. 1, 2006.

(51) Int. Cl.
  C07D 253/065    (2006.01)
  C07D 253/08     (2006.01)
  C07D 253/10     (2006.01)
  A61K 31/53      (2006.01)
  A61P 3/06       (2006.01)
  A61P 3/10       (2006.01)
  A61P 9/02       (2006.01)

(52) U.S. Cl. .................. 544/182; 544/183; 544/184; 514/242; 514/243

(58) Field of Classification Search .......... 544/182, 544/183, 184; 514/242, 243
See application file for complete search history.

(56) References Cited

U.S. PATENT DOCUMENTS

| | | | | |
|---|---|---|---|---|
| 3,836,531 A * | 9/1974 | Yano et al. | ............... | 544/192 |
| 3,910,909 A * | 10/1975 | Draber et al. | ............ | 544/182 |
| 4,239,760 A * | 12/1980 | Sasse et al. | ............. | 514/243 |
| 5,069,708 A * | 12/1991 | Meyer et al. | ............. | 504/228 |
| 5,491,126 A * | 2/1996 | Selby | .................... | 504/228 |
| 5,616,584 A * | 4/1997 | Lee et al. | ............... | 514/243 |
| 5,633,218 A * | 5/1997 | Spedding et al. | ........ | 504/228 |
| 5,670,502 A * | 9/1997 | Brown | .................. | 514/243 |
| 6,153,610 A * | 11/2000 | Brown et al. | ............ | 514/243 |
| 6,610,677 B2 * | 8/2003 | Davies et al. | ........... | 514/183 |
| 6,673,795 B2 * | 1/2004 | Binggeli et al. | ......... | 514/242 |
| 7,241,763 B2 * | 7/2007 | LaCrampe et al. | ...... | 514/243 |
| 7,501,415 B2 * | 3/2009 | Aronov et al. | .......... | 514/241 |
| 2002/0165218 A1 | 11/2002 | Halbrook et al. | | |
| 2003/0060466 A1 * | 3/2003 | Binggeli et al. | ......... | 514/242 |
| 2003/0225073 A1 * | 12/2003 | Bebbington et al. | ... | 514/227.8 |
| 2004/0009974 A1 * | 1/2004 | Bebbington et al. | ... | 514/227.8 |
| 2004/0106615 A1 * | 6/2004 | Cochran et al. | ......... | 514/242 |
| 2004/0147507 A1 * | 7/2004 | Ledeboer et al. | ....... | 514/217.04 |
| 2005/0234059 A1 * | 10/2005 | Hale et al. | ............... | 514/242 |
| 2007/0078128 A1 * | 4/2007 | Saito et al. | ............. | 514/229.2 |
| 2007/0078135 A1 | 4/2007 | Yuan et al. | | |
| 2008/0004257 A1 * | 1/2008 | Chan et al. | ............... | 514/218 |

FOREIGN PATENT DOCUMENTS

| | | |
|---|---|---|
| EP | 0186868 | 12/1985 |
| EP | 0198286 | 3/1986 |
| EP | 0469773 | 7/1991 |
| JP | 05051369 | * 3/1993 |
| WO | WO-00/66568 | * 11/2000 |
| WO | WO 02/20500 | 3/2002 |
| WO | WO 03/104207 | 12/2003 |
| WO | WO 2007/003521 | 1/2007 |
| WO | WO 2007/038452 | 4/2007 |
| WO | WO 2007/047625 | 4/2007 |

OTHER PUBLICATIONS

Wolft Manfred. E. "Burger's Medicinal Chemistry, 5ed, Part 1", John Wiley & Sons, 1995, pp. 975-977.*
Banker, G.S. et al, "Modern Pharmaceutics, 3ed.", Marcel Dekker, New York. 1996, pp. 451 and 596.*
West, Anthony R., Solid State Chemistry and its Applications, Wiley, New York, 1988, pp. 358 & 365.*
Vippagunta et al., Advanced Drug Delivery Reviews 48: Mar. 26, 2001.*
Cecil Textbook of Medicine, edited by Bennet, J.C., and Plum F., 20th edition, vol. 1, 1004-1010, 1996.*
Konno et al., J. Agric. Food Chem. 43, 838-842, 1995.*
O'Rourke et al., Journal of Medicinal Chemistry 20(5), 723-726, 1977.*
Taylor et al., Journal of Organic Chemistry 54(6), 1245-1249, 1989.*
Taylor et al., Journal of Organic Chemistry 54(6), 1249-1256, 1989.*
Rudakov et al., Zhurnal Organicheskoi Khimii 28(3), 589-599, 1992; CA 118: 168510, 1993.*

(Continued)

*Primary Examiner*—Venkataraman Balasubramanian
(74) *Attorney, Agent, or Firm*—Terence J. Bogie

(57) ABSTRACT

Novel compounds are provided which are 11-beta-hydroxysteroid dehydrogenase type I inhibitors. 11-beta-hydroxysteroid dehydrogenase type I inhibitors are useful in treating, preventing, or slowing the progression of diseases requiring 11-beta-hydroxysteroid dehydrogenase type I inhibitor therapy. These novel compounds have the structure:

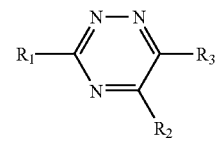

or stereoisomers or prodrugs or pharmaceutically acceptable salts thereof, wherein $R_1$, $R_2$ and $R_3$ are defined herein.

25 Claims, No Drawings

OTHER PUBLICATIONS

Kono et al., Yakugaku Zasshi, 108(2), 142-149, 1988; CA 109: 230953, 1988.*

Lalezari et al., Journal of Heterocyclic Chemistry, 8(4), 689-691, 1971; CA 75: 151763, 1971.*

Keen et al., Journal of Heterocyclic Chemistry, 13(4), 807-811, 1976; CA 85: 192678, 1976.*

Metz, DD 13175; CA 53: 40052, 1959.*

Kono et al., Chemical & Pharmaceutical Bulletin, 36(5), 1721-1726, 1988; CA 109: 230957, 1988.*

Koenig, DE 3305804; CA 102: 78573, 1985.*

Ewald, Justus Liebigs Annalen der Chemie, 10: 1718-1724, 1977; CA 88: 121117, 1977.*

Hammer et al., Best Practice & Research Clinical Endocrinology & Metabolism, 20(3), 337-353, 2006.*

Skott et al., Pharmacology & Therapeutics 111, 495-507, 2006.*

Yeh, V.S.C., et al., "A Highly Efficiet Synthesis of Potent and Slective Butyrolactam Inhibitors of 11β-Hsd1†", Organic Letters, vol. 0, No. 0, pp. A-D (2006).

Temple, C. et al., "Potential Antimitotic Agents. Synthesis of some Ethyl Benzopyrazin-7-ylcarbamates, Ethyl Pyrido[3,4-b]pyrazin-7-ylcarbamates, and Ethyl Pyrido[3,4-e]-as-traizin-7-ylcarbamates", J. Med. Chem., vol. 33, pp. 3044-3050 (1990).

Konno, S. et al., "Studies on as-Triazine Derivaties. XVIII. Synthesisof 5,6-Diaryl-1,2,4-triazine Derivatives as Blood Platelet Aggregation Inhibitors", Pharmaceutical Society of Japan, Journal—Yakugaku Zasshi, vol. 112, No. 10, pp. 729-741 (1992).

Oda, H. et al., "Synthesis and Herbicidal Activities of Pyridazidazino[4,5-e]-1,2,4-triazines", GIFU Pharmaceutical University. Newsletter, GIFU Yakka Daigaku, vol. 36, pp. 42-48 (1987).

Kolobova et al., "Choice criterions of individual triazine compounds with high inhibiting ability", Bashkirskii Khimicheskii Zhurnal, vol. 11, No. 2, pp. 58-61 (2004).

Tanaka, A. et al., "Studies on Anti-platelet agents V. Synthesis and structure-activity relationship of 3-substituted 5,6-Bis(4-methoxyphenyl)-1,2,4-triazines", Chem. Pharm. Bull. vol. 42, No. 9, pp. 1835-1840 (1994).

Konno, S. et al., "Studies on as-Triazine Derivaties. XIX. Synthesisof 2,3-Diarylpyrazine and 2,3-Diarylpyridine Derivatives as Blood Platelet Aggregation Inhibitors", Pharmaceutical Society of Japan, vol. 113, No. 1, pp. 40-52 (1993).

Tanaka, A. et al., "Studies on Anti-platelet agents IV. A Series of 2-Substituted 4,5-Bis(4-methoxyphenyl)pyrimidines as Novel Anti-platelet Agents", Chem. Pharm. Bull. vol. 42, No. 9, pp. 1828-1834 (1994).

* cited by examiner

TRIAZINE 11-BETA HYDROXYSTEROID DEHYDROGENASE TYPE 1 INHIBITORS

RELATED APPLICATION

This application claims the benefit of U.S. Provisional Application No. 60/778,159, filed on Mar. 1, 2006, incorporated herein by reference in its entirety.

BACKGROUND OF THE INVENTION

The steroid hormone cortisol is a key regulator of many physiological processes. However, an excess of cortisol, as occurs in Cushing's Disease, provokes severe metabolic abnormalities including: type 2 diabetes, cardiovascular disease, obesity, and osteoporosis. Many patients with these diseases, however, do not show significant increases in plasma cortisol levels. In addition to plasma cortisol, individual tissues can regulate their glucocorticoid tone via the in situ conversion of inactive cortisone to the active hormone cortisol. Indeed, the normally high plasma concentration of cortisone provides a ready supply of precursor for conversion to cortisol via the intracellular enzyme 11-beta-hydroxysteroid dehydrogenase type I (11-beta-HSD1).

11-beta-HSD1 is a member of the short chain dehydrogenase superfamily of enzymes. By catalyzing the conversion of biologically inactive cortisone to cortisol, 11-beta-HSD1 controls the intracellular glucocorticoid tone according to its expression and activity levels. In this manner, 11-beta-HSD1 can determine the overall metabolic status of the organ. 11-beta-HSD1 is expressed at high levels in the liver and at lower levels in many metabolically active tissues including the adipose, the CNS, the pancreas, and the pituitary. Taking the example of the liver, it is predicted that high levels of 11-beta-HSD1 activity will stimulate gluconeogenesis and overall glucose output. Conversely, reduction of 11-beta-HSD1 activity will downregulate gluconeogenesis resulting in lower plasma glucose levels.

Various studies have been conducted that support this hypothesis. For example, transgenic mice expressing 2× the normal level of 11-beta-HSD1 in only the adipose tissue show abdominal obesity, hyperglycemia, and insulin resistance. (H. Masuzaki, J. Paterson, H. Shinyama, N. M. Morton, J. J. Mullins, J. R. Seckl, J. S. Flier, A Transgenic Model of Visceral Obesity and the Metabolic Syndrome, *Science* 294: 2166-2170 (2001). Conversely, when the 11-beta-HSD1 gene is ablated by homologous recombination, the resulting mice are resistant to diet induced obesity and the accompanying dysregulation of glucose metabolism (N. M. Morton, J. M. Paterson, H. Masuzaki, M. C. Holmes, B. Staels, C. Fievet, B. R. Walker, J. S. Flier, J. J. Mullings, J. R. Seckl, Novel Adipose Tissue-Mediated Resistance to Diet-induced Visceral Obesity in 11β-Hydroxysteroid Dehydrogenase Type 1-Deficient Mice. *Diabetes* 53: 931-938 (2004). In addition, treatment of genetic mouse models of obesity and diabetes (ob/ob, db/db and KKAy mice) with a specific inhibitor of 11-beta-HSD1 causes a decrease in glucose output from the liver and an overall increase in insulin sensitivity (P. Alberts, C. Nilsson, G. Selen, L. O. M. Engblom, N. H. M. Edling, S. Norling, G. Klingstrom, C. Larsson, M. Forsgren, M. Ashkzari, C. E. Nilsson, M. Fiedler, E. Bergqvist, B. Ohman, E. Bjorkstrand, L. B. Abrahmsen, Selective Inhibition of 11β-Hydroxysteroid Dehydrogenase Type I Improves Hepatic Insuling Sensuitivity in Hyperglycemic Mice Strains, *Endocrinology* 144: 4755-4762 (2003)). Based in part on these studies, it is believed that local control of cortisol levels is important in metabolic diseases in these model systems. In addition, the results of these studies also suggest that inhibition of 11-beta-HSD1 will be a viable strategy for treating metabolic diseases such as type 2 diabetes, obesity, and the metabolic syndrome.

Lending further support to this idea are the results of a series of preliminary clinical studies. For example, several reports have shown that adipose tissue from obese individuals has elevated levels of 11-beta-HSD1 activity. In addition, studies with carbenoxolone, a natural product derived from licorice that inhibits both 11-beta-HSD1 and 11-beta-HSD2 (converts cortisol to cortisone in kidney) have shown promising results. A seven day, double blind, placebo controlled, cross over study with carbenoxolone in mildly overweight individuals with type 2 diabetes showed that patients treated with the inhibitor, but not the placebo group, displayed a decrease in hepatic glucose production (R. C. Andrews, O. Rooyackers, B. R. Walker, *J. Clin. Endocrinol. Metab.* 88: 285-291 (2003)). This observation is consistent with the inhibition of 11-beta-HSD1 in the liver. Furthermore, another clinical study reported that the inhibition of 11-beta-HSD1 may provide a novel treatment option for patients with glaucoma (Rauz et al., *IOVS*, Vol. 42, No. 9, pp. 2037-2042 (August 2001)). The results of these preclinical and early clinical studies strongly support the concept that treatment with a potent and selective inhibitor of 11-beta-HSD1 will be an efficacious therapy in patients afflicted with various disorders.

SUMMARY OF THE INVENTION

In accordance with the present invention, aryl and heterocyclyl and related compounds are provided that have the general structure of formula I:

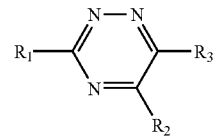

wherein $R_1$, $R_2$ and $R_3$ are defined below.

Compounds of the present invention inhibit the activity of the enzyme Compounds of the present invention inhibit the activity of the enzyme 11-beta-hydroxysteroid dehydrogenase type I. Consequently, the compounds of the present invention may be used in the treatment of multiple diseases or disorders associated with 11-beta-hydroxysteroid dehydrogenase type I, such as diabetes and related conditions, microvascular complications associated with diabetes, the macrovascular complications associated with diabetes, cardiovascular diseases, Metabolic Syndrome and its component conditions, and other maladies. Examples of diseases or disorders associated with the activity of the enzyme 11-beta-hydroxysteroid dehydrogenase type I that can be prevented, inhibited, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dislipidemia, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy and glaucoma.

The present invention provides for compounds of formula I, pharmaceutical compositions employing such compounds, and for methods of using such compounds. In particular, the present invention provides a pharmaceutical composition comprising a therapeutically effective amount of a compound of formula I, alone or in combination with a pharmaceutically acceptable carrier.

Further, in accordance with the present invention, a method is provided for preventing, inhibiting, or treating the progression or onset of diseases or disorders associated with the activity of the enzyme 11-beta-hydroxysteroid dehydrogenase type I, such as defined above and hereinafter, wherein a therapeutically effective amount of a compound of formula I is administered to a mammalian, i.e., human, patient in need of treatment.

The compounds of the invention can be used alone, in combination with other compounds of the present invention, or in combination with one or more other agent(s).

Further, the present invention provides a method for preventing, inhibiting, or treating the diseases as defined above and hereinafter, wherein a therapeutically effective amount of a combination of a compound of formula I and another compound of formula I and/or at least one other type of therapeutic agent, is administered to a mammalian, i.e., human, patient in need of treatment.

DESCRIPTION OF THE INVENTION

In accordance with the present invention, compounds of formula I are provided

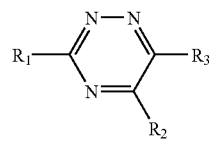

(I)

enantiomers, diastereomers, solvates, salts or prodrugs thereof wherein:

$R_1$ is alkyl, aryl, heteroaryl, cycloalkyl, adamantyl or heterocyclyl, other than heteroaryl, all of which may be optionally substituted with one or more $R_4$'s;

$R_2$ is hydrogen, halo, cyano, alkyl, alkenyl, alkynyl, cycloalkyl, aryl, heteroaryl, heterocyclyl, —$NR_9C(=O)R_9$, —$NR_9C(=O)OR_9'$, —$NR_9C(=O)NR_9R_9$, —$OC(=O)NR_9R_9$, —$C(=O)NR_9R_9$, —$NR_9R_9$, —$C(=O)R_9$, —$C(=O)OR_9$, —$OR_9$, —$SR_9$, —$SO_2R_9'$, —$SO_2NR_9R_9$, nitro, —$OP(=O)(OR_9)_2$ or —$NHSO_2R_9'$, wherein the alkyl, alkenyl, alkynyl, cycloalkyl, aryl, heteroaryl or heterocyclyl may be optionally substituted with one or more $R_4$'s;

$R_3$ is hydrogen, halo, cyano, alkyl, alkenyl, alkynyl, cycloalkyl, aryl, heteroaryl, heterocyclyl, —$NR_9C(=O)R_9$, —$NR_9C(=O)OR_9'$, —$NR_9C(=O)NR_9R_9$, —$OC(=O)NR_9R_9$, —$C(=O)NR_9R_9$, —$NR_9R_9$, —$C(=O)R_9$, —$C(=O)OR_9$, —$OR_9$, —$SR_9$, —$SO_2R_9'$, —$SO_2NR_9R_9$, nitro, —$OP(=O)(OR_9)_2$ or —$NHSO_2R_9'$, wherein the alkyl, alkenyl, alkynyl, cycloalkyl, aryl, heteroaryl or heterocyclyl may be optionally substituted with one or more $R_4$'s; or $R_2$ and $R_3$ are taken together with the carbon atoms to which each is attached to form a 4- to 15-membered mono-, bi- or tricylic ring, wherein said ring may be optionally substituted with one or more $R_4$'s; or $R_2$ and $R_3$ are taken together with the carbon atoms to which each is attached to form a 4- to 15-membered mono-, bi- or tricylic heterocyclyl ring wherein the heterocyclyl ring contains 1-4 heteroatoms selected from N, O, and S, and said ring may be optionally substituted with one or more $R_4$'s;

$R_4$, at each occurrence, is independently selected from alkyl, aryl, alkenyl, alkynyl, cycloalkyl, heteroaryl, heterocyclyl, halo, =O, —$NH_2$, —CN, —$NO_2$, —$C(=O)OH$, —$C(=O)OR_{10}$, —$OCF_3$, —$OR_{10}$, —OH, —SH, —$SR_{10}$, —$S(O)_3H$, —$P(O)_3H_2$, —$C(=O)NR_9R_9$, —$NR_9R_9$, —$S(O)_2NR_9R_9$, —$NR_9S(O)_2CF_3$, —$C(=O)NR_9S(O)_2R_9$, —$S(O)_2NR_9C(=O)OR_9$, —$S(O)_2NR_9C(=O)NR_9R_9$, —$C(=O)NR_9S(O)_2CF_3$, —$C(=O)R_{10}$, —$NR_9C(=O)H$, —$NR_9C(=O)R_{10}$, —$OC(=O)R_{10}$, —$OC(=O)NR_9R_9$, —$C(=NR_{14})NR_9R_9$, —$NHC(=NR_{14})NR_{14}R_{14}$, —$S(=O)R_{10}$, —$S(O)_2R_{10}$, —$NR_9C(=O)OR_8$ or —$NR_9S(O_2)R_8$, wherein the alkyl, aryl, alkenyl, alkynyl, cycloalkyl, heteroaryl or heterocyclyl may be optionally substituted with one or more $R_5$'s;

$R_5$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —$C(=O)OH$, —$C(=O)OR_{10}$, —$OCF_3$, —$OR_{10}$, —OH, —SH, —$SR_{10}$, —$S(O)_3H$, —$P(O)_3H_2$, —$C(=O)NR_9R_9$, —$NR_9R_9$, —$S(O)_2NR_9R_9$, —$NR_9S(O)_2CF_3$, —$C(=O)NR_9S(O)_2R_9$, —$S(O)_2NR_9C(=O)OR_9$, —$S(O)_2NR_9C(=O)NR_9R_9$, —$C(=O)NR_9S(O)_2CF_3$, —$C(=O)R_{10}$, —$NR_9C(=O)H$, —$NR_9C(=O)R_{10}$, —$OC(=O)R_{10}$, —$C(=NR_{14})NR_9R_9$, —$NHC(=NR_{14})NR_{14}R_{14}$, —$S(=O)R_{10}$, —$S(O)_2R_{10}$, —$NR_9C(=O)OR_8$ or —$NR_9S(O_2)R_8$;

$R_8$, at each occurrence, is independently alkyl or aryl;

$R_9$, at each occurrence, is independently hydrogen, alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S;

$R_9'$, at each occurrence, is independently alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —$C(=O)OH$, —$C(=O)OR_{14}$, —$OCF_3$, —$OR_{14}$, —OH, —SH, —$SR_{14}$, —$S(O)_3H$, —$P(O)_3H_2$, —$C(=O)NR_{14}R_{14}$, —$NR_{14}R_{14}$, —$S(O)_2NR_{14}R_{14}$, —$NR_{14}S(O)_2CF_3$, —$C(=O)NR_{14}S(O)_2R_{10}$, —$S(O)_2NR_{14}C(=O)OR_{10}$, —$S(O)_2NR_{14}C(=O)NR_{14}R_{14}$, —$C(=O)NR_{14}S(O)_2CF_3$, —$C(=O)R_{14}$, —$NR_{14}C(=O)H$, —$NR_{14}C(=O)R_{14}$, —$OC(=O)R_{14}$, —$C(=NR_{14})NR_{14}R_{14}$, —$NHC(=NR_{14})NR_{14}R_{14}$, —$S(=O)R_{14}$, —$S(O)_2R_{14}$, —$NR_{14}C(=O)OR_8$, —$NR_{14}S(O_2)R_8$ or arylalkyl;

$R_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl; and $R_{14}$, at each occurrence, is independently selected from hydrogen, alkyl, cycloalkyl or aryl.

In one embodiment, compounds of formula I are provided wherein:

$R_1$ is alkyl, aryl, heteroaryl, adamantyl, a 3-membered cycloalkyl or an 8- to 20-membered cycloalkyl, other than adamantyl, all of which may be optionally substituted with one or more $R_4$'s;

$R_2$ is hydrogen, halo, cyano, alkyl, alkenyl, alkynyl, cycloalkyl, aryl, heteroaryl, heterocyclyl, —NR$_9$C(=O)R$_9$, —NR$_9$C(=O)OR$_{9'}$, —NR$_9$C(=O)NR$_9$R$_9$, —OC(=O)NR$_9$R$_9$, —C(=O)NR$_9$R$_9$, —NR$_9$R$_9$, —C(=O)R$_9$, —C(=O)OR$_9$, —OR$_9$, —SR$_9$, —SO$_2$R$_{9'}$, —SO$_2$NR$_9$R$_9$, nitro, —OP(=O)(OR$_9$)$_2$ or —NHSO$_2$R$_{9'}$, wherein the alkyl, alkenyl, alkynyl, cycloalkyl, aryl, heteroaryl or heterocyclyl may be optionally substituted with one or more $R_4$'s;

$R_3$ is hydrogen, halo, cyano, alkyl, alkenyl, alkynyl, cycloalkyl, aryl, heteroaryl, heterocyclyl, —NR$_9$C(=O)R$_9$, —NR$_9$C(=O)OR$_{9'}$, —NR$_9$C(=O)NR$_9$R$_9$, —OC(=O)NR$_9$R$_9$, —C(=O)NR$_9$R$_9$, —NR$_9$R$_9$, —C(=O)R$_9$, —C(=O)OR$_9$, —OR$_9$, —SR$_9$, —SO$_2$R$_{9'}$, —SO$_2$NR$_9$R$_9$, nitro, —OP(=O)(OR$_9$)$_2$ or —NHSO$_2$R$_{9'}$, wherein the alkyl, alkenyl, alkynyl, cycloalkyl, aryl, heteroaryl or heterocyclyl may be optionally substituted with one or more $R_4$'s; or $R_2$ and $R_3$ are taken together with the carbon atoms to which each is attached to form a 4- to 15-membered mono-, bi- or tricylic ring, wherein said ring may be optionally substituted with one or more $R_4$'s; or $R_2$ and $R_3$ are taken together with the carbon atoms to which each is attached to form a 4- to 15-membered mono-, bi- or tricylic heterocyclyl ring wherein the heterocyclyl ring contains 1-4 heteroatoms selected from N, O, and S, and said ring may be optionally substituted with one or more $R_4$'s;

$R_4$, at each occurrence, is independently selected from alkyl, aryl, alkenyl, alkynyl, cycloalkyl, heteroaryl, heterocyclyl, halo, =O, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ or —NR$_9$S(O$_2$)R$_8$, wherein the alkyl, aryl, alkenyl, alkynyl, cycloalkyl, heteroaryl or heterocyclyl may be optionally substituted with one or more $R_5$'s;

$R_5$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ or —NR$_9$S(O$_2$)R$_8$;

$R_8$, at each occurrence, is independently alkyl or aryl;

$R_9$, at each occurrence, is independently hydrogen, alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S;

$R_{9'}$, at each occurrence, is independently alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl;

$R_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl; and $R_{14}$, at each occurrence, is independently selected from hydrogen, alkyl, cycloalkyl or aryl.

In another embodiment, compounds of formula I are provided wherein:

$R_1$ is aryl, heteroaryl, adamantyl, a 3-membered cycloalkyl or an 8- to 15-membered cycloalkyl, other than adamantyl, all of which may be optionally substituted with one or more $R_4$'s;

$R_2$ is hydrogen, halo, cyano, alkyl, alkenyl, alkynyl, cycloalkyl, aryl, heteroaryl, heterocyclyl, —NR$_9$C(=O)R$_9$, —NR$_9$C(=O)OR$_{9'}$, —NR$_9$C(=O)NR$_9$R$_9$, —OC(=O)NR$_9$R$_9$, —C(=O)NR$_9$R$_9$, —NR$_9$R$_9$, —C(=O)R$_9$, —C(=O)OR$_9$, —OR$_9$, —SR$_9$, —SO$_2$R$_{9'}$, —SO$_2$NR$_9$R$_9$, nitro, —OP(=O)(OR$_9$)$_2$ or —NHSO$_2$R$_{9'}$, wherein the alkyl, alkenyl, alkynyl, cycloalkyl, aryl, heteroaryl or heterocyclyl may be optionally substituted with one or more $R_4$'s;

$R_3$ is hydrogen, halo, cyano, alkyl, alkenyl, alkynyl, cycloalkyl, aryl, heteroaryl, heterocyclyl, —NR$_9$C(=O)R$_9$, —NR$_9$C(=O)OR$_9'$, —NR$_9$C(=O)NR$_9$R$_9$, —OC(=O) NR$_9$R$_9$, —C(=O)NR$_9$R$_9$, —NR$_9$R$_9$, —C(=O)R$_9$, —C(=O)OR$_9$, —OR$_9$, —SR$_9$, —SO$_2$R$_9'$, —SO$_2$NR$_9$R$_9$, nitro, —OP(=O)(OR$_9$)$_2$ or —NHSO$_2$R$_9$, wherein the alkyl, alkenyl, alkynyl, cycloalkyl, aryl, heteroaryl or heterocyclyl may be optionally substituted with one or more R$_4$'s; or $R_2$ and $R_3$ are taken together with the carbon atoms to which each is attached to form a 4- to 15-membered mono-, bi- or tricylic ring, wherein said ring may be optionally substituted with one or more R$_4$'s;

$R_4$, at each occurrence, is independently selected from alkyl, aryl, alkenyl, alkynyl, cycloalkyl, heteroaryl, heterocyclyl, halo, =O, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ or —NR$_9$S(O$_2$)R$_8$, wherein the alkyl, aryl, alkenyl, alkynyl, cycloalkyl, heteroaryl or heterocyclyl may be optionally substituted with one or more R$_5$'s;

$R_5$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ or —NR$_9$S(O$_2$)R$_8$;

$R_8$, at each occurrence, is independently alkyl or aryl;

$R_9$, at each occurrence, is independently hydrogen, alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S;

$R_{9'}$, at each occurrence, is independently alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl;

$R_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 R$_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl; and $R_{14}$, at each occurrence, is independently selected from hydrogen, alkyl, cycloalkyl or aryl.

In still another embodiment, compounds of formula I are provided wherein:

$R_1$ is aryl, heteroaryl, adamantyl, a 3-membered cycloalkyl or an 8- to 15-membered cycloalkyl, other than adamantyl, all of which may be optionally substituted with one or more R$_4$'s;

$R_2$ is hydrogen, halo, cyano, alkyl, cycloalkyl, aryl, heteroaryl, heterocyclyl, —NR$_9$C(=O)R$_9$, —NR$_9$C(=O)OR$_9'$, —NR$_9$C(=O)NR$_9$R$_9$, —OC(=O)NR$_9$R$_9$, —C(=O)NR$_9$R$_9$, —NR$_9$R$_9$, —C(=O)R$_9$, —C(=O)OR$_9$, —OR$_9$, —SR$_9$ or nitro, wherein the alkyl, cycloalkyl, aryl, heteroaryl or heterocyclyl may be optionally substituted with one or more R$_4$'s;

$R_3$ is hydrogen, halo, cyano, alkyl, cycloalkyl, aryl, heteroaryl, heterocyclyl, —NR$_9$C(=O)R$_9$, —NR$_9$C(=O)OR$_9'$, —NR$_9$C(=O)NR$_9$R$_9$, —OC(=O)NR$_9$R$_9$, —C(=O)NR$_9$R$_9$, —NR$_9$R$_9$, —C(=O)R$_9$, —C(=O)OR$_9$, —OR$_9$, —SR$_9$ or nitro, wherein the alkyl, cycloalkyl, aryl, heteroaryl or heterocyclyl may be optionally substituted with one or more R$_4$'s; or $R_2$ and $R_3$ are taken together with the carbon atoms to which each is attached to form a 4- to 15-membered mono-, bi- or tricylic ring, wherein said ring may be optionally substituted with one or more R$_4$'s;

$R_4$, at each occurrence, is independently selected from alkyl, aryl, alkenyl, alkynyl, cycloalkyl, heteroaryl, heterocyclyl, halo, =O, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ or —NR$_9$S(O$_2$)R$_8$, wherein the alkyl, aryl, alkenyl, alkynyl, cycloalkyl, heteroaryl or heterocyclyl may be optionally substituted with one or more R$_5$'s;

$R_5$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ or —NR$_9$S(O$_2$)R$_8$;

R$_8$, at each occurrence, is independently alkyl or aryl;

R$_9$, at each occurrence, is independently hydrogen, alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S;

R$_{9'}$, at each occurrence, is independently alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S;

R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_4$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl;

R$_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 R$_{10a}$, and the heterocyclyl and heterocyclylalkyl contain 1-4 heteroatoms selected from N, O, and S;

R$_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_4$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl; and R$_{14}$, at each occurrence, is independently selected from hydrogen, alkyl, cycloalkyl or aryl.

In yet still another embodiment, compounds of formula I are provided wherein:

R$_1$ is aryl, heteroaryl, adamantyl, a 3-membered cycloalkyl or an 8- to 15-membered cycloalkyl, other than adamantyl, all of which may be optionally substituted with one or more R$_4$'s;

R$_2$ is halo, cyano, alkyl, cycloalkyl, aryl, heteroaryl, heterocyclyl, —NR$_9$C(=O)R$_9$, —NR$_9$C(=O)OR$_{9'}$, —NR$_9$C(=O)NR$_9$R$_9$, —OC(=O)NR$_9$R$_9$, —C(=O)NR$_9$R$_9$, —NR$_9$R$_9$, —C(=O)R$_9$, —C(=O)OR$_9$, —OR$_9$, —SR$_9$ or nitro, wherein the alkyl, cycloalkyl, aryl, heteroaryl or heterocyclyl may be optionally substituted with one or more R$_4$'s;

R$_3$ is hydrogen, halo, cyano, alkyl, cycloalkyl, aryl, heteroaryl, heterocyclyl, —NR$_9$C(=O)R$_9$, —NR$_9$C(=O)OR$_{9'}$, —NR$_9$C(=O)NR$_9$R$_9$, —OC(=O)NR$_9$R$_9$, —C(=O)NR$_9$R$_9$, —NR$_9$R$_9$, —C(=O)R$_9$, —C(=O)OR$_9$, —OR$_9$, —SR$_9$ or nitro, wherein the alkyl, cycloalkyl, aryl, heteroaryl or heterocyclyl may be optionally substituted with one or more R$_4$'s; or R$_2$ and R$_3$ are taken together with the carbon atoms to which each is attached to form a 4- to 15-membered mono-, bi- or tricylic ring, wherein said ring may be optionally substituted with one or more R$_4$'s;

R$_4$, at each occurrence, is independently selected from alkyl, aryl, alkenyl, alkynyl, cycloalkyl, heteroaryl, heterocyclyl, halo, =O, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ or —NR$_9$S(O$_2$)R$_8$, wherein the alkyl, aryl, alkenyl, alkynyl, cycloalkyl, heteroaryl or heterocyclyl may be optionally substituted with one or more R$_5$'s;

R$_5$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ or —NR$_9$S(O$_2$)R$_8$;

R$_8$, at each occurrence, is independently alkyl or aryl;

R$_9$, at each occurrence, is independently hydrogen, alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S;

R$_{9'}$, at each occurrence, is independently alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S;

R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl;

R$_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 R$_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O)$_2$R$_8$ or arylalkyl; and $R_{14}$, at each occurrence, is independently selected from hydrogen, alkyl, cycloalkyl or aryl.

In one embodiment, compounds of formula I are provided wherein:

$R_1$ is aryl, heteroaryl, adamantyl, a 3-membered cycloalkyl or an 8- to 15-membered cycloalkyl, other than adamantyl, all of which may be optionally substituted with one or more $R_4$'s;

$R_2$ is halo, cyano, alkyl, cycloalkyl, aryl, heteroaryl, heterocyclyl, —NR$_9$C(=O)R$_9$, —NR$_9$C(=O)OR$_9$', —NR$_9$C(=O)NR$_9$R$_9$, —OC(=O)NR$_9$R$_9$, —C(=O)NR$_9$R$_9$, —NR$_9$R$_9$, —C(=O)R$_9$, —C(=O)OR$_9$, —OR$_9$ or —SR$_9$, wherein the alkyl, cycloalkyl, aryl, heteroaryl, heterocyclyl may be optionally substituted with one or more $R_4$'s;

$R_3$ is hydrogen, halo, cyano, alkyl, cycloalkyl, aryl, heteroaryl, heterocyclyl, —NR$_9$C(=O)R$_9$, —NR$_9$C(=O)OR$_9$', —NR$_9$C(=O)NR$_9$R$_9$, —OC(=O)NR$_9$R$_9$, —C(=O)NR$_9$R$_9$, —NR$_9$R$_9$, —C(=O)R$_9$, —C(=O)OR$_9$, —OR$_9$, or —SR$_9$, wherein the alkyl, cycloalkyl, aryl, heteroaryl, heterocyclyl may be optionally substituted with one or more $R_4$'s; or $R_2$ and $R_3$ are taken together with the carbon atoms to which each is attached to form a 4- to 15-membered mono-, bi- or tricylic ring, wherein said ring may be optionally substituted with one or more $R_4$'s;

$R_4$, at each occurrence, is independently selected from alkyl, aryl, alkenyl, alkynyl, cycloalkyl, heteroaryl, heterocyclyl, halo, =O, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ or —NR$_9$S(O)$_2$R$_8$, wherein the alkyl, aryl, alkenyl, alkynyl, cycloalkyl, heteroaryl or heterocyclyl may be optionally substituted with one or more $R_5$'s;

$R_5$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ or —NR$_9$S(O)$_2$R$_8$;

$R_8$, at each occurrence, is independently alkyl or aryl;

$R_9$, at each occurrence, is independently hydrogen, alkyl, alkoxy, cycloalkyl, aryl, arylalkyl, heteroaryl, heteroarylalkyl, heterocyclyl or heterocyclylalkyl, wherein the heteroaryl, heteroarylalkyl, heterocyclyl or heterocyclylalkyl contain 1-4 heteroatoms selected from N, O, and S;

$R_9$', at each occurrence, is independently alkyl, alkoxy, cycloalkyl, aryl, arylalkyl, heteroaryl, heteroarylalkyl, heterocyclyl or heterocyclylalkyl, wherein the heteroaryl, heteroarylalkyl, heterocyclyl or heterocyclylalkyl contain 1-4 heteroatoms selected from N, O, and S;

$R_{10}$, at each occurrence, is independently selected from alkyl, alkenyl, alkynyl, aryl, arylalkyl, heterocyclyl or heterocyclylalkyl, wherein the heterocyclyl and heterocyclylalkyl contain 1-4 heteroatoms selected from N, O, and S; and $R_{14}$, at each occurrence, is independently selected from hydrogen, alkyl, cycloalkyl or aryl.

In another embodiment, compounds of formula I are provided wherein:

$R_1$ is aryl, adamantyl, a 3-membered cycloalkyl or an 8- to 15-membered cycloalkyl, other than adamantyl, all of which may be optionally substituted with one or more $R_4$'s;

$R_2$ is halo, alkyl, cycloalkyl, aryl, heteroaryl, heterocyclyl, —NR$_9$C(=O)R$_9$, —NR$_9$C(=O)OR$_9$', —NR$_9$C(=O)NR$_9$R$_9$, —OC(=O)NR$_9$R$_9$, —C(=O)NR$_9$R$_9$, —NR$_9$R$_9$, —C(=O)R$_9$, —C(=O)OR$_9$ or —OR$_9$, wherein the alkyl, cycloalkyl, aryl, heteroaryl or heterocyclyl may be optionally substituted with one or more $R_4$'s;

$R_3$ is hydrogen, halo, alkyl, cycloalkyl, aryl, heteroaryl, heterocyclyl, —NR$_9$C(=O)R$_9$, —NR$_9$C(=O)OR$_9$', —NR$_9$C(=O)NR$_9$R$_9$, —OC(=O)NR$_9$R$_9$, —C(=O)NR$_9$R$_9$, —NR$_9$R$_9$, —C(=O)R$_9$, —C(=O)OR$_9$, or —OR$_9$, wherein the alkyl, cycloalkyl, aryl, heteroaryl or heterocyclyl may be optionally substituted with one or more $R_4$'s; or $R_2$ and $R_3$ are taken together with the carbon atoms to which each is attached to form a 4- to 15-membered mono-, bi- or tricylic ring, wherein said ring may be optionally substituted with one or more $R_4$'s;

$R_4$, at each occurrence, is independently selected from alkyl, aryl, cycloalkyl, heteroaryl, heterocyclyl, halo, =O, —NH$_2$, —CN, —NO$_2$, —C(=O)OH, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —S(=O)R$_{10}$, —S(O)$_2$R$_{10}$, —NR$_9$C(=O)OR$_8$, or —NR$_9$S(O)$_2$R$_8$, wherein the alkyl, aryl, cycloalkyl, heteroaryl, or heterocyclyl may be optionally substituted with one or more $R_5$'s;

$R_5$, at each occurrence, is independently selected from alkyl, haloalkyl, aryl, cycloalkyl, heteroaryl, heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —S(=O)R$_{10}$, —S(O)$_2$R$_{10}$, —NR$_9$C(=O)OR$_8$ or —NR$_9$S(O$_2$)R$_8$;

$R_8$, at each occurrence, is independently alkyl or aryl;

$R_9$, at each occurrence, is independently hydrogen, alkyl, alkoxy, cycloalkyl, aryl, heteroaryl or heterocyclyl, wherein the heteroaryl or heterocyclyl contain 1-4 heteroatoms selected from N, O, and S; and $R_{10}$, at each occurrence, is independently selected from alkyl, aryl or heterocyclyl, wherein the heterocyclyl contains 1-4 heteroatoms selected from N, O, and S.

In still another embodiment, compounds of formula I are provided wherein:

$R_1$ is adamantyl, a 3-membered cycloalkyl or an 8- to 15-membered cycloalkyl, other than adamantyl, all of which may be optionally substituted with one or more $R_4$'s;

$R_2$ is alkyl, cycloalkyl, aryl, heteroaryl, heterocyclyl, —$NR_9C(=O)R_9$, —$NR_9C(=O)OR_{9'}$, —$NR_9C(=O)NR_9R_9$, —$OC(=O)NR_9R_9$, —$C(=O)NR_9R_9$, —$NR_9R_9$, —$C(=O)R_9$, —$C(=O)OR_9$ or —$OR_9$, wherein the alkyl, cycloalkyl, aryl, heteroaryl or heterocyclyl may be optionally substituted with one or more $R_4$'s;

$R_3$ is hydrogen, alkyl, cycloalkyl, aryl, heteroaryl, heterocyclyl, —$NR_9C(=O)R_9$, —$NR_9C(=O)OR_{9'}$, —$NR_9C(=O)NR_9R_9$, —$OC(=O)NR_9R_9$, —$C(=O)NR_9R_9$, —$NR_9R_9$, —$C(=O)R_9$, —$C(=O)OR_9$, or —$OR_9$, wherein the alkyl, cycloalkyl, aryl, heteroaryl or heterocyclyl may be optionally substituted with one or more $R_4$'s; or $R_2$ and $R_3$ are taken together with the carbon atoms to which each is attached to form a 4- to 15-membered mono-, bi- or tricylic ring, wherein said ring may be optionally substituted with one or more $R_4$'s;

$R_4$, at each occurrence, is independently selected from alkyl, aryl, cycloalkyl, heteroaryl, heterocyclyl, halo, —$NH_2$, —CN, —$NO_2$, —$C(=O)OH$, —$C(=O)OR_{10}$, —$OCF_3$, —$OR_{10}$, —OH, —SH, —$SR_{10}$, —$C(=O)NR_9R_9$, —$NR_9R_9$, —$S(O)_2NR_9R_9$, —$NR_9S(O)_2CF_3$, —$C(=O)NR_9S(O)_2R_9$, —$S(O)_2NR_9C(=O)OR_9$, —$S(O)_2NR_9C(=O)NR_9R_9$, —$C(=O)NR_9S(O)_2CF_3$, —$C(=O)R_{10}$, —$NR_9C(=O)H$, —$NR_9C(=O)R_{10}$, —$OC(=O)R_{10}$, —$OC(=O)NR_9R_9$, —$S(=O)R_{10}$ or —$S(O)_2R_{10}$, wherein the alkyl, aryl, cycloalkyl, heteroaryl or heterocyclyl may be optionally substituted with one or more $R_5$'s;

$R_5$, at each occurrence, is independently selected from alkyl, haloalkyl, aryl, cycloalkyl, heteroaryl, heterocyclyl, halo, —$NH_2$, —CN, —$NO_2$, —$C(=O)OH$, —$C(=O)OR_{10}$, —$OCF_3$, —$OR_{10}$, —OH, —SH, —$SR_{10}$, —$C(=O)NR_9R_9$, —$NR_9R_9$, —$S(O)_2NR_9R_9$, —$NR_9S(O)_2CF_3$, —$C(=O)NR_9S(O)_2R_9$, —$S(O)_2NR_9C(=O)OR_9$, —$S(O)_2NR_9C(=O)NR_9R_9$, —$C(=O)NR_9S(O)_2CF_3$, —$C(=O)R_{10}$, —$NR_9C(=O)H$, —$NR_9C(=O)R_{10}$, —$OC(=O)R_{10}$, —$S(=O)R_{10}$ or —$S(O)_2R_{10}$;

$R_9$, at each occurrence, is independently hydrogen, alkyl, cycloalkyl, aryl, heteroaryl or heterocyclyl, wherein the heteroaryl or heterocyclyl contain 1-4 heteroatoms selected from N, O, and S; and $R_{10}$, at each occurrence, is independently selected from alkyl, aryl or heterocyclyl, wherein the heterocyclyl contains 1-4 heteroatoms selected from N, O, and S.

In yet still another embodiment, compounds of formula I are provided wherein:

$R_1$ is a 4- to 7-membered cycloalkyl or heterocyclyl, other than heteroaryl, all of which may be optionally substituted with one or more $R_4$'s;

$R_2$ is halo, cyano, alkyl, alkenyl, alkynyl, cycloalkyl, aryl, heteroaryl, heterocyclyl, —$NR_9C(=O)OR_{9'}$, —$NR_9C(=O)NR_9R_9$, —$C(=O)R_9$, —$SR_9$ or —$SO_2R_{9'}$, or wherein the alkyl, alkenyl, alkynyl, cycloalkyl, aryl, heteroaryl or heterocyclyl may be optionally substituted with one or more $R_4$'s;

$R_3$ is hydrogen, halo, cyano, alkyl, alkenyl, alkynyl, cycloalkyl, aryl, heteroaryl, heterocyclyl, —$NR_9C(=O)R_9$, —$NR_9C(=O)OR_{9'}$, —$NR_9C(=O)NR_9R_9$, —$OC(=O)NR_9R_9$, —$C(=O)NR_9R_9$, —$NR_9R_9$, —$C(=O)R_9$, —$C(=O)OR_9$, —$OR_9$, —$SR_9$, —$SO_2R_{9'}$, —$SO_2NR_9R_9$, nitro, —$OP(=O)(OR_9)_2$ or —$NHSO_2R_{9'}$, wherein the alkyl, alkenyl, alkynyl, cycloalkyl, aryl, heteroaryl or heterocyclyl may be optionally substituted with one or more $R_4$'s; or $R_2$ and $R_3$ are taken together with the carbon atoms to which each is attached to form a 4- to 15-membered mono-, bi- or tricylic ring, wherein said ring may be optionally substituted with one or more $R_4$'s; or $R_2$ and $R_3$ are taken together with the carbon atoms to which each is attached to form a 4- to 15-membered mono-, bi- or tricylic heterocyclyl ring wherein the heterocyclyl ring contains 1-4 heteroatoms selected from N, O, and S, and said ring may be optionally substituted with one or more $R_4$'s;

$R_4$, at each occurrence, is independently selected from alkyl, aryl, alkenyl, alkynyl, cycloalkyl, heteroaryl, heterocyclyl, halo, =O, —$NH_2$, —CN, —$NO_2$, —$C(=O)OH$, —$C(=O)OR_{10}$, —$OCF_3$, —$OR_{10}$, —OH, —SH, —$SR_{10}$, —$S(O)_3H$, —$P(O)_3H_2$, —$C(=O)NR_9R_9$, —$NR_9R_9$, —$S(O)_2NR_9R_9$, —$NR_9S(O)_2CF_3$, —$C(=O)NR_9S(O)_2R_9$, —$S(O)_2NR_9C(=O)OR_9$, —$S(O)_2NR_9C(=O)NR_9R_9$, —$C(=O)NR_9S(O)_2CF_3$, —$C(=O)R_{10}$, —$NR_9C(=O)H$, —$NR_9C(=O)R_{10}$, —$OC(=O)R_{10}$, —$OC(=O)NR_9R_9$, —$C(=NR_{14})NR_9R_9$, —$NHC(=NR_{14})NR_{14}R_{14}$, —$S(=O)R_{10}$, —$S(O)_2R_{10}$, —$NR_9C(=O)OR_8$ or —$NR_9S(O_2)R_8$, wherein the alkyl, aryl, alkenyl, alkynyl, cycloalkyl, heteroaryl or heterocyclyl may be optionally substituted with one or more $R_5$'s;

$R_5$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —$C(=O)OH$, —$C(=O)OR_{10}$, —$OCF_3$, —$OR_{10}$, —OH, —SH, —$SR_{10}$, —$S(O)_3H$, —$P(O)_3H_2$, —$C(=O)NR_9R_9$, —$NR_9R_9$, —$S(O)_2NR_9R_9$, —$NR_9S(O)_2CF_3$, —$C(=O)NR_9S(O)_2R_9$, —$S(O)_2NR_9C(=O)OR_9$, —$S(O)_2NR_9C(=O)NR_9R_9$, —$C(=O)NR_9S(O)_2CF_3$, —$C(=O)R_{10}$, —$NR_9C(=O)H$, —$NR_9C(=O)R_{10}$, —$OC(=O)R_{10}$, —$C(=NR_{14})NR_9R_9$, —$NHC(=NR_{14})NR_{14}R_{14}$, —$S(=O)R_{10}$, —$S(O)_2R_{10}$, —$NR_9C(=O)OR_8$ or —$NR_9S(O)_2R_8$;

$R_8$, at each occurrence, is independently alkyl or aryl;

$R_9$, at each occurrence, is independently hydrogen, alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S;

$R_{9'}$, at each occurrence, is independently alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —$C(=O)OH$, —$C(=O)OR_4$, —$OCF_3$, —$OR_{14}$, —OH, —SH, —$SR_{14}$, —$S(O)_3H$, —$P(O)_3H_2$, —$C(=O)NR_{14}R_{14}$, —$NR_{14}R_{14}$, —$S(O)_2NR_{14}R_{14}$, —$NR_{14}S(O)_2CF_3$, —$C(=O)NR_{14}S(O)_2R_{10}$, —$S(O)_2NR_{14}C(=O)OR_{10}$, —$S(O)_2NR_{14}C(=O)NR_{14}R_{14}$, —$C(=O)NR_{14}S(O)_2CF_3$, —$C(=O)R_{14}$, —$NR_{14}C(=O)H$, —$NR_{14}C(=O)R_{14}$, —$OC(=O)R_{14}$, —$C(=NR_{14})NR_{14}R_{14}$, —$NHC(=NR_{14})NR_{14}R_{14}$, —$S(=O)R_{14}$, —$S(O)_2R_{14}$, —$NR_{14}C(=O)OR_8$, —$NR_{14}S(O_2)R_8$ or arylalkyl;

$R_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl; and $R_{14}$, at each occurrence, is independently selected from hydrogen, alkyl, cycloalkyl or aryl.

In one embodiment, compounds of formula I are provided wherein:

$R_1$ is a 4- to 7-membered cycloalkyl or heterocyclyl, other than heteroaryl, all of which may be optionally substituted with one or more $R_4$'s;

$R_2$ is halo, cyano, alkyl, alkenyl, alkynyl, cycloalkyl, aryl, heteroaryl, heterocyclyl, —NR$_9$C(=O)NR$_9$R$_9$, —C(=O)R$_9$, —SR$_9$ or —SO$_2$R$_9$, or wherein the alkyl, alkenyl, alkynyl, cycloalkyl, aryl, heteroaryl or heterocyclyl may be optionally substituted with one or more $R_4$'s;

$R_3$ is hydrogen, halo, cyano, alkyl, cycloalkyl, aryl, heteroaryl, heterocyclyl, —NR$_9$C(=O)R$_9$, —NR$_9$C(=O)OR$_{9'}$, —NR$_9$C(=O)NR$_9$R$_9$, —OC(=O)NR$_9$R$_9$, —C(=O)NR$_9$R$_9$, —NR$_9$R$_9$, —C(=O)R$_9$, —C(=O)OR$_9$, —OR$_9$, —SR$_9$, —SO$_2$R$_9$, —SO$_2$NR$_9$R$_9$, nitro, —OP(=O)(OR$_9$)$_2$ or —NHSO$_2$R$_{9'}$, wherein the alkyl, cycloalkyl, aryl, heteroaryl or heterocyclyl may be optionally substituted with one or more $R_4$'s; or $R_2$ and $R_3$ are taken together with the carbon atoms to which each is attached to form a 4- to 15-membered mono-, bi- or tricylic ring, wherein said ring may be optionally substituted with one or more $R_4$'s;

$R_4$, at each occurrence, is independently selected from alkyl, aryl, alkenyl, alkynyl, cycloalkyl, heteroaryl, heterocyclyl, halo, =O, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ or —NR$_9$S(O$_2$)R$_8$, wherein the alkyl, aryl, alkenyl, alkynyl, cycloalkyl, heteroaryl or heterocyclyl may be optionally substituted with one or more $R_5$'s;

$R_5$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ or —NR$_9$S(O$_2$)R$_8$;

$R_8$, at each occurrence, is independently alkyl or aryl;

$R_9$, at each occurrence, is independently hydrogen, alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S;

$R_{9'}$, at each occurrence, is independently alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl;

$R_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl; and $R_{14}$, at each occurrence, is independently selected from hydrogen, alkyl, cycloalkyl or aryl.

In another embodiment, compounds of formula I are provided wherein:

$R_1$ is a 4- to 7-membered cycloalkyl or heterocyclyl, other than heteroaryl, all of which may be optionally substituted with one or more $R_4$'s;

$R_2$ is halo, cyano, alkyl, alkenyl, alkynyl, cycloalkyl, aryl, heteroaryl, heterocyclyl, —C(=O)R$_9$, —SR$_9$ or —SO$_2$R$_9$, or wherein the alkyl, alkenyl, alkynyl, cycloalkyl, aryl, heteroaryl or heterocyclyl may be optionally substituted with one or more $R_4$'s;

$R_3$ is hydrogen, halo, cyano, alkyl, cycloalkyl, aryl, heteroaryl, heterocyclyl, —NR$_9$C(=O)R$_9$, —NR$_9$C(=O)OR$_{9'}$, —NR$_9$C(=O)NR$_9$R$_9$, —OC(=O)NR$_9$R$_9$, —C(=O)NR$_9$R$_9$, —NR$_9$R$_9$, —C(=O)R$_9$, —C(=O)OR$_9$, —OR$_9$, —SR$_9$ or nitro, wherein the alkyl, cycloalkyl, aryl, heteroaryl or heterocyclyl may be optionally substituted with one or more $R_4$'s;

$R_4$, at each occurrence, is independently selected from alkyl, aryl, alkenyl, alkynyl, cycloalkyl, heteroaryl, heterocyclyl, halo, =O, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ or —NR$_9$S(O$_2$)R$_8$, wherein the alkyl, aryl, alkenyl, alkynyl, cycloalkyl, heteroaryl or heterocyclyl may be optionally substituted with one or more R$_5$'s;

R$_5$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ or —NR$_9$S(O$_2$)R$_8$;

R$_8$, at each occurrence, is independently alkyl or aryl;

R$_9$, at each occurrence, is independently hydrogen, alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S;

R$_{9'}$, at each occurrence, is independently alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S;

R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl;

R$_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 R$_{10a}$, and the heterocyclyl and heterocyclylalkyl contain 1-4 heteroatoms selected from N, O, and S;

R$_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl; and R$_{14}$, at each occurrence, is independently selected from hydrogen, alkyl, cycloalkyl or aryl.

In still another embodiment, compounds of formula I are provided wherein:

R$_1$ is a 4- to 7-membered cycloalkyl or heterocyclyl, other than heteroaryl, all of which may be optionally substituted with one or more R$_4$'s;

R$_2$ is halo, cyano, alkyl, alkenyl, alkynyl, cycloalkyl, aryl, heteroaryl, heterocyclyl, —SR$_9$ or —SO$_2$R$_{9'}$, or wherein the alkyl, alkenyl, alkynyl, cycloalkyl, aryl, heteroaryl, or heterocyclyl may be optionally substituted with one or more R$_4$'s;

R$_3$ is halo, cyano, alkyl, cycloalkyl, aryl, heteroaryl, heterocyclyl, —NR$_9$C(=O)R$_9$, —NR$_9$C(=O)OR$_{9'}$, —NR$_9$C(=O)NR$_9$R$_9$, —OC(=O)NR$_9$R$_9$, —C(=O)NR$_9$R$_9$, —NR$_9$R$_9$, —C(=O)R$_9$, —C(=O)OR$_9$, —OR$_9$, —SR$_9$ or nitro, wherein the alkyl, cycloalkyl, aryl, heteroaryl or heterocyclyl may be optionally substituted with one or more R$_4$'s;

R$_4$, at each occurrence, is independently selected from alkyl, aryl, alkenyl, alkynyl, cycloalkyl, heteroaryl, heterocyclyl, halo, =O, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ or —NR$_9$S(O$_2$)R$_8$, wherein the alkyl, aryl, alkenyl, alkynyl, cycloalkyl, heteroaryl or heterocyclyl may be optionally substituted with one or more R$_5$'s;

R$_5$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ or —NR$_9$S(O$_2$)R$_8$;

R$_8$, at each occurrence, is independently alkyl or aryl;

R$_9$, at each occurrence, is independently hydrogen, alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S;

R$_{9'}$, at each occurrence, is independently alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S;

R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)

$OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_{10}$, $-S(O)_2NR_{14}C(=O)OR_{10}$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})NR_{14}R_{14}$, $-NHC(=NR_{14})NR_{14}R_{14}$, $-S(=O)R_{14}$, $-S(O)_2R_{14}$, $-NR_{14}C(=O)OR_8$, $-NR_{14}S(O_2)R_8$ or arylalkyl;

$R_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_9$, $-S(O)_2NR_{14}C(=O)OR_9$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})NR_{14}R_{14}$, $-NHC(=NR_{14})NR_{14}R_{14}$, $-S(=O)R_{14}$, $-S(O)_2R_{14}$, $-NR_{14}C(=O)OR_8$, $-NR_{14}S(O_2)R_8$ or arylalkyl; and $R_{14}$, at each occurrence, is independently selected from hydrogen, alkyl, cycloalkyl or aryl.

In another embodiment, compounds of formula I are provided wherein:

$R_1$ is a 4- to 7-membered cycloalkyl or heterocyclyl, other than heteroaryl, all of which may be optionally substituted with one or more $R_4$'s;

$R_2$ is halo, cyano, alkyl, alkenyl, alkynyl, cycloalkyl, aryl, heteroaryl, heterocyclyl or $-SO_2R_9$, or wherein the alkyl, alkenyl, alkynyl, cycloalkyl, aryl, heteroaryl or heterocyclyl may be optionally substituted with one or more $R_4$'s;

$R_3$ is halo, cyano, alkyl, cycloalkyl, aryl, heteroaryl, heterocyclyl, $-NR_9C(=O)R_9$, $-NR_9C(=O)OR_{9'}$, $-NR_9C(=O)NR_9R_9$, $-OC(=O)NR_9R_9$, $-C(=O)NR_9R_9$, $-NR_9R_9$, $-C(=O)R_9$, $-C(=O)OR_9$, $-OR_9$, or $-SR_9$, wherein the alkyl, cycloalkyl, aryl, heteroaryl or heterocyclyl may be optionally substituted with one or more $R_4$'s;

$R_4$, at each occurrence, is independently selected from alkyl, aryl, alkenyl, alkynyl, cycloalkyl, heteroaryl, heterocyclyl, halo, $=O$, $-NH_2$, $-CN$, $-NO_2$, $-C(=O)OH$, $-C(=O)OR_{10}$, $-OCF_3$, $-OR_{10}$, $-OH$, $-SH$, $-SR_{10}$, $-S(O)_3H$, $-P(O)_3H_2$, $-C(=O)NR_9R_9$, $-NR_9R_9$, $-S(O)_2NR_9R_9$, $-NR_9S(O)_2CF_3$, $-S(O)_2NR_9C(=O)R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)H$, $-NR_9C(=O)R_{10}$, $-OC(=O)R_{10}$, $-OC(=O)NR_9R_9$, $-C(=NR_{14})NR_9R_9$, $-NHC(=NR_{14})NR_{14}R_{14}$, $-S(=O)R_{10}$, $-S(O)_2R_{10}$, $-NR_9C(=O)OR_8$ or $-NR_9S(O_2)R_8$, wherein the alkyl, aryl, alkenyl, alkynyl, cycloalkyl, heteroaryl or heterocyclyl may be optionally substituted with one or more $R_5$'s;

$R_5$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{10}$, $-OCF_3$, $-OR_{10}$, $-OH$, $-SH$, $-SR_{10}$, $-S(O)_3H$, $-P(O)_3H_2$, $-C(=O)NR_9R_9$, $-NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)R_{10}$, $-C(=O)R_{10}$, $-NR_9C(=O)H$, $-NR_9C(=O)R_{10}$, $-OC(=O)R_{10}$, $-C(=NR_{14})NR_9R_9$, $-NHC(=NR_{14})NR_{14}R_{14}$, $-S(=O)R_{10}$, $-S(O)_2R_{10}$, $-NR_9C(=O)OR_8$ or $-NR_9S(O)_2R_8$;

$R_8$, at each occurrence, is independently alkyl or aryl;

$R_9$, at each occurrence, is independently hydrogen, alkyl, alkoxy, cycloalkyl, aryl, arylalkyl, heteroaryl, heteroarylalkyl, heterocyclyl or heterocyclylalkyl, wherein the heteroaryl, heteroarylalkyl, heterocyclyl or heterocyclylalkyl contain 1-4 heteroatoms selected from N, O, and S;

$R_{9'}$, at each occurrence, is independently alkyl, alkoxy, cycloalkyl, aryl, arylalkyl, heteroaryl, heteroarylalkyl, heterocyclyl or heterocyclylalkyl, wherein the heteroaryl, heteroarylalkyl, heterocyclyl or heterocyclylalkyl contain 1-4 heteroatoms selected from N, O, and S;

$R_{10}$, at each occurrence, is independently selected from alkyl, alkenyl, alkynyl, aryl, arylalkyl, heterocyclyl or heterocyclylalkyl, wherein the heterocyclyl and heterocyclylalkyl contain 1-4 heteroatoms selected from N, O, and S; and $R_{14}$, at each occurrence, is independently selected from hydrogen, alkyl, cycloalkyl or aryl.

In one embodiment, compounds of formula I are provided wherein:

$R_1$ is a 4- to 7-membered cycloalkyl or heterocyclyl, other than heteroaryl, all of which may be optionally substituted with one or more $R_4$'s;

$R_2$ is halo, cyano, alkyl, alkenyl, alkynyl, cycloalkyl, aryl, heteroaryl, or heterocyclyl, wherein the alkyl, alkenyl, alkynyl, cycloalkyl, aryl, heteroaryl or heterocyclyl may be optionally substituted with one or more $R_4$'s;

$R_3$ is halo, alkyl, cycloalkyl, aryl, heteroaryl, heterocyclyl, $-NR_9C(=O)R_9$, $-NR_9C(=O)OR_{9'}$, $-NR_9C(=O)NR_9R_9$, $-OC(=O)NR_9R_9$, $-C(=O)NR_9R_9$, $-NR_9R_9$, $-C(=O)R_9$, $-C(=O)OR_9$, or $-OR_9$, wherein the alkyl, cycloalkyl, aryl, heteroaryl or heterocyclyl may be optionally substituted with one or more $R_4$'s;

$R_4$, at each occurrence, is independently selected from alkyl, aryl, cycloalkyl, heteroaryl, heterocyclyl, halo, $=O$, $-NH_2$, $-CN$, $-NO_2$, $-C(=O)OH$, $-C(=O)OR_{10}$, $-OCF_3$, $-OR_{10}$, $-OH$, $-SH$, $-SR_{10}$, $-C(=O)NR_9R_9$, $-NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)H$, $-NR_9C(=O)R_{10}$, $-OC(=O)R_{10}$, $-S(=O)R_{10}$, $-S(O)_2R_{10}$, $-NR_9C(=O)OR_8$ or $-NR_9S(O_2)R_8$;

$R_8$, at each occurrence, is independently alkyl or aryl;

$R_9$, at each occurrence, is independently hydrogen, alkyl, alkoxy, cycloalkyl, aryl, heteroaryl or heterocyclyl, wherein the heteroaryl or heterocyclyl contain 1-4 heteroatoms selected from N, O, and S; and $R_{10}$, at each occurrence, is independently selected from alkyl, aryl or heterocyclyl, wherein the heterocyclyl contains 1-4 heteroatoms selected from N, O, and S.

In another embodiment, compounds of formula I are provided wherein:

$R_1$ is a 4- to 7-membered cycloalkyl or heterocyclyl, other than heteroaryl, all of which may be optionally substituted with one or more $R_4$'s;

$R_2$ is halo, cyano, alkenyl, alkynyl, cycloalkyl, aryl, heteroaryl or heterocyclyl, wherein the alkenyl, alkynyl, cycloalkyl, aryl, heteroaryl or heterocyclyl may be optionally substituted with one or more $R_4$'s;

$R_3$ is alkyl, cycloalkyl, aryl, heteroaryl, heterocyclyl, $-NR_9C(=O)R_9$, $-NR_9C(=O)OR_9$, $-NR_9C(=O)NR_9R_9$, $-OC(=O)NR_9R_9$, $-C(=O)NR_9R_9$, $-NR_9R_9$, $-C(=O)R_9$, $-C(=O)OR_9$, or $-OR_9$, wherein the alkyl, cycloalkyl, aryl, heteroaryl or heterocyclyl may be optionally substituted with one or more $R_4$'s;

$R_4$, at each occurrence, is independently selected from alkyl, aryl, cycloalkyl, heteroaryl, heterocyclyl, halo, $-NH_2$, $-CN$, $-NO_2$, $-C(=O)OH$, $-C(=O)OR_{10}$, $-OCF_3$, $-OR_{10}$, $-OH$, $-SH$, $-SR_{10}$, $-C(=O)NR_9R_9$, $-NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)H$, $-NR_9C(=O)R_{10}$, $-OC(=O)R_{10}$, $-OC(=O)NR_9R_9$, $-S(=O)R_{10}$ or $-S(O)_2R_{10}$, wherein the alkyl, aryl, cycloalkyl, heteroaryl or heterocyclyl may be optionally substituted with one or more $R_5$'s;

$R_5$, at each occurrence, is independently selected from alkyl, haloalkyl, aryl, cycloalkyl, heteroaryl, heterocyclyl, halo, $-NH_2$, $-CN$, $-NO_2$, $-C(=O)OH$, $-C(=O)OR_{10}$, $-OCF_3$, $-OR_{10}$, $-OH$, $-SH$, $-SR_{10}$, $-C(=O)NR_9R_9$, $-NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)H$, $-NR_9C(=O)R_{10}$, $-OC(=O)R_{10}$, $-S(=O)R_{10}$ or $-S(O)_2R_{10}$;

$R_9$, at each occurrence, is independently hydrogen, alkyl, cycloalkyl, aryl, heteroaryl or heterocyclyl, wherein the heteroaryl or heterocyclyl contain 1-4 heteroatoms selected from N, O, and S; and $R_{10}$, at each occurrence, is independently selected from alkyl, aryl or heterocyclyl, wherein the heterocyclyl contains 1-4 heteroatoms selected from N, O, and S.

In another embodiment, compounds of the present invention are selected from the compounds exemplified in the examples.

In another embodiment, the present invention relates to pharmaceutical compositions comprised of a therapeutically effective amount of a compound of the present invention, alone or, optionally, in combination with a pharmaceutically acceptable carrier and/or one or more other agent(s).

In another embodiment, the present invention relates to methods of inhibiting the activity of the enzyme 11-beta-hydroxysteroid dehydrogenase type I comprising administering to a mammalian patient, for example, a human patient, in need thereof a therapeutically effective amount of a compound of the present invention, alone, or optionally, in combination with another compound of the present invention and/or at least one other type of therapeutic agent.

In another embodiment, the present invention relates to a method for preventing, inhibiting, or treating the progression or onset of diseases or disorders associated with the activity of the enzyme 11-beta-hydroxysteroid dehydrogenase type I comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

Examples of diseases or disorders associated with the activity of the enzyme 11-beta-hydroxysteroid dehydrogenase type I that can be prevented, inhibited, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dislipidemia, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy and glaucoma.

In another embodiment, the present invention relates to a method for preventing, inhibiting, or treating the progression or onset of diabetes, hyperglycemia, obesity, dyslipidemia, hypertension and cognitive impairment comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In still another embodiment, the present invention relates to a method for preventing, inhibiting, or treating the progression or onset of diabetes, comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In yet still another embodiment, the present invention relates to a method for preventing, inhibiting, or treating the progression or onset of hyperglycemia comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of obesity comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In one embodiment, the present invention relates to a method for preventing, inhibiting, or treating the progression or onset of dyslipidemia comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of hypertension comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of cognitive impairment comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of a compound of Formula I may display superior activity compared with the other. Thus, all of the stereochemistries are considered to be a part of the present invention. When required, separation of the racemic material can be achieved by HPLC using a chiral column or by a resolution using a resolving agent such as camphonic chloride as in Steven D. Young, et al, *Antimicrobial Agents and Chemotheraphy*, 1995, 2602-2605.

To the extent that compounds of the formula I, and salts thereof, may exist in their tautomeric form, all such tautomeric forms are contemplated herein as part of the present invention.

The term "substituted," as used herein, means that any one or more hydrogens on the designated atom or ring is replaced with a selection from the indicated group, provided that the designated atom's or ring atom's normal valency is not exceeded, and that the substitution results in a stable compound. When a substituent is keto (i.e., =O), then 2 hydrogens on the atom are replaced.

When any variable (e.g., $R_4$) occurs more than one time in any constituent or formula for a compound, its definition at each occurrence is independent of its definition at every other occurrence. Thus, for example, if a group is shown to be substituted with $(R_4)_m$ and m is 0-3, then said group may optionally be substituted with up to three $R_4$ groups and $R_4$ at each occurrence is selected independently from the definition of $R_4$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio.

Unless otherwise indicated, the term "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio, and/or any of the alkyl substituents set out herein.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl, and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

Unless otherwise indicated, the term "cycloalkyl" as employed herein alone or as part of another group includes saturated or partially unsaturated (containing 1 or 2 double bonds) cyclic hydrocarbon groups containing 1 to 10 rings, preferably 1 to 3 rings, including monocyclic alkyl, bicyclic alkyl (or bicycloalkyl) and tricyclic alkyl, containing a total of 3 to 20 carbons forming the ring, preferably 3 to 15 carbons, more preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl, cyclododecyl, cyclohexenyl,

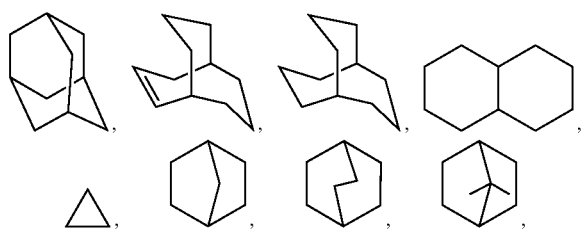

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2v+1)).

Unless otherwise indicated, the term "aryl" as employed herein alone or as part of another group refers to monocyclic and bicyclic aromatic groups containing 6 to 10 carbons in the ring portion (such as phenyl or naphthyl, including 1-naphthyl and 2-naphthyl) and may optionally include 1 to 3 additional rings fused to a carbocyclic ring or a heterocyclic ring (such as aryl, cycloalkyl, heteroaryl, or cycloheteroalkyl rings for example

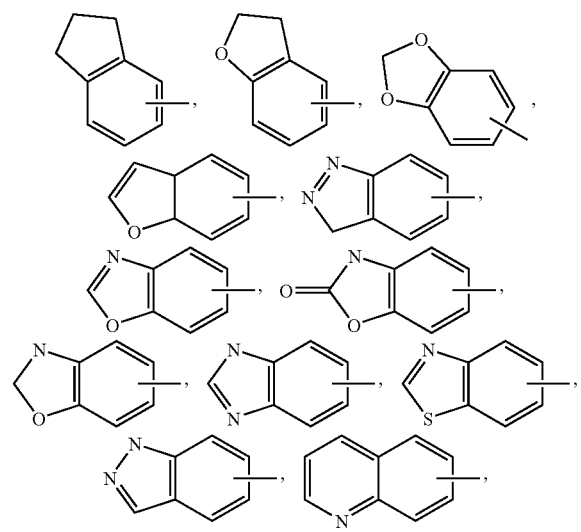

-continued

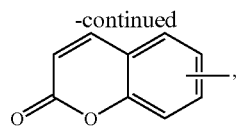

and may be optionally substituted through available carbon atoms with 1, 2, or 3 substituents, for example, hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl, or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino, or arylsulfonaminocarbonyl, and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl, or aryl groups linked to an oxygen atom.

Unless otherwise indicated, the term "amino" as employed herein alone or as part of another group refers to amino that may be substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, or thioalkyl. These substituents may be further substituted with a carboxylic acid and/or any of the $R^1$ groups or substituents for $R^1$ as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl, or hydroxy.

Unless otherwise indicated, the term "lower alkylthio," "alkylthio," "arylthio," or "aralkylthio" as employed herein alone or as part of another group includes any of the above alkyl, aralkyl, or aryl groups linked to a sulfur atom.

Unless otherwise indicated, the term "lower alkylamino," "alkylamino," "arylamino," or "arylalkylamino" as employed herein alone or as part of another group includes any of the above alkyl, aryl, or arylalkyl groups linked to a nitrogen atom.

As used herein, the term "heterocyclyl" or "heterocyclic system" is intended to mean a stable 4- to 14-membered monocyclic, bicyclic or tricyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom, which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S and is aromatic in nature.

Examples of heterocycles include, but are not limited to, 1H-indazole, 2-pyrrolidonyl, 2H,6H-1,5,2-dithiazinyl, 2H-pyrrolyl, 1H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl(benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, the heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoindolyl, piperidinyl, piperidonyl, 4-piperidonyl, piperonyl, pyrazolyl, 1,2,4-triazolyl, 1,2,3-triazolyl, tetrazolyl, thiazolyl, oxazolyl, pyrazinyl, and pyrimidinyl. Also included are fused ring and spiro compounds containing, for example, the above heterocycles.

Examples of heteroaryls are 1H-indazole, 2H,6H-1,5,2-dithiazinyl, indolyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl(benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazo-lidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyrazolotriazinyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, examples of heteroaryls are indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyrazolotriazinyl, pyridazinyl, pyridyl, pyridinyl, pyrimidinyl, pyrrolyl, quinazolinyl, quinolinyl, thiazolyl, thienyl, and tetrazolyl.

The term "heterocyclylalkyl" or "heterocyclyl" as used herein alone or as part of another group refers to heterocyclyl groups as defined above linked through a C atom or heteroatom to an alkyl chain.

The term "heteroarylalkyl" or "heteroarylalkenyl" as used herein alone or as part of another group refers to a heteroaryl group as defined above linked through a C atom or heteroatom to an alkyl chain, alkylene, or alkenylene as defined above.

The term "cyano" as used herein, refers to a —CN group.

The term "nitro" as used herein, refers to an —NO$_2$ group.

The term "hydroxy" as used herein, refers to an OH group.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lacetic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Any compound that can be converted in vivo to provide the bioactive agent (i.e., the compound of formula I) is a prodrug within the scope and spirit of the invention.

The term "prodrugs" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates, and the like.

Various forms of prodrugs are well known in the art and are described in:

a) *The Practice of Medicinal Chemistry,* Camille G. Wermuth et al., Ch. 31, (Academic Press, 1996);

b) *Design of Prodrugs,* edited by H. Bundgaard, (Elsevier, 1985);

c) *A Textbook of Drug Design and Development,* P. Krogsgaard-Larson and H. Bundgaard, eds. Ch. 5, pgs 113-191 (Harwood Academic Publishers, 1991); and d) *Hydrolysis in Drug and Prodrug Metabolism,* Bernard Testa and Joachim M. Mayer, (Wiley-VCH, 2003).

Said references are incorporated herein by reference.

In addition, compounds of the formula I are, subsequent to their preparation, preferably isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

All stereoisomers of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of formula I can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to inhibit MIP-1α or effective to treat or prevent inflammatory disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Synthesis

Compounds of formula I of may be prepared as shown in the following reaction schemes and description thereof, as well as relevant literature procedures that may be used by one skilled in the art. Exemplary reagents and procedures for these reactions appear hereinafter and in the working examples set forth below.

SCHEME I

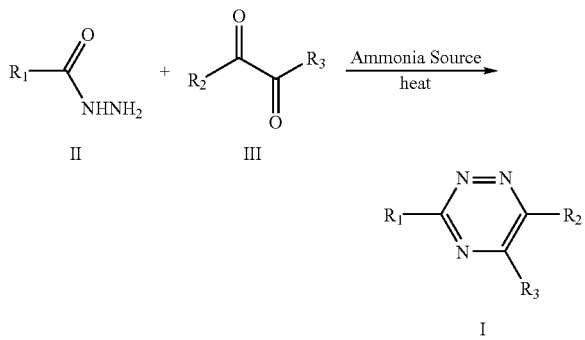

Scheme I describes a method for preparing compounds of formula I. Both, a carbohydrazide intermediate II and a dicarbonyl intermediate III can be obtained commercially, prepared by methods known in the literature or other methods used by one skilled in the art. Formation of compound I can be carried by heating a carbohydrazide intermediate II, a dicarbonyl intermediate III, and an ammonia source, such as ammonium acetate ("NH$_4$OAc"), in a high boiling point solvent, such as glacial acetic acid, bromobenzene or xylene. Alternatively, the reaction can be carried out in a microwave reactor. (*J. Org. Chem.* (2004) 69, pp. 7171-7182. *Tetrahedron. Lett.* (2003) 44, pp. 1123-1127)

SCHEME II

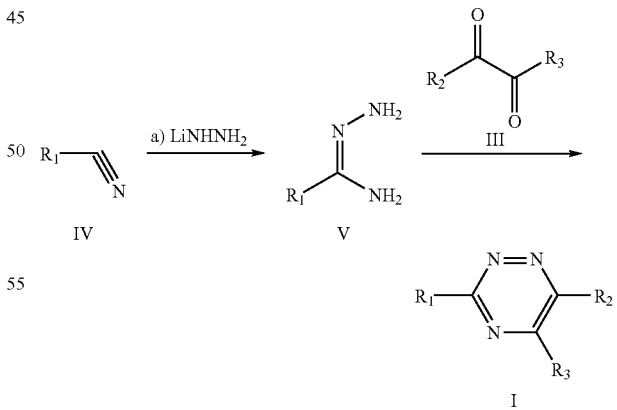

Scheme II describes a method for preparing an amidrazone intermediate V and compounds of formula I. A nitrile intermediate IV can be obtained commercially, prepared by methods known in the literature or by other methods known to one skilled in the art. Formation of an amidrazone intermediate V can be obtained by treating a nitrile intermediate IV with lithium hydrazide ("NH$_2$NH$_2$/n-BuLi"). Subsequent treatment of amidrazone intermediate V with an appropriate dicarbonyl intermediate III in an appropriate solvent, for example, anhydrous ethanol ("EtOH"), provides compounds of formula I. (*J. Org. Chem.* 2004, 69, 7171-7182)

Utilities and Combinations

A. Utilities

The compounds of the present invention possess activity as inhibitors of the enzyme 11-beta-hydroxysteroid dehydrogenase type I, and, therefore, may be used in the treatment of diseases associated with 11-beta-hydroxysteroid dehydrogenase type I activity. Via the inhibition of 11-beta-hydroxysteroid dehydrogenase type I, the compounds of the present invention may preferably be employed to inhibit glucocorticoid, thereby interrupting or modulating cortisone or cortisol production.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, inflammatory diseases and other maladies. Consequently, it is believed that the compounds of the present invention may be used in preventing, inhibiting, or treating diabetes, hyperglycemia, impaired glucose tolerance, insulin resistance, hyperinsulinemia, retinopathy, neuropathy, nephropathy, wound healing, atherosclerosis and its sequelae (acute coronary syndrome, myocardial infarction, angina pectoris, peripheral vascular disease, intermittent claudication, myocardial ischemia, stroke), Metabolic Syndrome, hypertension, obesity, dyslipidemia, hyperlipidemia, hypertriglyceridemia, hypercholesterolemia, low HDL, high LDL, vascular restenosis, lipid disorders, cognitive impairment and dementia, depression, bone disease (including osteoporosis), PCOS, HIV protease associated lipodystrophy, glaucoma and inflammatory diseases, such as, psoriasis, rheumatoid arthritis and osteoarthritis, and treatment of side-effects related to diabetes, lipodistrophy and osteoporosis from corticosteroid treatment.

Metabolic Syndrome or "Syndrome X" is described in Ford, et al., *J. Am. Med. Assoc.* 2002, 287, 356-359 and Arbeeny, et al., *Curr. Med. Chem.—Imm., Endoc. & Metab. Agents* 2001, 1, 1-24.

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with other 11-beta-hydroxysteroid dehydrogenase type I inhibitors or one or more other suitable therapeutic agents useful in the treatment of the aforementioned disorders including: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dislipidemic agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, appetite suppressants, memory enhancing agents, cognition promoting agents and anti-inflammatory agents.

Examples of suitable anti-diabetic agents for use in combination with the compounds of the present invention include insulin and insulin analogs (e.g. LysPro insulin, inhaled formulations comprising insulin); glucagon-like peptides; sulfonylureas and analogs (e.g. chlorpropamide, glibenclamide, tolbutamide, tolazamide, acetohexamide, glypizide, glyburide, glimepiride, repaglinide, meglitinide); biguanides (e.g. metformin, phenformin, buformin); alpha2-antagonists and imidazolines (e.g. midaglizole, isaglidole, deriglidole, idazoxan, efaroxan, fluparoxan); other insulin secretagogues (e.g. linogliride, insulinotropin, exendin-4, BTS-67582, A-4166); thiazolidinediones and PPAR-gamma agonists (e.g. ciglitazone, pioglitazone, troglitazone, rosiglitazone); PPAR-alpha agonists e.g. fenofibrate, gemfibrozil); PPAR alpha/gamma dual agonists (e.g. muraglitazar, peliglitazar); SGLT2 inhibitors (e.g. T-1095 (Tanabe Seiyaku), phlorizin, TS-033 (Taisho), dapagliflozin (BMS), sergliflozin (Kissei), AVE 2268 (Sanofi-Aventis)); dipeptidyl peptidase-IV (DPP4) inhibitors (e.g. saxagliptan, sitagliptan, vildagliptan, and denagliptan); glucagon-like peptide-1 (GLP-1) receptor agonists (e.g. Exenatide (Byetta™), NN2211 (Liraglutide, Novo Nordisk), AVE0010 (Sanofi-Aventis), R1583 (Roche/Ipsen), SUN E7001 (Daiichi/Santory), GSK-716155 (GSK/Human Genome Sciences) and Exendin-4 (PC-DAC™); aldose reductase inhibitors (e.g. those disclosed in WO 99/26659); RXR agonists (e.g. JTT-501, MCC-555, MX-6054, DRF2593, GI-262570, KRP-297, LG100268); fatty acid oxidation inhibitors (e.g. clomoxir, etomoxir; α-glucosidase inhibitors: precose, acarbose, miglitol, emiglitate, voglibose, MDL-25,637, camiglibose, MDL-73,945); beta-agonists (e.g. BRL 35135, BRL 37344, Ro 16-8714, ICI D7114, CL 316,243, TAK-667, AZ40140); phosphodiesterase inhibitors, both cAMP and cGMP type (e.g. sildenafil, L686398: L-386, 398); amylin agonists (e.g. pramlintide, AC-137); lipoxygenase inhibitors (e.g. masoprocal); somatostatin analogs (e.g. BM-23014, seglitide, octreotide); glucagon antagonists (e.g. BAY 276-9955); insulin signaling agonists, insulin mimetics, PTP1B inhibitors (e.g. L-783281, TER17411, TER17529); gluconeogenesis inhibitors (e.g. GP3034); somatostatin analogs and antagonists; antilipolytic agents (e.g. nicotinic acid, acipimox, WAG 994); glucose transport stimulating agents (e.g. BM-130795); glucose synthase kinase inhibitors (e.g. lithium chloride, CT98014, CT98023); galanin receptor agonists; Chemokine receptor antagonist CCR2/5 (e.g. NCB3284, MK-0812, INCB8696, maraviroc (Pfizer) and vicriviroc); thyriod receptor agonists (e.g. KB-2115 (Karo Bio)); Glucokinase activators (e.g. RO-27-4375, RO-28-1675 (Roche), GKA-50 (AstraZeneca)); GPR119 agonists (e.g. PSN-632408 (OSI Prosidion)); GDIR agonists (e.g. APD668 (Arena)).

Examples of suitable lipid lowering agents and anti-atherosclerotic agents for use in combination with the compounds of the present invention include one or more MTP/ApoB secretion inhibitors (e.g. dirlopatide, BMS-201038, CP-741952 (Pfizer), SLx-4090 (Surface Logix)); HMG CoA reductase inhibitors (e.g. atorvastatin, rosuvastatin, simvastatin, pravastatin, lovastatin, fluvastatin); squalene synthetase inhibitors, PPAR alpha agonists and fibric acid derivatives (e.g. fenofibrate, gemfibrozil); ACAT inhibitors; lipoxygenase inhibitors; cholesterol absorption inhibitors (e.g.

ezetimibe); thyriod receptor agonists (e.g. as set forth above); Ileal Na+/bile acid cotransporter inhibitors (e.g. compounds as disclosed in Drugs of the Future, 24, 425-430 (1999); upregulators of LDL receptor activity (e.g. such as MD-700 (Taisho Pharmaceutical Co. Ltd) and LY295427 (Eli Lilly); bile acid sequestrants (e.g. Welchol®, Colestid®, LoCholest® and Questran®; and fibric acid derivatives, such as Atromid® Lopid® and Tricot®); cholesterol ester transfer protein inhibitors (e.g. torcetrapib and (2R)-3-{[3-(4-chloro-3-ethyl-phenoxy)-phenyl]-[[3-(1,1,2,2-tetrafluoroethoxy)phenyl]methyl]amino}-1,1,1-trifluoro-2-propanol); nicotinic acid and derivatives thereof (e.g. niacin, acipimox); PCSK9 inhibitors; LXR agonists (e.g. those disclosed in U.S. Patent Application Publication Nos. 2003/01814206, 2005/0080111, and 2005/0245515); lipoxygenase inhibitors (e.g. such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199-1206, and Cornicelli et al, "15-Lipoxygenase and its Inhibition: A Novel Therapeutic Target for Vascular Disease", Current Pharmaceutical Design, 1999, 5, 11-20).

Preferred hypolipidemic agents are pravastatin, lovastatin, simvastatin, atorvastatin, fluvastatin, cerivastatin, atavastatin, and ZD-4522.

Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetamide, triamtrenene, amiloride, spironolactone), renin inhibitors (e.g., aliskiren), ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan, and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopeptidase inhibitors (dual NEP-ACE inhibitors) (e.g., omapatrilat and gemopatrilat), nitrates, central alpha agonists (e.g. clonidine), alpha1 blockers (e.g. prazosine), arterial vasodilators (e.g. minoxidil), sympatolytics (e.g. resperine), renin inhibitors (e.g. Aliskiren (Novartis)).

Examples of suitable anti-obesity agents for use in combination with the compounds of the present invention include a cannabinoid receptor 1 antagonist or inverse agonist (e.g. rimonabant, SLV 319, CP-945598 (Pfizer), SR-147778 (Sanofi-Aventis), MK0364 (Merck) and those discussed in D. L. Hertzog, Expert Opin. Ther. Patents 2004, 14, 1435-1452); a beta 3 adrenergic agonist (e.g. include AJ9677 (Takeda/Dainippon), L750355 (Merck), or CP331648 (Pfizer,) or other known beta 3 agonists, as disclosed in U.S. Pat. Nos. 5,541,204, 5,770,615, 5,491,134, 5,776,983, and 5,488,064, with AJ9677, L750,355, and CP331648 being preferred); a lipase inhibitor (e.g. orlistat or ATL-962 (Alizyme), with orlistat being preferred); a serotonin (and dopamine) reuptake inhibitor or 5HT2C agonist (e.g. sibutramine, topiramate (Johnson & Johnson), APD-356 (Arena) or axokine (Regeneron), with sibutramine and APD-356 being preferred); MCHR1 receptor antagonists (e.g. GSK-856464 (GlaxoSmithkline), T-0910792 (Amgen)); DGAT inhibitors (e.g. BAY-74-4113 (Bayer)); ACC inhibitors (e.g. A-80040 (Abbott), CP-640186 (Pfizer)), SCD-1 inhibitors as descried by Jiang et al, Diabetes 2004, 53, (abs 653-p); amylin receptor agonists (e.g., compounds disclosed in WO 2005025504); thyroid receptor agonists (e.g. as set forth above); GHSR antagonists (e.g. A-778193 (Abbott), leptin and leptin mimetics (e.g. OB-3 (Aegis/Albany Medical College), leptin analogs A-100 and A-200 (Amgen), CBT-001452 (Cambridge Biotechnology), ML-22952 (Millennium)), PYY receptor agonist (e.g. AC-162352 (Amylin), PYY-3-36 (Emishere), PYY (3-36) NH2 (Unigene)), NPY-5 agonists (e.g. NPY5RA-972 (AstraZeneca), GW-594884A (GlaxoSmithkline), J-104870 (Banyu)); MTP/apoB secretion inhibitors (as set forth above), and/or an anorectic agent.

The anorectic agent which may be optionally employed in combination with compounds of the present invention include dexamphetamine, phentermine, phenylpropanolamine, or mazindol, with dexamphetamine being preferred.

Other compounds that can be used in combination with the compounds of the present invention include CCK receptor agonists (e.g., SR-27895B); galanin receptor antagonists; MCR-4 antagonists (e.g., HP-228); urocortin mimetics, CRF antagonists, and CRF binding proteins (e.g., RU-486, urocortin).

Further, the compounds of the present invention may be used in combination with HIV protease inhibitors, including but not limited to Reyataz®and Kaletra®.

Examples of suitable memory enhancing agents, anti-dementia agents, or cognition promoting agents for use in combination with the compounds of the present invention include, but are not limited to aricept, razadyne, donepezil, rivastigmine, galantamine, memantine, tacrine, metrifonate, muscarine, xanomelline, deprenyl and physostigmine.

Examples of suitable anti-inflammatory agents for use in combination with the compounds of the present invention include, but are not limited to, NSAIDS, prednisone, acetaminophen, aspirin, codeine, fentanyl, ibuprofen, indomethacin, ketorolac, morphine, naproxen, phenacetin, piroxicam, sufentanyl, sunlindac, interferon alpha, prednisolone, methylprednisolone, dexamethazone, flucatisone, betamethasone, hydrocortisone, beclomethasone, remicade, orencia, and enbrel.

The aforementioned patents and patent applications are incorporated herein by reference.

The above other therapeutic agents, when employed in combination with the compounds of the present invention may be used, for example, in those amounts indicated in the Physician's Desk Reference, as in the patents set out above, or as otherwise determined by one of ordinary skill in the art.

The compounds of formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents.

In carrying out the method of the invention for treating diabetes and related diseases, a pharmaceutical composition will be employed containing the compounds of formula I, with or without other antidiabetic agent(s) and/or antihyperlipidemic agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders, and the like. The compounds can be administered to a mammalian patient, including humans, monkeys, dogs, etc. by an oral route, for example, in the form of tablets, capsules, beads, granules or powders. The dose for adults is preferably between 1 and 2,000 mg per day, which can be administered in a single dose or in the form of individual doses from 1-4 times per day.

A typical capsule for oral administration contains compounds of structure I (250 mg), lactose (75 mg), and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

Assay(s) for 11-Beta-Hydroxysteroid Dehydrogenase Activity

The in vitro inhibition of recombinant human 11-beta-HSD1 was determined as follows.

Recombinant human 11-beta-HSD1 was expressed stably in HEK 293 EBNA cells. Cells were grown in DMEM (high glucose) containing MEM non-essential amino acids, L-glutamine, hygromycine B (200 ug/ml), and G418 (200 ug/ml). The cell pellets were homogenized, and the microsomal fraction was obtained by differential centrifugation. 11-beta-HSD1 over expressed microsomes were used as the enzyme source for the Scintillation Proximity Assay (SPA). The test compounds at the desired concentration were incubated at room temperature with 12.5 µg of microsomal enzyme, 250 nM [$^3$H]-cortisone, 500 µM NADPH, 50 mM MES, pH 6.5, and 5 mM EDTA in 96-well OptiPlates. The reaction was terminated with the addition of 1 mM 18β-glycerrhentic acid. SPA reagent mixture (YSi anti-rabbit IgG, anti-cortisol antibody in 50 mM Tris, pH 8.0 containing 1% CHAPS and 1% glycerol) was added and the reaction was further incubated at room temperature over night and counted in TopCount. The $IC_{50}$ (concentration of compound required for 50% inhibition of cortisol formation) was determined using XLfit.

As a means of confirming selectivity for 11-betaHSD1, the compounds of the present invention were also screened for 11-betaHSD2 activity. The in vitro inhibition of recombinant human 11-betaHSD2 was determined as follows:

Recombinant human 11-betaHSD2 was expressed stably in HEK 293 EBNA cells. The microsomal fraction over expressing 11-betaHSD2 was prepared from the cell homogenate. The test compounds at the desired concentration were incubated at 37° C. with 10 µg of microsomal enzyme, 100 nM-cortisol, 1 mM NAD, and 20 mM Tris, pH 7.5 in 96-well plates for 3 h. The reaction was stopped with the addition of equal volume of acetonitrile containing 200 ng/mL triamcinolone (internal standard). The plate was centrifuged and the supernatant was transferred to another 96-well assay plate. Cortisone in the samples was analyzed by LC/MS/MS (Micromass Quattro Ultima Triple Quadrupole Mass Spectrometer). From the MS response (ratio of compound to the internal standard), cortisone formation was calculated using the cortisone standard curve determined on each plate. The $IC_{50}$ (concentration of compound required for 50% inhibition of cortisone formation) was determined using XLfit.

In general, preferred compounds of the present invention, such as particular compounds disclosed in the following examples, have been identified to inhibit the catalytic activity of 11-beta-hydroxysteroid dehydrogenase type I at concentrations equivalent to, or more potently than, 10 µM, preferably 5 µM, more preferably 3 µM, thereby demonstrating compounds of the present invention as especially effective inhibitors of 11-beta-hydroxysteroid dehydrogenase type I. Potencies can be calculated and expressed as either inhibition constants (Ki values) or as $IC_{50}$ values, and refer to activity measured employing the assay system described above.

EXAMPLES

The following working Examples serve to better illustrate, but not limit, some of the preferred embodiments of the present invention.

General

The term HPLC refers to a Shimadzu high performance liquid chromatography with one of following methods.

Method A: YMC or Phenomenex C18 5 micron 4.6×50 mm column using a 4 minute gradient of 0-100% solvent B [90% MeOH:10% H$_2$O:0.2% H$_3$PO$_4$] and 100-0% solvent A [10% MeOH:90% H$_2$O:0.2% H$_3$PO$_4$] with 4 mL/min flow rate and a 1 min. hold, an ultra violet (UV) detector set at 220 nm.

The term prep HPLC refers to an automated Shimadzu HPLC system using a mixture of solvent A (10% MeOH/90% H$_2$O/0.2% TFA) and solvent B (90% MeOH/10% H$_2$O/0.2% TFA). The preparative columns were packed with YMC or Phenomenex ODS C18 5 micron resin or equivalent.

Abbreviations

The following abbreviations are employed in the Examples and elsewhere herein:

EtOAc=ethyl acetate

HOAc or AcOH=acetic acid n-BuLi=n-butyllithium

Na$_2$CO$_3$=sodium carbonate

MgSO$_4$=magnesium sulfate min=minute(s)

h or hr=hour(s)

mL=milliliter mg=milligram(s)

mmol=millimole(s)

RT=room temperature sat or sat'd=saturated aq.=aqueous

HPLC=high performance liquid chromatography

HPLC R$_t$=HPLC retention time

LC/MS=high performance liquid chromatography/mass spectrometry

NMR=nuclear magnetic resonance.

Example 1

3-Adamantan-1-yl-5,6-dimethyl-[1,2,4]triazine

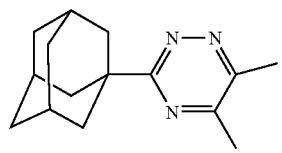

A mixture of admantane-1-carbohydrazide (0.5 mmol), 2,3-butanedione (0.6 mmol) and NH₄OAc (7.5 mmol) in HOAc (glacial, 3 mL) was heated at reflux for 8 h. After this time, the reaction was cooled to room temperature and most of the HOAc was removed in vacuo to yield a residue. The residue was neutralized with sat aq Na₂CO₃ (5 ml) and extracted with EtOAc (3×5 ml). The combined organic layers were dried over MgSO₄, filtered, and concentrated to provide the crude product. The crude product was purified by ISCO flash chromatography to provide Example 1 (45 mg). HPLC R$_f$ (Method A): 3.79 min. LCMS: m/z 244 (M+H$_+$). HPLC purity: 98%. ¹H NMR δ 2.66(s, 3H), 2.53 (s, 3H), 1.90-2.20 (m, 9H), 1.80 (s, 6H).

Example 2

3-Adamantan-1-yl-6,7,8,9-tetrahydro-5H-cyclohepta[1,2,4]triazine

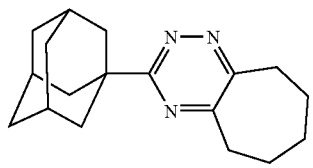

A mixture of admantane-1-carbohydrazide (0.5 mmol), cycloheptane-1,2-dione (0.6 mmol) and NH₄OAc (7.5 mmol) in HOAc (glacial, 3 mL) was heated at 180° C. for 10 min in a microwave reactor. After this time, the reaction mixture was cooled to RT. Once at the prescribed temperature, most of the HOAc was removed in vacuo to yield a residue. The residue was neutralized with saturated aq Na₂CO₃ (5 ml) and extracted with EtOAc (3×5 ml). The combined organic layers were dried over MgSO₄, filtered, and concentrated to provide the crude product. The crude product was purified by ISCO flash chromatography provide Example 2 (58 mg). HPLC RT (Method A): 4.12 min. LCMS: m/z 284 (M+H$_+$). HPLC purity: 98%. ¹H NMR (CDCl₃, 400 MHz) δ 3.19 (t, J=6 Hz, 2H), 2.98 (t, J=6 Hz, 2H), 2.12 (s, 9H), 1.70-1.95 (m, 6H), 1.80 (s, 6H). ¹³C NMR (CDCl₃, 75 MHz) δ 172.6, 164.2, 159.82, 40.7, 39.7, 38.13, 36.6, 35.0, 31.9, 28.4, 26.2, 25.9. EIHRMS (70 eV) m/z 284.2130 ([M+1]⁺, calcd for C₁₈H₂₅N₃ 283.2048.

Examples 3 to 73

Examples 3 to 32 in the following table can be prepared according to the procedures described in Examples 1 or 2, or by other similar methods known to one skilled in the art, with other appropriate reagents.

| Example | Structure | Mass [M + H] (LC/MS) | HPLC purity (%) |
|---|---|---|---|
| 3 | 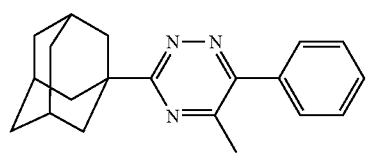 | 306 | >95% |
| 4 | 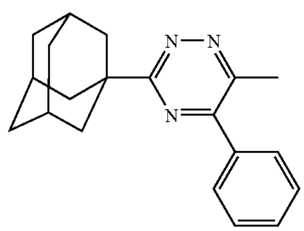 | 306 | >95% |
| 5 | Chiral | 324 | >95% |
| 6 | Chiral | 324 | >95% |

-continued
| Example | Structure | Mass [M + H] (LC/MS) | HPLC purity (%) |
|---|---|---|---|
| 7 | 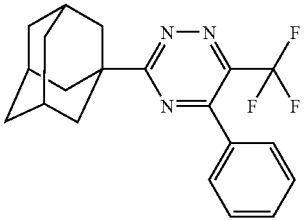 | 360 | >95% |
| 8 | 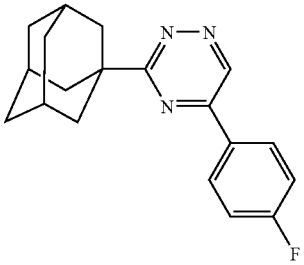 | 310 | >95% |
| 9 | 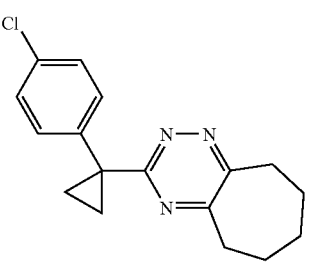 | 300 | >95% |
| 10 | 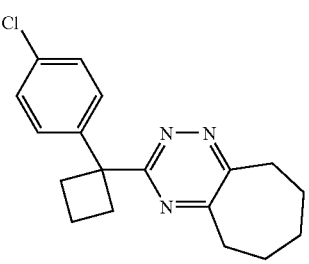 | 314 | >95% |
| 11 | 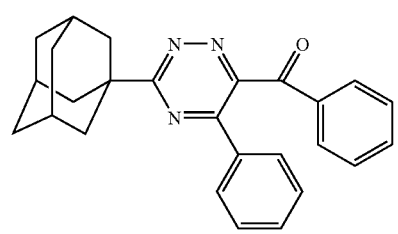 | 396 | >95% |
| 12 | 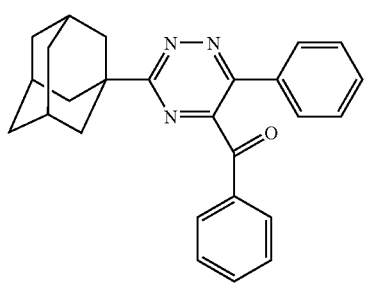 | 396 | >95% |

-continued

| Example | Structure | Mass [M + H] (LC/MS) | HPLC purity (%) |
|---|---|---|---|
| 13 | 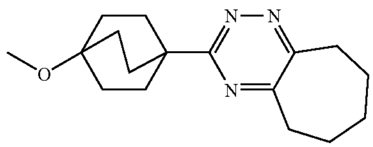 | 288 | >95% |
| 14 | 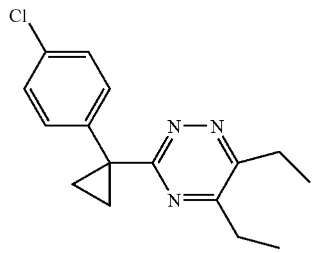 | 288 | >95% |
| 15 | 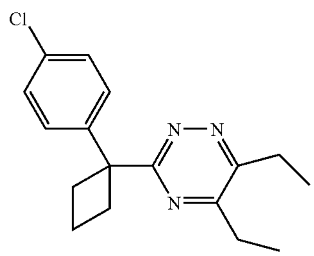 | 302 | >95% |
| 16 | 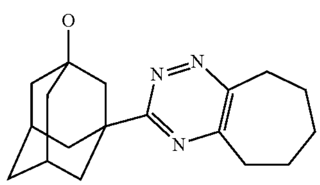 | 300 | >95% |
| 17 | 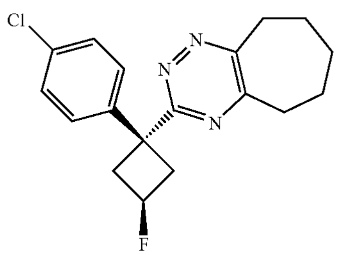 | 332 | >95% |
| 18 | 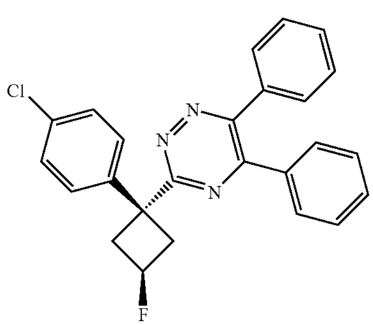 | 416 | >95% |

-continued

| Example | Structure | Mass [M + H] (LC/MS) | HPLC purity (%) |
|---------|-----------|----------------------|-----------------|
| 19 | 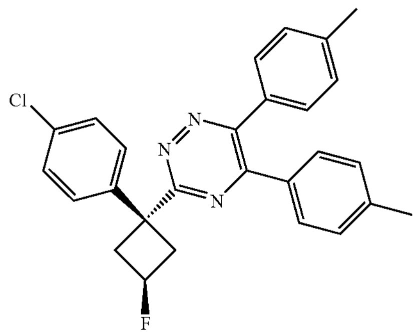 | 444 | >95% |
| 20 | 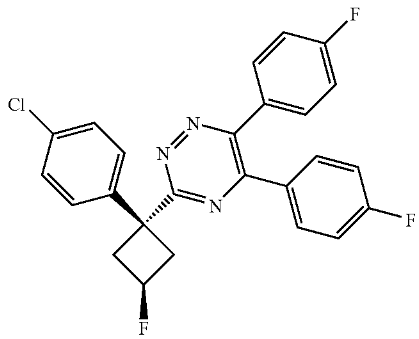 | 452 | >95% |
| 21 | 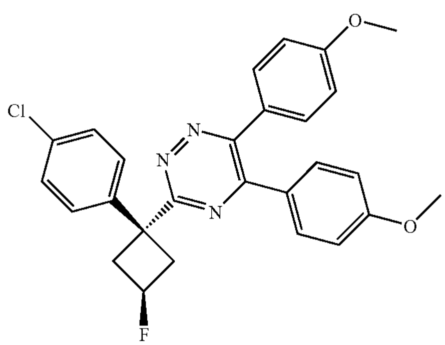 | 476 | >95% |
| 22 | 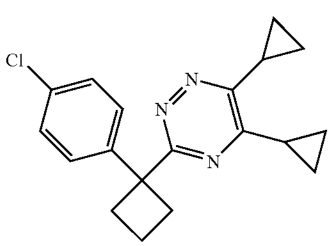 | 326 | >95% |
| 23 | 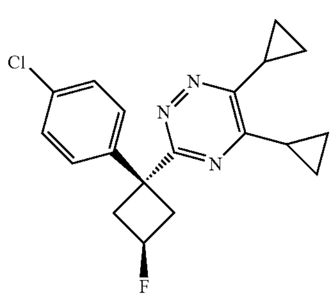 | 344 | >95% |

-continued

| Example | Structure | Mass [M + H] (LC/MS) | HPLC purity (%) |
|---|---|---|---|
| 24 | 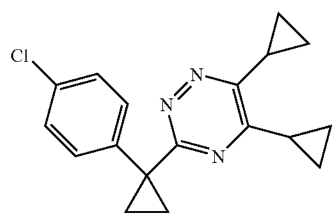 | 312 | >95% |
| 25 | 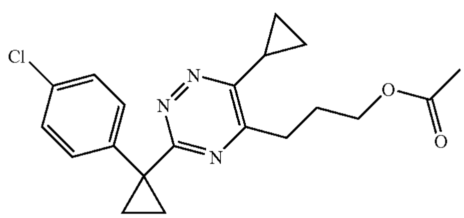 | 372 | >95% |
| 26 | 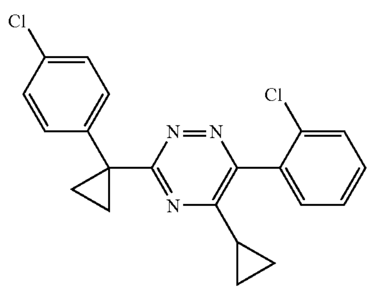 | 382 | >95% |
| 27 | 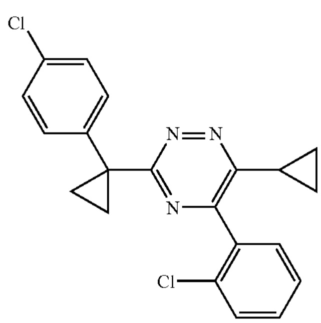 | 382 | >95% |
| 28 | 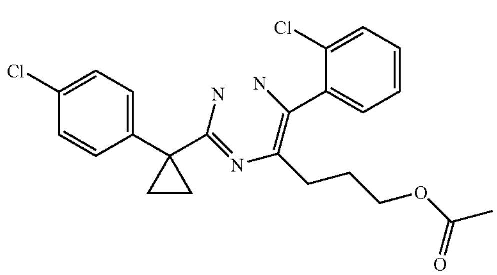 | 442 | >95% |

-continued

| Example | Structure | Mass [M + H] (LC/MS) | HPLC purity (%) |
|---|---|---|---|
| 29 | 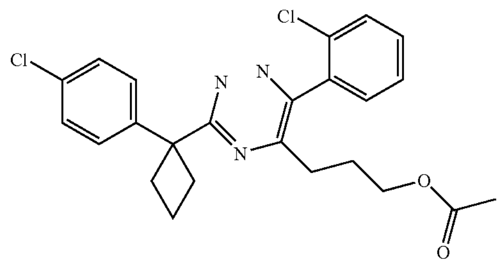 | 456 | >95% |
| 30 | 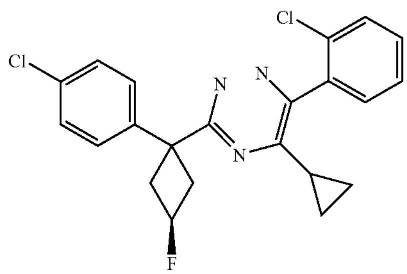 | 415 | >95% |
| 31 | 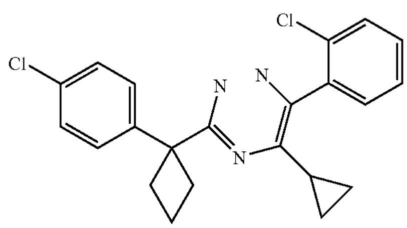 | 397 | >95% |
| 33 | 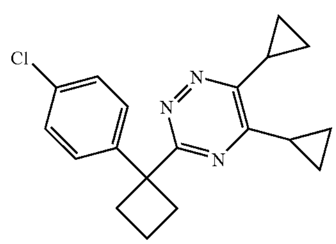 | 326 | >95% |
| 34 | 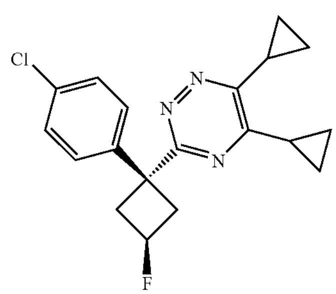 | 344 | >95% |
| 35 | 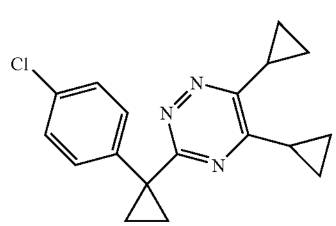 | 312 | >95% |

-continued

| Example | Structure | Mass [M + H] (LC/MS) | HPLC purity (%) |
|---------|-----------|----------------------|-----------------|
| 36 | 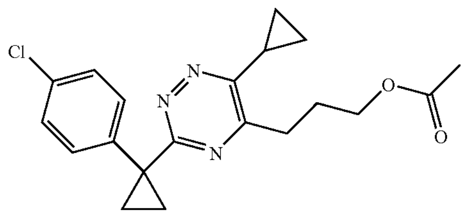 | 372 | >95% |
| 37 | 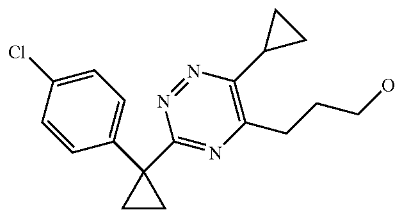 | 330 | >95% |
| 38 | 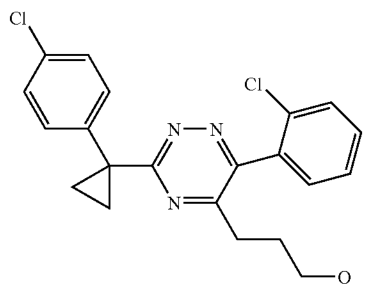 | 400 | >95% |
| 39 | 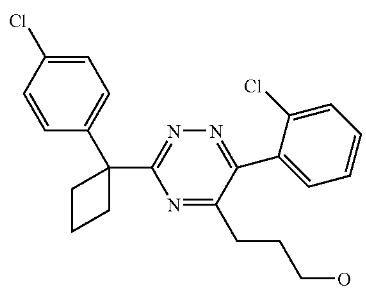 | 414 | >95% |
| 40 | 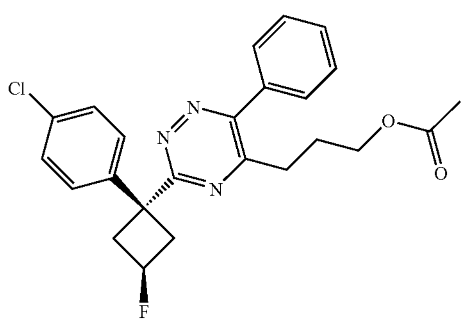 | 474 | >95% |
| 41 | 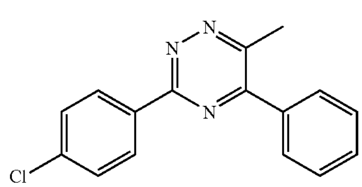 | 282 | >95% |

-continued

| Example | Structure | Mass [M + H] (LC/MS) | HPLC purity (%) |
|---------|-----------|----------------------|-----------------|
| 42 | 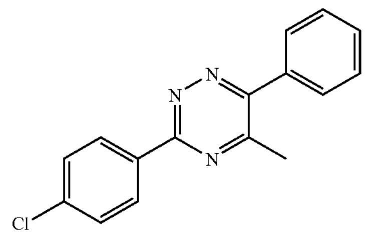 | 282 | >95% |
| 43 | 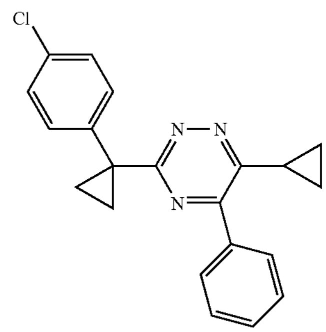 | 348 | >95% |
| 44 | 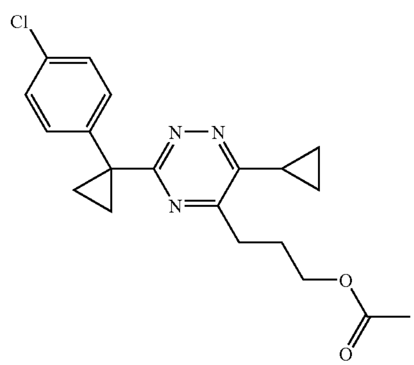 | 408 | >95% |
| 45 | 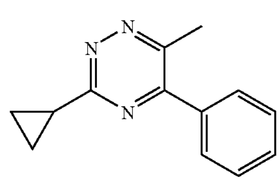 | 212 | >95% |
| 46 | 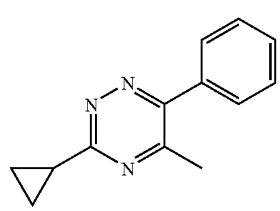 | 212 | >95% |

-continued
| Example | Structure | Mass [M + H] (LC/MS) | HPLC purity (%) |
|---------|-----------|----------------------|-----------------|
| 47 | 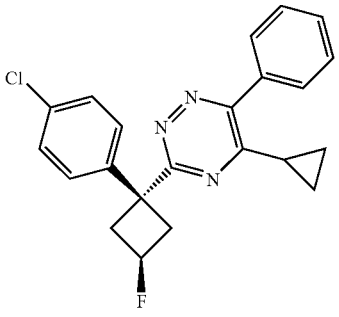 | 380 | >95% |
| 48 | 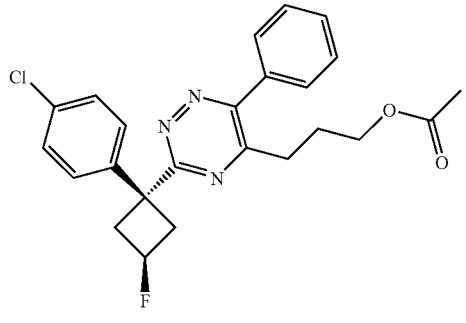 | 440 | >95% |
| 49 | 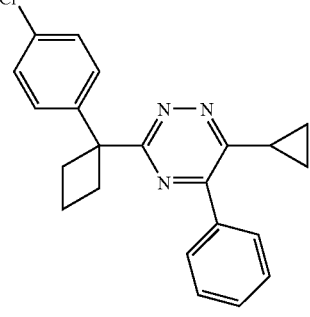 | 362 | >95% |
| 50 | 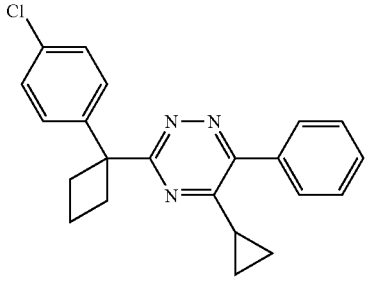 | 362 | >95% |

| Example | Structure | Mass [M + H] (LC/MS) | HPLC purity (%) |
|---|---|---|---|
| 51 | 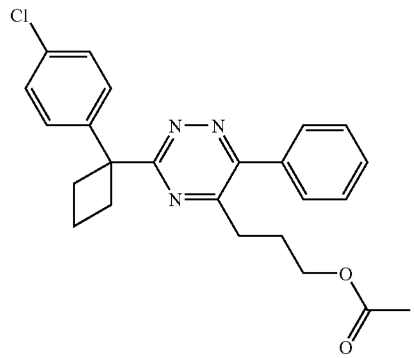 | 422 | >95% |
| 52 | 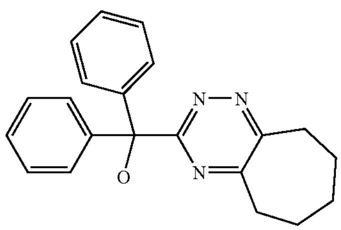 | 332 | >95% |
| 53 | 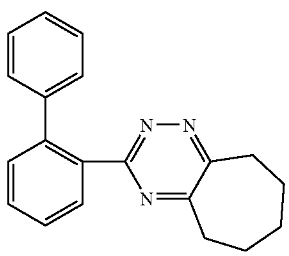 | 302 | >95% |
| 54 | 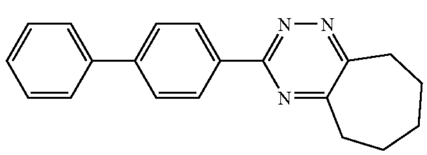 | 302 | >95% |
| 55 | 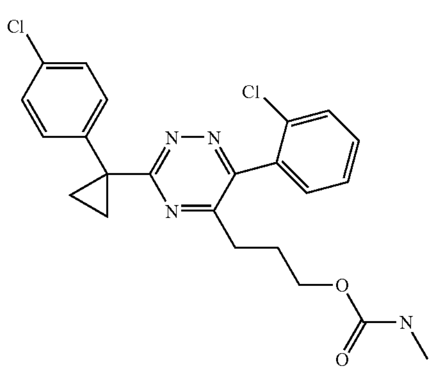 | 457 | >95% |

-continued

| Example | Structure | Mass [M + H] (LC/MS) | HPLC purity (%) |
|---|---|---|---|
| 56 | 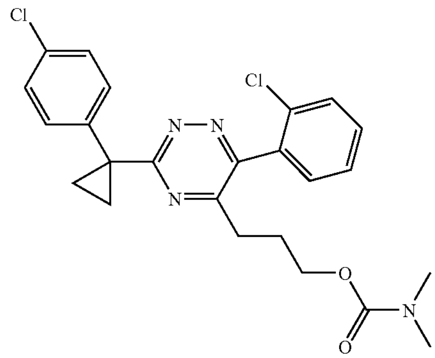 | 471 | >95% |
| 57 | 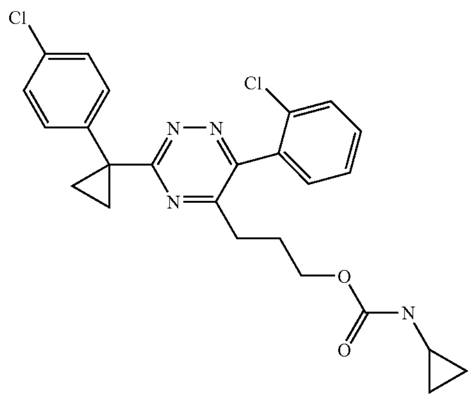 | 483 | >95% |
| 58 | 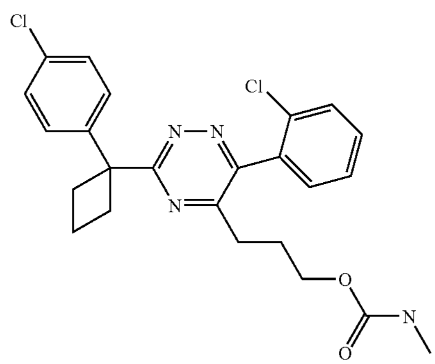 | 471 | >95% |
| 59 | 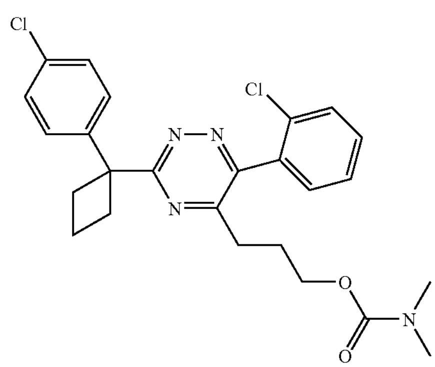 | 485 | >95% |

-continued
| Example | Structure | Mass [M + H] (LC/MS) | HPLC purity (%) |
|---------|-----------|----------------------|-----------------|
| 60 | 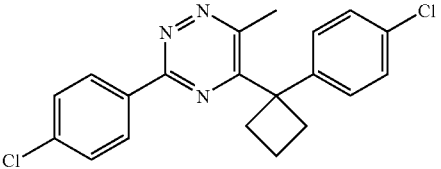 | 370 | >95% |
| 61 | 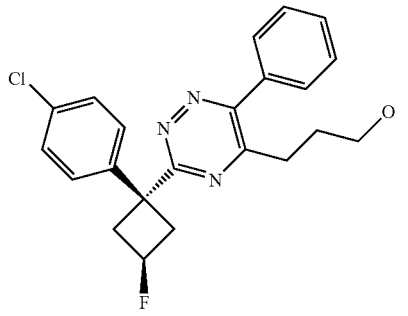 | 398 | >95% |
| 62 | 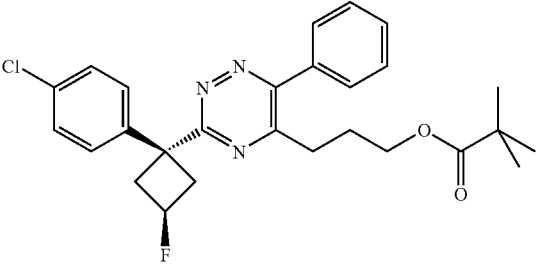 | 482 | >95% |
| 63 | 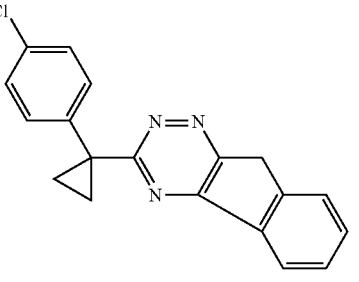 | 320 | >95% |
| 64 | 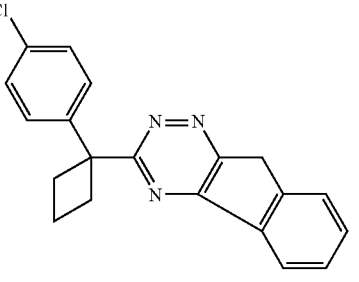 | 334 | >95% |

-continued

| Example | Structure | Mass [M + H] (LC/MS) | HPLC purity (%) |
|---|---|---|---|
| 65 | 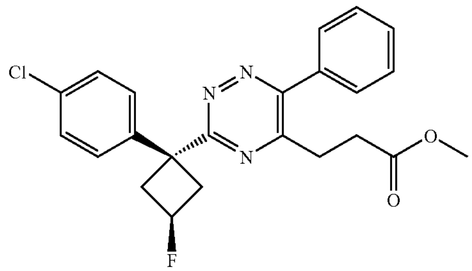 | 426 | >95% |
| 66 | 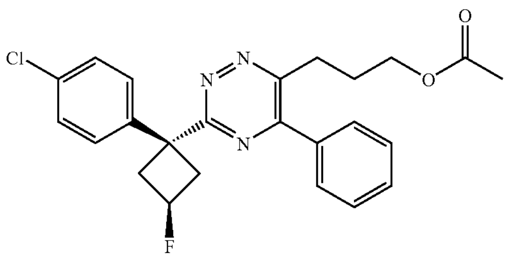 | 440 | >95% |
| 67 | 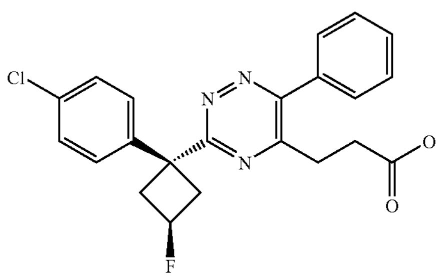 | 412 | >95% |
| 68 | 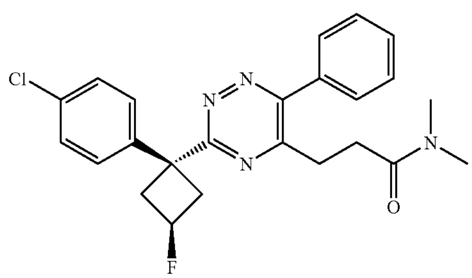 | 439 | >95% |
| 69 | 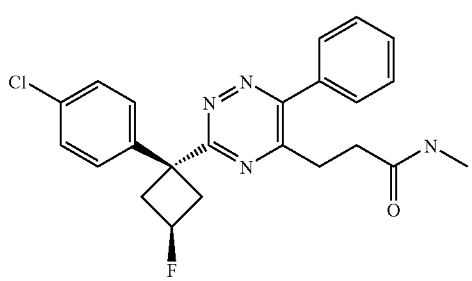 | 425 | >95% |

-continued

| Example | Structure | Mass [M + H] (LC/MS) | HPLC purity (%) |
|---|---|---|---|
| 70 | 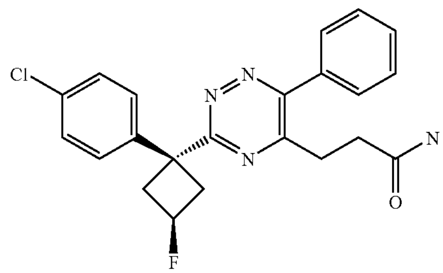 | 411 | >95% |
| 71 | 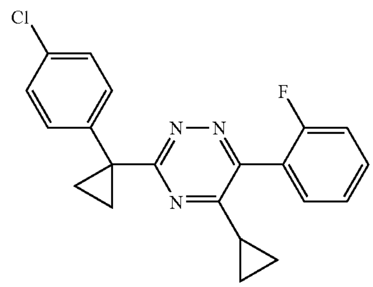 | 366 | >95% |
| 72 | 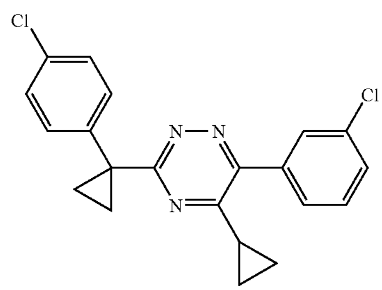 | 382 | >95% |
| 73 | 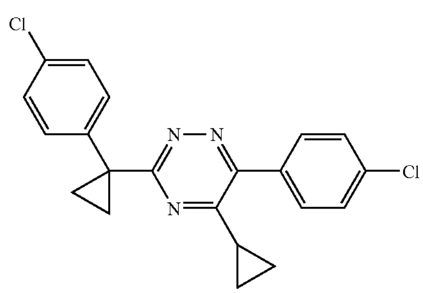 | 382 | >95% |

What is claimed is:
1. A compound of formula (I)

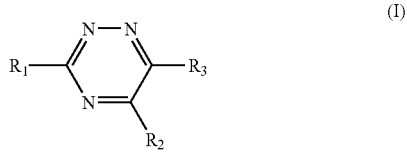

and an enantiomer, diastereomer, and salt thereof wherein:
R$_1$ is cycloalkyl, adamantyl or heterocyclyl, other than heteroaryl, all of which may be optionally substituted with one or more R$_4$'s; provided that: (i) when R$_1$ is heterocyclyl, the heterocylclyl does not attach to the triazine ring via a nitrogen atom; (ii) when R$_1$ is a 3-membered cycloalkyl, R$_4$ is not an optionally substituted indazolyl; and (iii) when R$_1$ is a 3- to 5 membered cycloalkyl and R$_4$ is halo, R$_2$ and R$_3$, together with the carbon atoms to which each is attached, do not form a substituted phenyl or pyridyl ring;

R$_2$ is hydrogen, halo, cyano, alkyl, alkenyl, alkynyl, cycloalkyl, heteroaryl, heterocyclyl, —NR$_9$C(=O)R$_9$, —NR$_9$C(=O)OR$_9'$, —NR$_9$C(=O)NR$_9$R$_9$, —OC(=O)NR$_9$R$_9$, —C(=O)NR$_9$R$_9$, —C(=O)R$_9$, —C(=O)OR$_9$, —SR$_9$, —SO$_2$R$_9'$, —SO$_2$NR$_9$R$_9$, nitro, —OP(=O)(OR$_9$)$_2$ or —NHSO$_2$R$_9'$, wherein the alkyl, alkenyl, alkynyl, cycloalkyl, heteroaryl or heterocyclyl may be optionally substituted with one or more $R_4$'s; provided that $R_2$ cannot be a 5- or 6- membered substituted heteroaryl;

$R_3$ is halo, cyano, alkyl, alkenyl, alkynyl, cycloalkyl, heteroaryl, heterocyclyl, $-NR_9C(=O)R_9$, $-NR_9C(=O)OR_{9'}$, $-NR_9C(=O)NR_9R_9$, $-OC(=O)NR_9R_9$, $-C(=O)NR_9R_9$, $-NR_9R_9$, $-C(=O)R_9$, $-C(=O)OR_9$, $-SR_9$, $-SO_2R_9$, $-SO_2NR_9R_9$, nitro, $-OP(=O)(OR_9)_2$ or $-NHSO_2R_{9'}$, wherein the alkyl, alkenyl, alkynyl, cycloalkyl, heteroaryl or heterocyclyl may be optionally substituted with one or more $R_4$'s; provided that $R_3$ cannot be a 6- membered substituted heteroaryl; or $R_2$ and $R_3$ are taken together with the carbon atoms to which each is attached to form a 4- to 15-membered mono-, bi- or tricylic ring, wherein said ring may be optionally substituted with one or more $R_4$'s; or $R_2$ and $R_3$ are taken together with the carbon atoms to which each is attached to form a 4- to 15-membered mono-, bi- or tricylic heterocyclyl ring wherein the heterocyclyl ring contains 1-4 heteroatoms selected from N, O, and S, and said ring may be optionally substituted with one or more $R_4$'s; provided that said ring cannot be a pyrimidinedionyl ring;

$R_4$, at each occurrence, is independently selected from alkyl, aryl, alkenyl, alkynyl, cycloalkyl, heteroaryl, heterocyclyl, halo, $=O$, $-NH_2$, $-CN$, $-NO_2$, $-C(=O)OH$, $-C(=O)OR_{10}$, $-OCF_3$, $-OR_{10}$, $-OH$, $-SH$, $-SR_{10}$, $-S(O)_3H$, $-P(O)_3H_2$, $-C(=O)NR_9R_9$, $-NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)H$, $-NR_9C(=O)R_{10}$, $-OC(=O)R_{10}$, $-OC(=O)NR_9R_9$, $-C(=NR_{14})NR_9R_9$, $-NHC(=NR_{14})NR_{14}R_{14}$, $-S(=O)R_{10}$, $-S(O)_2R_{10}$, $-NR_9C(=O)OR_8$ or $-NR_9S(O_2)R_8$, wherein the alkyl, aryl, alkenyl, alkynyl, cycloalkyl, heteroaryl or heterocyclyl maybe optionally substituted with one or more $R_5$'s;

$R_5$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{10}$, $-OCF_3$, $-OR_{10}$, $-OH$, $-SH$, $-SR_{10}$, $-S(O)_3H$, $-P(O)_3H_2$, $-C(=O)NR_9R_9$, $-NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)H$, $-NR_9C(=O)R_{10}$, $-OC(=O)R_{10}$, $-C(=NR_{14})NR_9R_9$, $-NHC(=NR_{14})NR_{14}R_{14}$, $-S(=O)R_{10}$, $-S(O)_2R_{10}$, $-NR_9C(=O)OR_8$ or $-NR_9S(O_2)R_8$;

$R_8$, at each occurrence, is independently alkyl or aryl;

$R_9$, at each occurrence, is independently hydrogen, alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S;

$R_{9'}$, at each occurrence, is independently alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_{10}$, $-S(O)_2NR_{14}C(=O)OR_{10}$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})NR_{14}R_{14}$, $-NHC(=NR_{14})NR_{14}R_{14}$, $-S(=O)R_{14}$, $-S(O)_2R_{14}$, $-NR_{14}C(=O)OR_8$, $-NR_{14}S(O_2)R_8$ or arylalkyl;

$R_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 $R_{10a}$, and the heterocyclyl and heterocylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_9$, $-S(O)_2NR_{14}C(=O)OR_9$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})NR_{14}R_{14}$, $-NHC(=NR_{14})NR_{14}R_{14}$, $-S(=O)R_{14}$, $-S(O)_2R_{14}$, $-NR_{14}C(=O)OR_8$, $-NR_{14}S(O_2)R_8$ or arylalkyl; and $R_{14}$, at each occurrence, is independently selected from hydrogen, alkyl, cycloalkyl or aryl.

2. The compound of claim 1, wherein:

$R_1$ is adamantyl, a 3-membered cycloalkyl or an 8- to 20-membered cycloalkyl, other than adamantyl, all of which may be optionally substituted with one or more $R_4$'s;

$R_2$ is hydrogen, halo, cyano, alkyl, alkenyl, alkynyl, cycloalkyl, heteroaryl, heterocyclyl, $-NR_9C(=O)R_9$, $-NR_9C(=O)OR_{9'}$, $-NR_9C(=O)NR_9R_9$, $-OC(=O)NR_9R_9$, $-C(=O)NR_9R_9$, $-C(=O)R_9$, $-C(=O)OR_9$, $-SR_9$, $-SO_2R_{9'}$, $-SO_2NR_9R_9$, nitro, $-OP(=O)(OR_9)_2$ or $-NHSO_2R_{9'}$, wherein the alkyl, alkenyl, alkynyl, cycloalkyl, heteroaryl or heterocyclyl may be optionally substituted with one or more $R_4$'s;

$R_3$ is halo, cyano, alkyl, alkenyl, alkynyl, cycloalkyl, heteroaryl, heterocyclyl, $-NR_9C(=O)R_9$, $-NR_9C(=O)OR_{9'}$, $-NR_9C(=O)NR_9R_9$, $-OC(=O)NR_9R_9$, $-C(=O)NR_9R_9$, $-NR_9R_9$, $-C(=O)R_9$, $-C(=O)OR_9$, $-SR_9$, $-SO_2R_{9'}$, $-SO_2NR_9R_9$, nitro, $-OP(=O)(OR_9)_2$ or $-NHSO_2R_{9'}$, wherein the alkyl, alkenyl, alkynyl, cycloalkyl, heteroaryl or heterocyclyl may be optionally substituted with one or more $R_4$'s; or $R_2$ and $R_3$ are taken together with the carbon atoms to which each is attached to form a 4- to 15-membered mono-, bi- or tricylic ring, wherein said ring may be optionally substituted with one or more $R_4$'s; or $R_2$ and $R_3$ are taken together with the carbon atoms to which each is attached to form a 4- to 15-membered mono-, bi- or tricylic heterocyclyl ring wherein the heterocyclyl ring contains 1-4 heteroatoms selected from N, O, and S, and said ring may be optionally substituted with one or more $R_4$'s;

$R_4$, at each occurrence, is independently selected from alkyl, aryl, alkenyl, alkynyl, cycloalkyl, heteroaryl, heterocyclyl, halo, =O, —$NH_2$, —CN, —$NO_2$, —C(=O)OH, —C(=O)$OR_{10}$, —$OCF_3$, —$OR_{10}$, —OH, —SH, —$SR_{10}$, —$S(O)_3H$, —$P(O)_3H_2$, —C(=O)$NR_9R_9$, —$NR_9R_9$, —$S(O)_2NR_9R_9$, —$NR_9S(O)_2CF_3$, —C(=O)$NR_9S(O)_2R_9$, —$S(O)_2NR_9C$(=O)$OR_9$, —$S(O)_2NR_9C$(=O)$NR_9R_9$, —C(=O)$NR_9S(O)_2CF_3$, —C(=O)$R_{10}$, —$NR_9C$(=O)H, —$NR_9C$(=O)$R_{10}$, —OC(=O)$R_{10}$, —OC(=O)$NR_9R_9$, —C(=$NR_{14}$)$NR_9R_9$, —NHC(=$NR_{14}$)$NR_{14}R_{14}$, —S(=O)$R_{10}$, —$S(O)_2R_{10}$, —$NR_9C$(=O)$OR_8$ or —$NR_9S(O_2)R_8$, wherein the alkyl, aryl, alkenyl, alkynyl, cycloalkyl, heteroaryl or heterocyclyl may be optionally substituted with one or more $R_5$'s;

$R_5$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —C(=O)OH, —C(=O)$OR_{10}$, —$OCF_3$, —$OR_{10}$, —OH, —SH, —$SR_{10}$, —$S(O)_3H$, —$P(O)_3H_2$, —C(=O)$NR_9R_9$, —$NR_9R_9$, —$S(O)_2NR_9R_9$, —$NR_9S(O)_2CF_3$, —C(=O)$NR_9S(O)_2R_9$, —$S(O)_2NR_9C$(=O)$OR_9$, —$S(O)_2NR_9C$(=O)$NR_9R_9$, —C(=O)$NR_9S(O)_2CF_3$, —C(=O)$R_{10}$, —$NR_9C$(=O)H, —$NR_9C$(=O)$R_{10}$, —OC(=O)$R_{10}$, —C(=$NR_{14}$)$NR_9R_9$, —NHC(=$NR_{14}$)$NR_{14}R_{14}$, —S(=O)$R_{10}$, —$S(O)_2R_{10}$, —$NR_9C$(=O)$OR_8$ or —$NR_9S(O_2)R_8$;

$R_8$, at each occurrence, is independently alkyl or aryl;

$R_9$, at each occurrence, is independently hydrogen, alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S;

$R_{9'}$, at each occurrence, is independently alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —C(=O)OH, —C(=O)$OR_{14}$, —$OCF_3$, —$OR_{14}$, —OH, —SH, —$SR_{14}$, —$S(O)_3H$, —$P(O)_3H_2$, —C(=O)$NR_{14}R_{14}$, —$NR_{14}R_{14}$, —$S(O)_2NR_{14}R_{14}$, —$NR_{14}S(O)_2CF_3$, —C(=O)$NR_{14}S(O)_2R_{10}$, —$S(O)_2NR_{14}C$(=O)$OR_{10}$, —$S(O)_2NR_{14}C$(=O)$NR_{14}R_{14}$, —C(=O)$NR_{14}S(O)_2CF_3$, —C(=O)$R_{14}$, —$NR_{14}C$(=O)H, —$NR_{14}C$(=O)$R_{14}$, —OC(=O)$R_{14}$, —C(=$NR_{14}$)$NR_{14}R_{14}$, —NHC(=$NR_{14}$)$NR_{14}R_{14}$, —S(=O)$R_{14}$, —$S(O)_2R_{14}$, —$NR_{14}C$(=O)$OR_8$, —$NR_{14}S(O_2)R_8$ or arylalkyl;

$R_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —C(=O)OH, —C(=O)$OR_{14}$, —$OCF_3$, —$OR_{14}$, —OH, —SH, —$SR_{14}$, —$S(O)_3H$, —$P(O)_3H_2$, —C(=O)$NR_{14}R_{14}$, —$NR_{14}R_{14}$, —$S(O)_2NR_{14}R_{14}$, —$NR_{14}S(O)_2CF_3$, —C(=O)$NR_{14}S(O)_2R_9$, —$S(O)_2NR_{14}C$(=O)$OR_9$, —$S(O)_2NR_{14}C$(=O)$NR_{14}R_{14}$, —C(=O)$NR_{14}S(O)_2CF_3$, —C(=O)$R_{14}$, —$NR_{14}C$(=O)H, —$NR_{14}C$(=O)$R_{14}$, —OC(=O)$R_{14}$, —C(=$NR_{14}$)$NR_{14}R_{14}$, —NHC(=$NR_{14}$)$NR_{14}R_{14}$, —S(=O)$R_{14}$, —$S(O)_2R_{14}$, —$NR_{14}C$(=O)$OR_8$, —$NR_{14}S(O_2)R_8$ or arylalkyl; and $R_{14}$, at each occurrence, is independently selected from hydrogen, alkyl, cycloalkyl or aryl.

3. The compound of claim 1, wherein:

$R_1$ is adamantyl, a 3-membered cycloalkyl or an 8- to 15-membered cycloalkyl, other than adamantyl, all of which may be optionally substituted with one or more $R_4$'s;

$R_2$ is hydrogen, halo, cyano, alkyl, alkenyl, alkynyl, cycloalkyl, heteroaryl, heterocyclyl, —$NR_9C$(=O)$R_9$, —$NR_9C$(=O)$OR_{9'}$, —$NR_9C$(=O)$NR_9R_9$, —OC(=O)$NR_9R_9$, —C(=O)$NR_9R_9$, —C(=O)$R_9$, —C(=O)$OR_9$, —$SR_9$, —$SO_2R_{9'}$, —$SO_2NR_9R_9$, nitro, —OP(=O)($OR_9$)$_2$ or —$NHSO_2R_{9'}$, wherein the alkyl, alkenyl, alkynyl, cycloalkyl, heteroaryl or heterocyclyl may be optionally substituted with one or more $R_4$'s;

$R_3$ is halo, cyano, alkyl, alkenyl, alkynyl, cycloalkyl, heteroaryl, heterocyclyl, —$NR_9C$(=O)$R_9$, —$NR_9C$(=O)$OR_{9'}$, —$NR_9C$(=O)$NR_9R_9$, —OC(=O)$NR_9R_9$, —C(=O)$NR_9R_9$, —$NR_9R_9$, —C(=O)$R_9$, —C(=O)$OR_9$, —$SR_9$, —$SO_2R_{9'}$, —$SO_2NR_9R_9$, nitro, —OP(=O)($OR_9$)$_2$ or —$NHSO_2R_{9'}$, wherein the alkyl, alkenyl, alkynyl, cycloalkyl, heteroaryl or heterocyclyl may be optionally substituted with one or more $R_4$'s; or $R_2$ and $R_3$ are taken together with the carbon atoms to which each is attached to form a 4- to 15-membered mono-, bi- or tricylic ring, wherein said ring may be optionally substituted with one or more $R_4$'s; or $R_4$, at each occurrence, is independently selected from alkyl, aryl, alkenyl, alkynyl, cycloalkyl, heteroaryl, heterocyclyl, halo, =O, —$NH_2$, —CN, —$NO_2$, —C(=O)OH, —C(=O)$OR_{10}$, —$OCF_3$, —$OR_{10}$, —OH, —SH, —$SR_{10}$, —$S(O)_3H$, —$P(O)_3H_2$, —C(=O)$NR_9R_9$, —$NR_9R_9$, —$S(O)_2NR_9R_9$, —$NR_9S(O)_2CF_3$, —C(=O)$NR_9S(O)_2R_9$, —$S(O)_2NR_9C$(=O)$OR_9$, —$S(O)_2NR_9C$(=O)$NR_9R_9$, —C(=O)$NR_9S(O)_2CF_3$, —C(=O)$R_{10}$, —$NR_9C$(=O)H, —$NR_9C$(=O)$R_{10}$, —OC(=O)$R_{10}$, —OC(=O)$NR_9R_9$, —C(=$NR_{14}$)$NR_9R_9$, —NHC(=$NR_{14}$)$NR_{14}R_{14}$, —S(=O)$R_{10}$, —$S(O)_2R_{10}$, —$NR_9C$(=O)$OR_8$ or —$NR_9S(O_2)R_8$, wherein the alkyl, aryl, alkenyl, alkynyl, cycloalkyl, heteroaryl or heterocyclyl may be optionally substituted with one or more $R_5$'s;

$R_5$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —C(=O)OH, —C(=O)$OR_{10}$, —$OCF_3$, —$OR_{10}$, —OH, —SH, —$SR_{10}$, —$S(O)_3H$, —$P(O)_3H_2$, —C(=O)$NR_9R_9$, —$NR_9R_9$, —$S(O)_2NR_9R_9$, —$NR_9S(O)_2CF_3$, —C(=O)$NR_9S(O)_2R_9$, —$S(O)_2NR_9C$(=O)$OR_9$, —$S(O)_2NR_9C$(=O)$NR_9R_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ or —NR$_9$S(O$_2$)R$_8$;

R$_8$, at each occurrence, is independently alkyl or aryl;

R$_9$, at each occurrence, is independently hydrogen, alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S;

R$_{9'}$, at each occurrence, is independently alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S;

R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl;

R$_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 R$_{10a}$, and the heterocyclyl and heterocyclylalkyl contain 1-4 heteroatoms selected from N, O, and S;

R$_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl; and R$_{14}$, at each occurrence, is independently selected from hydrogen, alkyl, cycloalkyl or aryl.

4. The compound of claim 1, wherein:

R$_1$ is adamantyl, a 3-membered cycloalkyl or an 8- to 15-membered cycloalkyl, other than adamantyl, all of which may be optionally substituted with one or more R$_4$'s;

R$_2$ is hydrogen, halo, cyano, alkyl, cycloalkyl, heteroaryl, heterocyclyl, —NR$_9$C(=O)R$_9$, —NR$_9$C(=O)OR$_{9'}$, —NR$_9$C(=O)NR$_9$R$_9$, —OC(=O)NR$_9$R$_9$, —C(=O)NR$_9$R$_9$, —C(=O)R$_9$, —C(=O)OR$_9$, —SR$_9$ or nitro, wherein the alkyl, cycloalkyl, heteroaryl or heterocyclyl may be optionally substituted with one or more R$_4$'s;

R$_3$ is halo, cyano, alkyl, cycloalkyl, heteroaryl, heterocyclyl, —NR$_9$C(=O)R$_9$, —NR$_9$C(=O)OR$_{9'}$, —NR$_9$C(=O)NR$_9$R$_9$, —OC(=O)NR$_9$R$_9$, —C(=O)NR$_9$R$_9$, —NR$_9$R$_9$, —C(=O)R$_9$, —C(=O)OR$_9$, —SR$_9$ or nitro, wherein the alkyl, cycloalkyl, heteroaryl or heterocyclyl may be optionally substituted with one or more R$_4$'s; or R$_2$ and R$_3$ are taken together with the carbon atoms to which each is attached to form a 4- to 15-membered mono-, bi- or tricylic ring, wherein said ring may be optionally substituted with one or more R$_4$'s;

R$_4$, at each occurrence, is independently selected from alkyl, aryl, alkenyl, alkynyl, cycloalkyl, heteroaryl, heterocyclyl, halo, =O, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ or —NR$_9$S(O$_2$)R$_8$, wherein the alkyl, aryl, alkenyl, alkynyl, cycloalkyl, heteroaryl or heterocyclyl may be optionally substituted with one or more R$_5$'s;

R$_5$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ or —NR$_9$S(O$_2$)R$_8$;

R$_8$, at each occurrence, is independently alkyl or aryl;

R$_9$, at each occurrence, is independently hydrogen, alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S;

R$_{9'}$, at each occurrence, is independently alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S;

R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl;

R$_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 R$_{10a}$, and the heterocyclyl and heterocyclylalkyl contain 1-4 heteroatoms selected from N, O, and S;

R$_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl; and R$_{14}$, at each occurrence, is independently selected from hydrogen, alkyl, cycloalkyl or aryl.

5. The compound of claim 1, wherein:

R$_1$ is adamantyl, a 3-membered cycloalkyl or an 8- to 15-membered cycloalkyl, other than adamantyl, all of which may be optionally substituted with one or more R$_4$'s;

R$_2$ is halo, cyano, alkyl, cycloalkyl, heteroaryl, heterocyclyl, —NR$_9$C(=O)R$_9$, —NR$_9$C(=O)OR$_9$, —NR$_9$C(=O)NR$_9$R$_9$, —OC(=O)NR$_9$R$_9$, —C(=O)NR$_9$R$_9$, —C(=O)R$_9$, —C(=O)OR$_9$, —SR$_9$ or nitro, wherein the alkyl, cycloalkyl, heteroaryl or heterocyclyl may be optionally substituted with one or more R$_4$'s;

R$_3$ is halo, cyano, alkyl, cycloalkyl, heteroaryl, heterocyclyl, —NR$_9$C(=O)R$_9$, —NR$_9$C(=O)OR$_9$, —NR$_9$C(=O)NR$_9$R$_9$, —OC(=O)NR$_9$R$_9$, —C(=O)NR$_9$R$_9$, —NR$_9$R$_9$, —C(=O)R$_9$, —C(=O)OR$_9$, —SR$_9$ or nitro, wherein the alkyl, cycloalkyl, heteroaryl or heterocyclyl may be optionally substituted with one or more R$_4$'s; or R$_2$ and R$_3$ are taken together with the carbon atoms to which each is attached to form a 4- to 15-membered mono-, bi- or tricylic ring, wherein said ring may be optionally substituted with one or more R$_4$'s;

R$_4$, at each occurrence, is independently selected from alkyl, aryl, alkenyl, alkynyl, cycloalkyl, heteroaryl, heterocyclyl, halo, =O, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ or —NR$_9$S(O$_2$)R$_8$, wherein the alkyl, aryl, alkenyl, alkynyl, cycloalkyl, heteroaryl or heterocyclyl may be optionally substituted with one or more R$_5$'s;

R$_5$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ or —NR$_9$S(O$_2$)R$_8$;

R$_8$, at each occurrence, is independently alkyl or aryl;

R$_9$, at each occurrence, is independently hydrogen, alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S;

R$_{9'}$, at each occurrence, is independently alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S;

R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl;

R$_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 R$_{10a}$, and the heterocyclyl and heterocyclylalkyl contain 1-4 heteroatoms selected from N, O, and S;

R$_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl; and R$_{14}$, at each occurrence, is independently selected from hydrogen, alkyl, cycloalkyl or aryl.

6. The compound of claim 1, wherein:

R$_1$ is adamantyl, a 3-membered cycloalkyl or an 8- to 15-membered cycloalkyl, other than adamantyl, all of which may be optionally substituted with one or more R$_4$'s;

$R_2$ is halo, cyano, alkyl, cycloalkyl, heteroaryl, heterocyclyl, —NR$_9$C(=O)R$_9$, —NR$_9$C(=O)OR$_9$, —NR$_9$C(=O)NR$_9$R$_9$, —OC(=O)NR$_9$R$_9$, —C(=O)NR$_9$R$_9$, —C(=O)R$_9$, —C(=O)OR$_9$, or —SR$_9$, wherein the alkyl, cycloalkyl, heteroaryl, heterocyclyl may be optionally substituted with one or more R$_4$'s;

$R_3$ is halo, cyano, alkyl, cycloalkyl, heteroaryl, heterocyclyl, —NR$_9$C(=O)R$_9$, —NR$_9$C(=O)OR$_9$, —NR$_9$C(=O)NR$_9$R$_9$, —OC(=O)NR$_9$R$_9$, —C(=O)NR$_9$R$_9$, —NR$_9$R$_9$, —C(=O)R$_9$, —C(=O)OR$_9$, or —SR$_9$, wherein the alkyl, cycloalkyl, heteroaryl, heterocyclyl may be optionally substituted with one or more R$_4$'s; or $R_2$ and $R_3$ are taken together with the carbon atoms to which each is attached to form a 4- to 15-membered mono-, bi- or tricyclic ring, wherein said ring may be optionally substituted with one or more R$_4$'s;

$R_4$, at each occurrence, is independently selected from alkyl, aryl, alkenyl, alkynyl, cycloalkyl, heteroaryl, heterocyclyl, halo, =O, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ or —NR$_9$S(O$_2$)R$_8$, wherein the alkyl, aryl, alkenyl, alkynyl, cycloalkyl, heteroaryl or heterocyclyl may be optionally substituted with one or more R$_5$'s;

$R_5$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ or —NR$_9$S(O$_2$)R$_8$;

$R_8$, at each occurrence, is independently alkyl or aryl;

$R_9$, at each occurrence, is independently hydrogen, alkyl, alkoxy, cycloalkyl, aryl, arylalkyl, heteroaryl, heteroarylalkyl, heterocyclyl or heterocyclylalkyl, wherein the heteroaryl, heteroarylalkyl, heterocyclyl or heterocyclylalkyl contain 1-4 heteroatoms selected from N, O, and S;

$R_{9'}$, at each occurrence, is independently alkyl, alkoxy, cycloalkyl, aryl, arylalkyl, heteroaryl, heteroarylalkyl, heterocyclyl or heterocyclylalkyl, wherein the heteroaryl, heteroarylalkyl, heterocyclyl or heterocyclylalkyl contain 1-4 heteroatoms selected from N, O, and S;

$R_{10}$, at each occurrence, is independently selected from alkyl, alkenyl, alkynyl, aryl, arylalkyl, heterocyclyl or heterocyclylalkyl, wherein the heterocyclyl and heterocyclylalkyl contain 1-4 heteroatoms selected from N, O, and S; and $R_{14}$, at each occurrence, is independently selected from hydrogen, alkyl, cycloalkyl or aryl.

7. A compound of formula (I)

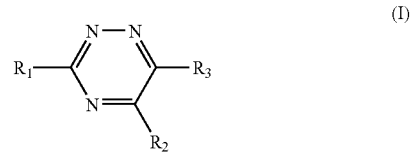

and an enantiomer, diastereomer, and salt thereof wherein:

$R_1$ is adamantyl, a 3-membered cycloalkyl or an 8- to 15-membered cycloalkyl, other than adamantyl, all of which may be optionally substituted with one or more R$_4$'s; provided that: (i) when R$_1$ is a 3- membered cycloalkyl, R$_4$ is not an optionally substituted indazolyl; and (ii) when R$_1$ is a 3- membered cycloalkyl and R$_4$ is halo, R$_2$ and Rhd 3, together with the carbon atoms to which each is attached, do not form a substituted phenyl or pyridyl ring;

$R_2$ is halo, alkyl, cycloalkyl, heteroaryl, heterocyclyl, —NR$_9$C(=O)R$_9$, —NR$_9$C(=O)OR$_9$, —NR$_9$C(=O)NR$_9$R$_9$, —OC(=O)NR$_9$R$_9$, —C(=O)NR$_9$R$_9$, —C(=O)R$_9$, or —C(=O)OR$_9$, wherein the alkyl, cycloalkyl, heteroaryl or heterocyclyl may be optionally substituted with one or more R$_4$'s; provided that R$_2$ cannot be a 5- or 6-membered substituted heteroaryl;

$R_3$ is halo, alkyl, cycloalkyl, heteroaryl, heterocyclyl, —NR$_9$C(=O)R$_9$, —NR$_9$C(=O)OR$_9$, —NR$_9$C(=O)NR$_9$R$_9$, —OC(=O)NR$_9$R$_9$, —C(=O)NR$_9$R$_9$, —NR$_9$R$_9$, —C(=O)R$_9$, or —C(=O)OR$_9$, wherein the alkyl, cycloalkyl, heteroaryl or heterocyclyl may be optionally substituted with one or more R$_4$'s; provided that R$_3$ cannot be a 6-membered substituted heteroaryl or $R_2$ and $R_3$ are taken together with the carbon atoms to which each is attached to form a 4- to 15-membered mono-, bi- or tricyclic ring, wherein said ring may be optionally substituted with one or more R$_4$'s; provided that said ring cannot be a pyrimidinedionyl ring;

$R_4$, at each occurrence, is independently selected from alkyl, aryl, cycloalkyl, heteroaryl, heterocyclyl, halo, =O, —NH$_2$, —CN, —NO$_2$, —C(=O)OH, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —S(=O)R$_{10}$, —S(O)$_2$R$_{10}$, —NR$_9$C(=O)OR$_8$, or —NR$_9$S(O$_2$)R$_8$, wherein the alkyl, cycloalkyl, heteroaryl, or heterocyclyl may be optionally substituted with one or more R$_5$'s;

$R_5$, at each occurrence, is independently selected from alkyl, haloalkyl, aryl, cycloalkyl, heteroaryl, heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —S(=O)R$_{10}$, —S(O)$_2$R$_{10}$, —NR$_9$C(=O)OR$_8$ or —NR$_9$S(O$_2$)R$_8$;

$R_8$, at each occurrence, is independently alkyl or aryl;

$R_9$, at each occurrence, is independently hydrogen, alkyl, alkoxy, cycloalkyl, aryl, heteroaryl or heterocyclyl, wherein the heteroaryl or heterocyclyl contain 1-4 heteroatoms selected from N, O, and S; and $R_{10}$, at each occurrence, is independently selected from alkyl, aryl or heterocyclyl, wherein the heterocyclyl contains 1-4 heteroatoms selected from N, O, and S.

8. The compound of claim 7, wherein:

$R_1$ is adamantyl, a 3-membered cycloalkyl or an 8- to 15-membered cycloalkyl, other than adamantyl, all of which may be optionally substituted with one or more $R_4$'s;

$R_2$ is alkyl, cycloalkyl, heteroaryl, heterocyclyl, —$NR_9C(=O)R_9$, —$NR_9C(=O)OR_{9'}$, —$NR_9C(=O)NR_9R_9$, —$OC(=O)NR_9R_9$, —$C(=O)NR_9R_9$, —$C(=O)R_9$, or —$C(=O)OR_9$, wherein the alkyl, cycloalkyl, heteroaryl or heterocyclyl may be optionally substituted with one or more $R_4$'s;

$R_3$ is alkyl, cycloalkyl, heteroaryl, heterocyclyl, —$NR_9C(=O)R_9$, —$NR_9C(=O)OR_{9'}$, —$NR_9C(=O)NR_9R_9$, —$OC(=O)NR_9R_9$, —$C(=O)NR_9R_9$, —$NR_9R_9$, —$C(=O)R_9$, or —$C(=O)OR_9$, or —$OR_9$, wherein the alkyl, cycloalkyl, heteroaryl or heterocyclyl may be optionally substituted with one or more $R_4$'s; or $R_2$ and $R_3$ are taken together with the carbon atoms to which each is attached to form a 4- to 15-membered mono-, bi- or tricylic ring, wherein said ring may be optionally substituted with one or more $R_4$'s;

$R_4$, at each occurrence, is independently selected from alkyl, aryl, cycloalkyl, heteroaryl, heterocyclyl, halo, —$NH_2$, —CN, —$NO_2$, —$C(=O)OH$, —$C(=O)OR_{10}$, —$OCF_3$, —$OR_{10}$, —OH, —SH, —$SR_{10}$, —$C(=O)NR_9R_9$, —$NR_9R_9$, —$S(O)_2NR_9R_9$, —$NR_9S(O)_2CF_3$, —$C(=O)NR_9S(O)_2R_9$, —$S(O)_2NR_9C(=O)OR_9$, —$S(O)_2NR_9C(=O)NR_9R_9$, —$C(=O)NR_9S(O)_2CF_3$, —$C(=O)R_{10}$, —$NR_9C(=O)H$, —$NR_9C(=O)R_{10}$, —$OC(=O)R_{10}$, —$OC(=O)NR_9R_9$, —$S(=O)R_{10}$ or —$S(O)_2R_{10}$, wherein the alkyl, aryl, cycloalkyl, heteroaryl or heterocyclyl may be optionally substituted with one or more $R_5$'s;

$R_5$, at each occurrence, is independently selected from alkyl, haloalkyl, aryl, cycloalkyl, heteroaryl, heterocyclyl, halo, —$NH_2$, —CN, —$NO_2$, —$C(=O)OH$, —$C(=O)OR_{10}$, —$OCF_3$, —$OR_{10}$, —OH, —SH, —$SR_{10}$, —$C(=O)NR_9R_9$, —$NR_9R_9$, —$S(O)_2NR_9R_9$, —$NR_9S(O)_2CF_3$, —$C(=O)NR_9S(O)_2R_9$, —$S(O)_2NR_9C(=O)OR_9$, —$S(O)_2NR_9C(=O)NR_9R_9$, —$C(=O)NR_9S(O)_2CF_3$, —$C(=O)R_{10}$, —$NR_9C(=O)H$, —$NR_9C(=O)R_{10}$, —$OC(=O)R_{10}$, —$S(=O)R_{10}$ or —$S(O)_2R_{10}$;

$R_9$, at each occurrence, is independently hydrogen, alkyl, cycloalkyl, aryl, heteroaryl or heterocyclyl, wherein the heteroaryl or heterocyclyl contain 1-4 heteroatoms selected from N, O, and S; and $R_{10}$, at each occurrence, is independently selected from alkyl, aryl or heterocyclyl, wherein the heterocyclyl contains 1-4 heteroatoms selected from N, O, and S.

9. The compound of claim 1, wherein:

$R_1$ is a 4- to 7-membered cycloalkyl or heterocyclyl, other than heteroaryl, all of which may be optionally substituted with one or more $R_4$'s;

$R_2$ is halo, cyano, alkyl, alkenyl, alkynyl, cycloalkyl, heteroaryl, heterocyclyl, —$NR_9C(=O)OR_{9'}$, —$NR_9C(=O)NR_9R_9$, —$C(=O)R_9$, —$SR_9$ or —$SO_2R_{9'}$, wherein the alkyl, alkenyl, alkynyl, cycloalkyl, heteroaryl or heterocyclyl may be optionally substituted with one or more $R_4$'s;

$R_3$ is halo, cyano, alkyl, alkenyl, alkynyl, cycloalkyl, heteroaryl, heterocyclyl, —$NR_9C(=O)R_9$, —$NR_9C(=O)OR_{9'}$, —$NR_9C(=O)NR_9R_9$, —$OC(=O)NR_9R_9$, —$C(=O)NR_9R_9$, —$NR_9R_9$, —$C(=O)R_9$, —$C(=O)OR_9$, —$SR_9$, —$SO_2R_{9'}$, —$SO_2NR_9R_9$, nitro, —$OP(=O)(OR_9)_2$ or —$NHSO_2R_{9'}$, wherein the alkyl, alkenyl, alkynyl, cycloalkyl, heteroaryl or heterocyclyl may be optionally substituted with one or more $R_4$'s; or $R_2$ and $R_3$ are taken together with the carbon atoms to which each is attached to form a 4- to 15-membered mono-, bi- or tricylic ring, wherein said ring may be optionally substituted with one or more $R_4$'s; or $R_2$ and $R_3$ are taken together with the carbon atoms to which each is attached to form a 4- to 15-membered mono-, bi- or tricylic heterocyclyl ring wherein the heterocyclyl ring contains 1-4 heteroatoms selected from N, O, and S, and said ring may be optionally substituted with one or more $R_4$'s;

$R_4$, at each occurrence, is independently selected from alkyl, aryl, alkenyl, alkynyl, cycloalkyl, heteroaryl, heterocyclyl, halo, =O, —$NH_2$, —CN, —$NO_2$, —$C(=O)OH$, —$C(=O)OR_{10}$, —$OCF_3$, —$OR_{10}$, —OH, —SH, —$SR_{10}$, —$S(O)_3H$, —$P(O)_3H_2$, —$C(=O)NR_9R_9$, —$NR_9R_9$, —$S(O)_2NR_9R_9$, —$NR_9S(O)_2CF_3$, —$C(=O)NR_9S(O)_2R_9$, —$S(O)_2NR_9C(=O)OR_9$, —$S(O)_2NR_9C(=O)NR_9R_9$, —$C(=O)NR_9S(O)_2CF_3$, —$C(=O)R_{10}$, —$NR_9C(=O)H$, —$NR_9C(=O)R_{10}$, —$OC(=O)R_{10}$, —$OC(=O)NR_9R_9$, —$C(=NR_{14})NR_9R_9$, —$NHC(=NR_{14})NR_{14}R_{14}$, —$S(=O)R_{10}$, —$S(O)_2R_{10}$, —$NR_9C(=O)OR_8$ or —$NR_9S(O_2)R_8$, wherein the alkyl, aryl, alkenyl, alkynyl, cycloalkyl, heteroaryl or heterocyclyl may be optionally substituted with one or more $R_5$'s;

$R_5$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —$C(=O)OH$, —$C(=O)OR_{10}$, —$OCF_3$, —$OR_{10}$, —OH, —SH, —$SR_{10}$, —$S(O)_3H$, —$P(O)_3H_2$, —$C(=O)NR_9R_9$, —$NR_9R_9$, —$S(O)_2NR_9R_9$, —$NR_9S(O)_2CF_3$, —$C(=O)NR_9S(O)_2R_9$, —$S(O)_2NR_9C(=O)OR_9$, —$S(O)_2NR_9C(=O)NR_9R_9$, —$C(=O)NR_9S(O)_2CF_3$, —$C(=O)R_{10}$, —$NR_9C(=O)H$, —$NR_9C(=O)R_{10}$, —$OC(=O)R_{10}$, —$C(=NR_{14})NR_9R_9$, —$NHC(=NR_{14})NR_{14}R_{14}$, —$S(=O)R_{10}$, —$S(O)_2R_{10}$, —$NR_9C(=O)OR_8$ or —$NR_9S(O_2)R_8$;

$R_8$, at each occurrence, is independently alkyl or aryl;

$R_9$, at each occurrence, is independently hydrogen, alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S;

$R_{9'}$, at each occurrence, is independently alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —$C(=O)OH$, —$C(=O)OR_{14}$, —$OCF_3$, —$OR_{14}$, —OH, —SH, —$SR_{14}$, —$S(O)_3H$, —$P(O)_3H_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl;

R$_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 R$_{10a}$, and the heterocyclyl and heterocyclylalkyl contain 1-4 heteroatoms selected from N, O, and S;

R$_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl; and R$_{14}$, at each occurrence, is independently selected from hydrogen, alkyl, cycloalkyl or aryl.

10. The compound of claim 1, wherein:

R$_1$ is a 4- to 7-membered cycloalkyl or heterocyclyl, other than heteroaryl, all of which may be optionally substituted with one or more R$_4$'s;

R$_2$ is halo, cyano, alkyl, alkenyl, alkynyl, cycloalkyl, heteroaryl, heterocyclyl, —NR$_9$C(=O)NR$_9$R$_9$, —C(=O)R$_9$, —SR$_9$ or —SO$_2$R$_9$, or wherein the alkyl, alkenyl, alkynyl, cycloalkyl, heteroaryl or heterocyclyl may be optionally substituted with one or more R$_4$'s;

R$_3$ is halo, cyano, alkyl, cycloalkyl, heteroaryl, heterocyclyl, —NR$_9$C(=O)R$_9$, —NR$_9$C(=O)OR$_{9'}$, —NR$_9$C(=O)NR$_9$R$_9$, —OC(=O)NR$_9$R$_9$, —C(=O)NR$_9$R$_9$, —NR$_9$R$_9$, —C(=O)R$_9$, —C(=O)OR$_9$, —SR$_9$, —SO$_2$R$_{9'}$, —SO$_2$NR$_9$R$_9$, nitro, —OP(=O)(OR$_9$)$_2$ or —NHSO$_2$R$_{9'}$, wherein the alkyl, cycloalkyl, heteroaryl or heterocyclyl may be optionally substituted with one or more R$_4$'s; or R$_2$ and R$_3$ are taken together with the carbon atoms to which each is attached to form a 4- to 15-membered mono-, bi- or tricylic ring, wherein said ring may be optionally substituted with one or more R$_4$'s;

R$_4$, at each occurrence, is independently selected from alkyl, aryl, alkenyl, alkynyl, cycloalkyl, heteroaryl, heterocyclyl, halo, =O, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ or —NR$_9$S(O$_2$)R$_8$, wherein the alkyl, aryl, alkenyl, alkynyl, cycloalkyl, heteroaryl or heterocyclyl may be optionally substituted with one or more R$_5$'s;

R$_5$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ or —NR$_9$S(O$_2$)R$_8$;

R$_8$, at each occurrence, is independently alkyl or aryl;

R$_9$, at each occurrence, is independently hydrogen, alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S;

R$_{9'}$, at each occurrence, is independently alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S;

R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl;

R$_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 R$_{10a}$, and the heterocyclyl and heterocyclylalkyl contain 1-4 heteroatoms selected from N, O, and S;

R$_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl; and R$_{14}$, at each occurrence, is independently selected from hydrogen, alkyl, cycloalkyl or aryl.

11. The compound of claim 1, wherein:

$R_1$ is a 4- to 7-membered cycloalkyl or heterocyclyl, other than heteroaryl, all of which may be optionally substituted with one or more $R_4$'s;

$R_2$ is halo, cyano, alkyl, alkenyl, alkynyl, cycloalkyl, heteroaryl, heterocyclyl, —C(=O)$R_9$, —S$R_9$ or —SO$_2R_{9'}$, wherein the alkyl, alkenyl, alkynyl, cycloalkyl, heteroaryl or heterocyclyl may be optionally substituted with one or more $R_4$'s;

$R_3$ is halo, cyano, alkyl, cycloalkyl, heteroaryl, heterocyclyl, —N$R_9$C(=O)$R_9$, —N$R_9$C(=O)O$R_{9'}$, —N$R_9$C(=O)N$R_9R_9$, —OC(=O)N$R_9R_9$, —C(=O)N$R_9R_9$, —N$R_9R_9$, —C(=O)$R_9$, —C(=O)O$R_9$, —S$R_9$ or nitro, wherein the alkyl, cycloalkyl, heteroaryl or heterocyclyl may be optionally substituted with one or more $R_4$'s;

$R_4$, at each occurrence, is independently selected from alkyl, aryl, alkenyl, alkynyl, cycloalkyl, heteroaryl, heterocyclyl, halo, =O, —NH$_2$, —CN, —NO$_2$, —C(=O)OH, —C(=O)O$R_{10}$, —OCF$_3$, —O$R_{10}$, —OH, —SH, —S$R_{10}$, —S(O)$_3$H, —P(O)$_3$H$_2$, —C(=O)N$R_9R_9$, —N$R_9R_9$, —S(O)$_2$N$R_9R_9$, —N$R_9$S(O)$_2$CF$_3$, —C(=O)N$R_9$S(O)$_2R_9$, —S(O)$_2$N$R_9$C(=O)O$R_9$, —S(O)$_2$N$R_9$C(=O)N$R_9R_9$, —C(=O)N$R_9$S(O)$_2$CF$_3$, —C(=O)$R_{10}$, —N$R_9$C(=O)H, —N$R_9$C(=O)$R_{10}$, —OC(=O)$R_{10}$, —OC(=O)N$R_9R_9$, —C(=N$R_{14}$)N$R_9R_9$, —NHC(=N$R_{14}$)N$R_{14}R_{14}$, —S(=O)$R_{10}$, —S(O)$_2R_{10}$, —N$R_9$C(=O)O$R_8$ or —N$R_9$S(O$_2$)$R_8$, wherein the alkyl, aryl, alkenyl, alkynyl, cycloalkyl, heteroaryl or heterocyclyl may be optionally substituted with one or more $R_5$'s;

$R_5$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)O$R_{10}$, —OCF$_3$, —O$R_{10}$, —OH, —SH, —S$R_{10}$, —S(O)$_3$H, —P(O)$_3$H$_2$, —C(=O)N$R_9R_9$, —N$R_9R_9$, —S(O)$_2$N$R_9R_9$, —N$R_9$S(O)$_2$CF$_3$, —C(=O)N$R_9$S(O)$_2R_9$, —S(O)$_2$N$R_9$C(=O)O$R_9$, —S(O)$_2$N$R_9$C(=O)N$R_9R_9$, —C(=O)N$R_9$S(O)$_2$CF$_3$, —C(=O)$R_{10}$, —N$R_9$C(=O)H, —N$R_9$C(=O)$R_{10}$, —OC(=O)$R_{10}$, —C(=N$R_{14}$)N$R_9R_9$, —NHC(=N$R_{14}$)N$R_{14}R_{14}$, —S(=O)$R_{10}$, —S(O)$_2R_{10}$, —N$R_9$C(=O)O$R_8$ or —N$R_9$S(O$_2$)$R_8$;

$R_8$, at each occurrence, is independently alkyl or aryl;

$R_9$, at each occurrence, is independently hydrogen, alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S;

$R_{9'}$, at each occurrence, is independently alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)O$R_{14}$, —OCF$_3$, —O$R_{14}$, —OH, —SH, —S$R_{14}$, —S(O)$_3$H, —P(O)$_3$H$_2$, —C(=O)N$R_{14}R_{14}$, —N$R_{14}R_{14}$, —S(O)$_2$N$R_{14}R_{14}$, —N$R_{14}$S(O)$_2$CF$_3$, —C(=O)N$R_{14}$S(O)$_2R_{10}$, —S(O)$_2$N$R_{14}$C(=O)O$R_{10}$, —S(O)$_2$N$R_{14}$C(=O)N$R_{14}R_{14}$, —C(=O)N$R_{14}$S(O)$_2$CF$_3$, —C(=O)$R_{14}$, —N$R_{14}$C(=O)H, —N$R_{14}$C(=O)$R_{14}$, —OC(=O)$R_{14}$, —C(=N$R_{14}$)N$R_{14}R_{14}$, —NHC(=N$R_{14}$)N$R_{14}R_{14}$, —S(=O)$R_{14}$, —S(O)$_2R_{14}$, —N$R_{14}$C(=O)O$R_8$, —N$R_{14}$S(O$_2$)$R_8$ or arylalkyl;

$R_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)O$R_{14}$, —OCF$_3$, —O$R_{14}$, —OH, —SH, —S$R_{14}$, —S(O)$_3$H, —P(O)$_3$H$_2$, —C(=O)N$R_{14}R_{14}$, —N$R_{14}R_{14}$, —S(O)$_2$N$R_{14}R_{14}$, —N$R_{14}$S(O)$_2$CF$_3$, —C(=O)N$R_{14}$S(O)$_2R_9$, —S(O)$_2$N$R_{14}$C(=O)O$R_9$, —S(O)$_2$N$R_{14}$C(=O)N$R_{14}R_{14}$, —C(=O)N$R_{14}$S(O)$_2$CF$_3$, —C(=O)$R_{14}$, —N$R_{14}$C(=O)H, —N$R_{14}$C(=O)$R_{14}$, —OC(=O)$R_{14}$, —C(=N$R_{14}$)N$R_{14}R_{14}$, —NHC(=N$R_{14}$)N$R_{14}R_{14}$, —S(=O)$R_{14}$, —S(O)$_2R_{14}$, —N$R_{14}$C(=O)O$R_8$, —N$R_{14}$S(O$_2$)$R_8$ or arylalkyl; and $R_{14}$, at each occurrence, is independently selected from hydrogen, alkyl, cycloalkyl or aryl.

12. The compound of claim 1, wherein:

$R_1$ is a 4- to 7-membered cycloalkyl or heterocyclyl, other than heteroaryl, all of which may be optionally substituted with one or more $R_4$'s;

$R_2$ is halo, cyano, alkyl, alkenyl, alkynyl, cycloalkyl, heteroaryl, heterocyclyl, —S$R_9$ or —SO$_2R_{9'}$, wherein the alkyl, alkenyl, alkynyl, cycloalkyl, heteroaryl, heterocyclyl may be optionally substituted with one or more $R_4$'s;

$R_3$ is halo, cyano, alkyl, cycloalkyl, heteroaryl, heterocyclyl, —N$R_9$C(=O)$R_9$, —N$R_9$C(=O)O$R_{9'}$, —N$R_9$C(=O)N$R_9R_9$, —OC(=O)N$R_9R_9$, —C(=O)N$R_9R_9$, —N$R_9R_9$, —C(=O)$R_9$, —C(=O)O$R_9$, —S$R_9$ or nitro, wherein the alkyl, cycloalkyl, heteroaryl or heterocyclyl may be optionally substituted with one or more $R_4$'s;

$R_4$, at each occurrence, is independently selected from alkyl, aryl, alkenyl, alkynyl, cycloalkyl, heteroaryl, heterocyclyl, halo, =O, —NH$_2$, —CN, —NO$_2$, —C(=O)OH, —C(=O)O$R_{10}$, —OCF$_3$, —O$R_{10}$, —OH, —SH, —S$R_{10}$, —S(O)$_3$H, —P(O)$_3$H$_2$, —C(=O)N$R_9R_9$, —N$R_9R_9$, —S(O)$_2$N$R_9R_9$, —N$R_9$S(O)$_2$CF$_3$, —C(=O)N$R_9$S(O)$_2R_9$, —S(O)$_2$N$R_9$C(=O)O$R_9$, —S(O)$_2$N$R_9$C(=O)N$R_9R_9$, —C(=O)N$R_9$S(O)$_2$CF$_3$, —C(=O)$R_{10}$, —N$R_9$C(=O)H, —N$R_9$C(=O)$R_{10}$, —OC(=O)$R_{10}$, —OC(=O)N$R_9R_9$, —C(=N$R_{14}$)N$R_9R_9$, —NHC(=N$R_{14}$)N$R_{14}R_{14}$, —S(=O)$R_{10}$, —S(O)$_2R_{10}$, —N$R_9$C(=O)O$R_8$ or —N$R_9$S(O$_2$)$R_8$, wherein the alkyl, aryl, alkenyl, alkynyl, cycloalkyl, heteroaryl or heterocyclyl may be optionally substituted with one or more $R_5$'s;

$R_5$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)O$R_{10}$, —OCF$_3$, —O$R_{10}$, —OH, —SH, —S$R_{10}$, —S(O)$_3$H, —P(O)$_3$H$_2$, —C(=O)N$R_9R_9$, —N$R_9R_9$, —S(O)$_2$N$R_9R_9$, —N$R_9$S(O)$_2$CF$_3$, —C(=O)N$R_9$S(O)$_2R_9$, —S(O)$_2$N$R_9$C(=O)

$OR_9$, $-S(O)_2NR_9C(=O)NR_9R_9$, $-C(=O)$ $NR_9S(O)_2CF_3$, $-C(=O)R_{10}$, $-NR_9C(=O)H$, $-NR_9C(=O)R_{10}$, $-OC(=O)R_{10}$, $-C(=NR_{14})$ $NR_9R_9$, $-NHC(=NR_{14})NR_{14}R_{14}$, $-S(=O)R_{10}$, $-S(O)_2R_{10}$, $-NR_9C(=O)OR_8$ or $-NR_9S(O_2)R_8$;

$R_8$, at each occurrence, is independently alkyl or aryl;

$R_9$, at each occurrence, is independently hydrogen, alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S;

$R_{9'}$, at each occurrence, is independently alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_{10}$, $-S(O)_2NR_{14}C(=O)OR_{10}$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})NR_{14}R_{14}$, $-NHC(=NR_{14})NR_{14}R_{14}$, $-S(=O)R_{14}$, $-S(O)_2R_{14}$, $-NR_{14}C(=O)OR_8$, $-NR_{14}S(O_2)R_8$ or arylalkyl;

$R_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_9$, $-S(O)_2NR_{14}C(=O)OR_9$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})NR_{14}R_{14}$, $-NHC(=NR_{14})NR_{14}R_{14}$, $-S(=O)R_{14}$, $-S(O)_2R_{14}$, $-NR_{14}C(=O)OR_8$, $-NR_{14}S(O_2)R_8$ or arylalkyl; and $R_{14}$, at each occurrence, is independently selected from hydrogen, alkyl, cycloalkyl or aryl.

13. The compound of claim 1, wherein:

$R_1$ is a 4- to 7-membered cycloalkyl or heterocyclyl, other than heteroaryl, all of which may be optionally substituted with one or more $R_4$'s;

$R_2$ is halo, cyano, alkyl, alkenyl, alkynyl, cycloalkyl, heteroaryl, heterocyclyl or $-SO_2R_{9'}$, wherein the alkyl, alkenyl, alkynyl, cycloalkyl, heteroaryl or heterocyclyl may be optionally substituted with one or more $R_4$'s;

$R_3$ is halo, cyano, alkyl, cycloalkyl, heteroaryl, heterocyclyl, $-NR_9C(=O)R_9$, $-NR_9C(=O)OR_{9'}$, $-NR_9C(=O)NR_9R_9$, $-OC(=O)NR_9R_9$, $-C(=O)NR_9R_9$, $-NR_9R_9$, $-C(=O)R_9$, $-C(=O)OR_9$, or $-SR_9$, wherein the alkyl, cycloalkyl, heteroaryl or heterocyclyl may be optionally substituted with one or more $R_4$'s;

$R_4$, at each occurrence, is independently selected from alkyl, aryl, alkenyl, alkynyl, cycloalkyl, heteroaryl, heterocyclyl, halo, $=O$, $-NH_2$, $-CN$, $-NO_2$, $-C(=O)$ OH, $-C(=O)OR_{10}$, $-OCF_3$, $-OR_{10}$, $-OH$, $-SH$, $-SR_{10}$, $-S(O)_3H$, $-P(O)_3H_2$, $-C(=O)NR_9R_9$, $-NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)H$, $-NR_9C(=O)R_{10}$, $-OC(=O)R_{10}$, $-OC(=O)NR_9R_9$, $-C(=NR_{14})NR_9R_9$, $-NHC(=NR_{14})NR_{14}R_{14}$, $-S(=O)R_{10}$, $-S(O)_2R_{10}$, $-NR_9C(=O)OR_8$ or $-NR_9S(O_2)R_8$, wherein the alkyl, aryl, alkenyl, alkynyl, cycloalkyl, heteroaryl or heterocyclyl may be optionally substituted with one or more $R_5$'s;

$R_5$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{10}$, $-OCF_3$, $-OR_{10}$, $-OH$, $-SH$, $-SR_{10}$, $-S(O)_3H$, $-P(O)_3H_2$, $-C(=O)NR_9R_9$, $-NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)H$, $-NR_9C(=O)R_{10}$, $-OC(=O)R_{10}$, $-C(=NR_{14})NR_9R_9$, $-NHC(=NR_{14})NR_{14}R_{14}$, $-S(=O)R_{10}$, $-S(O)_2R_{10}$, $-NR_9C(=O)OR_8$ or $-NR_9S(O_2)R_8$;

$R_8$, at each occurrence, is independently alkyl or aryl;

$R_9$, at each occurrence, is independently hydrogen, alkyl, alkoxy, cycloalkyl, aryl, arylalkyl, heteroaryl, heteroarylalkyl, heterocyclyl or heterocyclylalkyl, wherein the heteroaryl, heteroarylalkyl, heterocyclyl or heterocyclylalkyl contain 1-4 heteroatoms selected from N, O, and S;

$R_{9'}$, at each occurrence, is independently alkyl, alkoxy, cycloalkyl, aryl, arylalkyl, heteroaryl, heteroarylalkyl, heterocyclyl or heterocyclylalkyl, wherein the heteroaryl, heteroarylalkyl, heterocyclyl or heterocyclylalkyl contain 1-4 heteroatoms selected from N, O, and S;

$R_{10}$, at each occurrence, is independently selected from alkyl, alkenyl, alkynyl, aryl, arylalkyl, heterocyclyl or heterocyclylalkyl, wherein the heterocyclyl and heterocyclylalkyl contain 1-4 heteroatoms selected from N, O, and S; and $R_{14}$, at each occurrence, is independently selected from hydrogen, alkyl, cycloalkyl or aryl.

14. The compound of claim 1, wherein:

$R_1$ is a 4- to 7-membered cycloalkyl or heterocyclyl, other than heteroaryl, all of which may be optionally substituted with one or more $R_4$'s;

$R_2$ is halo, cyano, alkyl, alkenyl, alkynyl, cycloalkyl, heteroaryl, or heterocyclyl, wherein the alkyl, alkenyl, alkynyl, cycloalkyl, heteroaryl or heterocyclyl may be optionally substituted with one or more $R_4$'s;

$R_3$ is halo, alkyl, cycloalkyl, heteroaryl, heterocyclyl, $-NR_9C(=O)R_9$, $-NR_9C(=O)OR_{9'}$, $-NR_9C(=O)NR_9R_9$, $-OC(=O)NR_9R_9$, $-C(=O)NR_9R_9$, $-NR_9R_9$, $-C(=O)R_9$, or $-C(=O)OR_9$, wherein the alkyl, cycloalkyl, aryl, heteroaryl or heterocyclyl may be optionally substituted with one or more $R_4$'s;

R₄, at each occurrence, is independently selected from alkyl, aryl, cycloalkyl, heteroaryl, heterocyclyl, halo, =O, —NH₂, —CN, —NO₂, —C(=O)OH, —C(=O)OR₁₀, —OCF₃, —OR₁₀, —OH, —SH, —SR₁₀, —C(=O)NR₉R₉, —NR₉R₉, —S(O)₂NR₉R₉, —NR₉S(O)₂CF₃, —C(=O)NR₉S(O)₂R₉, —S(O)₂NR₉C(=O)OR₉, —S(O)₂NR₉C(=O)NR₉R₉, —C(=O)NR₉S(O)₂CF₃, —C(=O)R₁₀, —NR₉C(=O)H, —NR₉C(=O)R₁₀, —OC(=O)R₁₀, —OC(=O)NR₉R₉, —S(=O)R₁₀, —S(O)₂R₁₀, —NR₉C(=O)OR₈, or —NR₉S(O₂)R₈, wherein the alkyl, aryl, cycloalkyl, heteroaryl, or heterocyclyl may be optionally substituted with one or more R₅'s;

R₅, at each occurrence, is independently selected from alkyl, haloalkyl, aryl, cycloalkyl, heteroaryl, heterocyclyl, halo, —NH₂, —CN, —NO₂, —C(=O)OH, —C(=O)OR₁₀, —OCF₃, —OR₁₀, —OH, —SH, —SR₁₀, —C(=O)NR₉R₉, —NR₉R₉, —S(O)₂NR₉R₉, —NR₉S(O)₂CF₃, —C(=O)NR₉S(O)₂R₉, —S(O)₂NR₉C(=O)OR₉, —S(O)₂NR₉C(=O)NR₉R₉, —C(=O)NR₉S(O)₂CF₃, —C(=O)R₁₀, —NR₉C(=O)H, —NR₉C(=O)R₁₀, —OC(=O)R₁₀, —S(=O)R₁₀, —S(O)₂R₁₀, —NR₉C(=O)OR₈ or —NR₉S(O₂)R₈;

R₈, at each occurrence, is independently alkyl or aryl;

R₉, at each occurrence, is independently hydrogen, alkyl, alkoxy, cycloalkyl, aryl, heteroaryl or heterocyclyl, wherein the heteroaryl or heterocyclyl contain 1-4 heteroatoms selected from N, O, and S; and R₁₀, at each occurrence, is independently selected from alkyl, aryl or heterocyclyl, wherein the heterocyclyl contains 1-4 heteroatoms selected from N, O, and S.

15. The compound of claim 1, wherein:

R₁ is a 4- to 7-membered cycloalkyl or heterocyclyl, other than heteroaryl, all of which may be optionally substituted with one or more R₄'s;

R₂ is halo, cyano, alkenyl, alkynyl, cycloalkyl, heteroaryl or heterocyclyl, wherein the alkenyl, alkynyl, cycloalkyl, heteroaryl or heterocyclyl may be optionally substituted with one or more R₄'s;

R₃ is alkyl, cycloalkyl, heteroaryl, heterocyclyl, —NR₉C(=O)R₉, —NR₉C(=O)OR₉·, —NR₉C(=O)NR₉R₉, —OC(=O)NR₉R₉, —C(=O)NR₉R₉, —NR₉R₉, —C(=O)R₉, —C(=O)OR₉, wherein the alkyl, cycloalkyl, heteroaryl or heterocyclyl may be optionally substituted with one or more R₄'s;

R₄, at each occurrence, is independently selected from alkyl, aryl, cycloalkyl, heteroaryl, heterocyclyl, halo, —NH₂, —CN, —NO₂, —C(=O)OH, —C(=O)OR₁₀, —OCF₃, —OR₁₀, —OH, —SH, —SR₁₀, —C(=O)NR₉R₉, —NR₉R₉, —S(O)₂NR₉R₉, —NR₉S(O)₂CF₃, —C(=O)NR₉S(O)₂R₉, —S(O)₂NR₉C(=O)OR₉, —S(O)₂NR₉C(=O)NR₉R₉, —C(=O)NR₉S(O)₂CF₃, —C(=O)R₁₀, —NR₉C(=O)H, —NR₉C(=O)R₁₀, —OC(=O)R₁₀, —OC(=O)NR₉R₉, —S(=O)R₁₀ or —S(O)₂R₁₀, wherein the alkyl, aryl, cycloalkyl, heteroaryl or heterocyclyl may be optionally substituted with one or more R₅'s;

R₅, at each occurrence, is independently selected from alkyl, haloalkyl, aryl, cycloalkyl, heteroaryl, heterocyclyl, halo, —NH₂, —CN, —NO₂, —C(=O)OH, —C(=O)OR₁₀, —OCF₃, —OR₁₀, —OH, —SH, —SR₁₀, —C(=O)NR₉R₉, —NR₉R₉, —S(O)₂NR₉R₉, —NR₉S(O)₂CF₃, —C(=O)NR₉S(O)₂R₉, —S(O)₂NR₉C(=O)OR₉, —S(O)₂NR₉C(=O)NR₉R₉, —C(=O)NR₉S(O)₂CF₃, —C(=O)R₁₀, —NR₉C(=O)H, —NR₉C(=O)R₁₀, —OC(=O)R₁₀, —S(=O)R₁₀ or —S(O)₂R₁₀;

R₉, at each occurrence, is independently hydrogen, alkyl, cycloalkyl, aryl, heteroaryl or heterocyclyl, wherein the heteroaryl or heterocyclyl contain 1-4 heteroatoms selected from N, O, and S; and R₁₀, at each occurrence, is independently selected from alkyl, aryl or heterocyclyl, wherein the heterocyclyl contains 1-4 heteroatoms selected from N, O, and S.

16. A pharmaceutical composition consisting of a compound of claim 1 and a pharmaceutically acceptable carrier.

17. The pharmaceutical composition consisting of a compound of claim 1, a pharmaceutically acceptable carrier and at least one additional therapeutic agent.

18. A method for treating or slowing the progression of diabeties, hyperglycemia, obesity dyslipidemia, and hypertension, which comprises administering to a mammalian patient in need of treatment a therapeutically effective amount of a compound of formula I

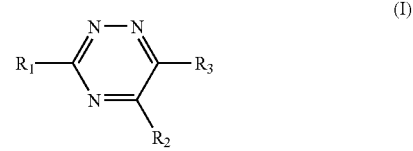

(I)

and an enantiomer, diastereomer, and salt thereof wherein:

R₁ is cycloalkyl, adamantyl or heterocyclyl, other than heteroaryl, all of which may be optionally substituted with one or more R₄'s; provided that: (i) when R₁ is heterocyclyl, the heterocyclyl does not attach to the triazine ring via a nitrogen atom; (ii) when R₁ is a 3-membered cycloalkyl, R₄ is not an optionally substituted indazolyl; and (iii) when R₁ is a 3- to 5-membered cycloalkyl and R₄ is halo, R₂ and R₃,together with the carbon atoms to which each is attached, do not form a substituted phenyl or pyridyl ring;

R₂ is hydrogen, halo, cyano, alkyl, alkenyl, alkynyl, cycloalkyl, heteroaryl, heterocyclyl, —NR₉C(=O)R₉, —NR₉C(=O)OR₉·,—NR₉C(=O)NR₉R₉, —OC(=O)NR₉R₉, —C(=O)NR₉R₉, —C(=O)R₉, —C(=O)OR₉, —SR₉, —SO₂R₉·, —SO₂NR₉R₉, nitro, —OP(=O)(OR₉)₂ or —NHSO₂R₉·, wherein the alkyl, alkenyl, alkynyl, cycloalkyl, heteroaryl or heterocyclyl may be optionally substituted with one or more R₄'s; provided that R₂ cannot be a 5- or 6-membered substituted heteroaryl;

R₃ is halo, cyano, alkyl, alkenyl, alkynyl, cycloalkyl, heteroaryl, heterocyclyl, —NR₉C(=O)R₉, —NR₉C(=O)OR₉·, —NR₉C(=O)NR₉R₉, —OC(=O)NR₉R₉, —C(=O)NR₉R₉, —NR₉R₉, —C(=O)R₉, —C(=O)OR₉, —SR₉, —SO₂R₉·, —SO₂NR₉R₉, nitro, —OP(=O)(OR₉)₂ or —NHSO₂R₉·, wherein the alkyl, alkenyl, alkynyl, cycloalkyl, heteroaryl or heterocyclyl may be optionally substituted with one or more R₄'s; provided that R₃ cannot be a 6-membered substituted heteroaryl; or R₂ and R₃ are taken together with the carbon atoms to which each is attached to form a 4- to 15-membered mono-, bi- or tricylic ring, wherein said ring may be optionally substituted with one or more R₄'s; or R₂ and R₃ are taken together with the carbon atoms to which each is attached to form a 4-to 15-membered mono-, bi- or tricylic heterocyclyl ring wherein the heterocyclyl ring contains 1-4 heteroatoms selected from N, O, and S, and said ring may be optionally substituted with one or more R$_4$'s; provided that said ring cannot be a pyrimidinedionyl ring;

R$_4$, at each occurrence, is independently selected from alkyl, aryl, alkenyl, alkynyl, cycloalkyl, heteroaryl, heterocyclyl, halo, =O, —NH$_2$, —CN,—NO$_2$, —C(=O)OH, —C(=O)OR$_{10}$, —OCF$_3$, —OR$_{10}$, —OH, —SH, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O) NR$_9$S(O)$_2$R$_9$, —S(O)$_2$NR$_9$C(=O)OR$_9$, —S(O)$_2$NR$_9$C (=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC (=NR$_{14}$)NR$_{14}$R$_{14}$, —S(=O)R$_{10}$, —S(O)$_2$R$_{10}$, —NR$_9$C(=O)OR$_8$ or —NR$_9$S(O$_2$)R$_8$, wherein the alkyl, aryl, alkenyl, alkynyl, cycloalkyl, heteroaryl or heterocyclyl may be optionally substituted with one or more R$_5$'s;

R$_5$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S (O)$_2$CF$_3$, —C(=O)NR$_9$S(O)$_2$R$_9$, —S(O)$_2$NR$_9$C(=O) OR$_9$, —S(O)$_2$NR$_9$C(=O)NR$_9$R$_9$, —C(=O) NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$) NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ or —NR$_9$S(O$_2$)R$_8$;

R$_8$, at each occurrence, is independently alkyl or aryl;

R$_9$, at each occurrence, is independently hydrogen, alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S;

R$_{9'}$, at each occurrence, is independently alkyl, alkoxy, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0- 5 R$_{9a}$, and the heteroaryl, heteroarylalkyl, heterocyclyl or heterocyclylalkyl contain 1-4 heteroatoms selected from N, O, and S;

R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(0)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O) NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O )R$_{14}$, —C(=NR$_{14}$)NR$_{14}$R$_{14}$, —NHC (=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl;

R$_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 R$_{10a}$, and the heterocyclyl and heterocyclylalkyl contain 1-4 heteroatoms selected from N, O, and S;

R$_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH $_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(O)OR$_9$, —S(O)$_2$NR$_{14}$C(=O) NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(502 O)R$_{14}$, —C(=NR$_{14}$)NR$_{14}$R$_{14}$, —NHC(=NR$_{14}$) NR$_{14}$R$_{14}$, —S(=—)R$_{14}$, —S(O)$_2$R$_{14}$, —NR$_{14}$C(=O) OR$_8$, —NR$_{14}$S(O$_2$)R$_8$ or arylalkyl; and R$_{14}$, at each occurrence, is independently selected from hydrogen, alkyl, cycloalkyl or aryl.

19. A compound having the following formula:

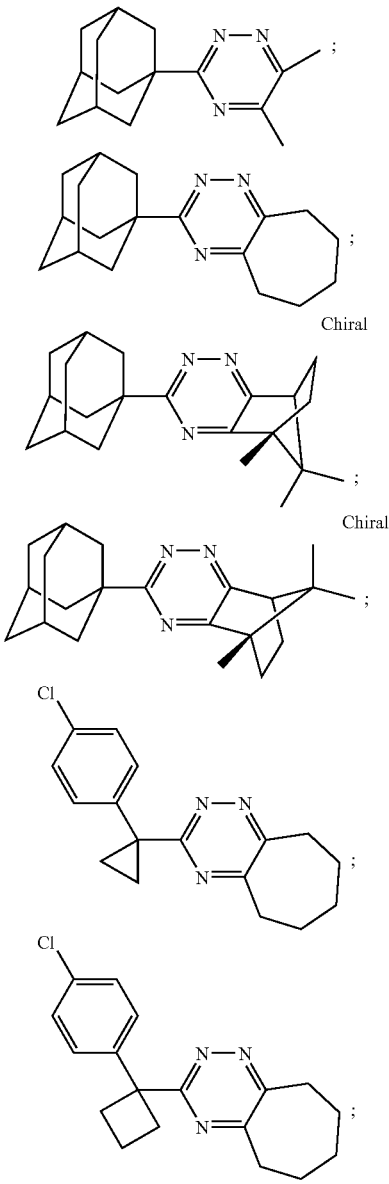

-continued
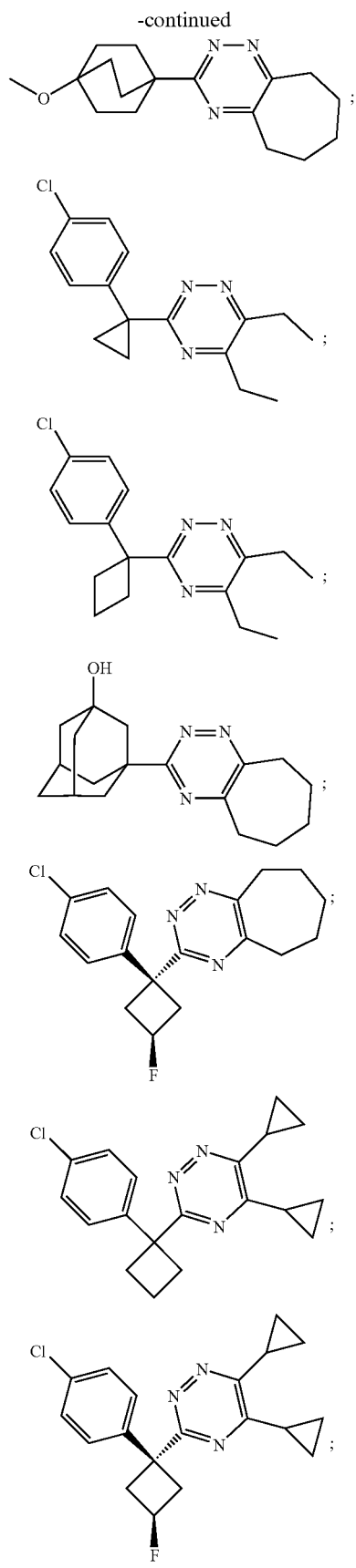
-continued
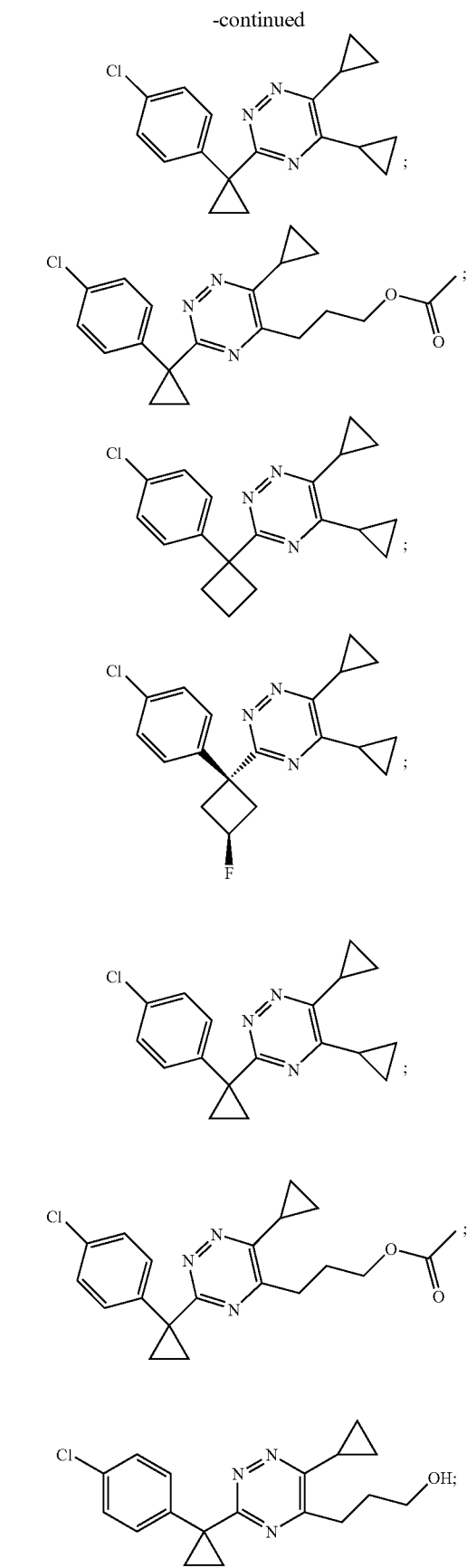

-continued

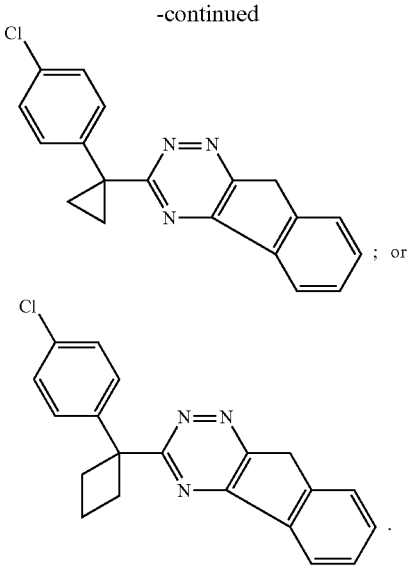
; or

20. A pharmaceutical composition consisting of a compound of claim 7 and a pharmaceutically acceptable carrier.

21. A pharmaceutical composition consistig of a compound of claim 7, a pharmaceutically acceptable carrier and at least one additional therapeutic agent.

22. A method for treating or slowing the progression of diabetes, hyperglycemia, obesity, dyslipidemia, and hypertension, which comprises administering to a mammalian patient in need of treatment a therapeutically effective amount of a compound of formula I

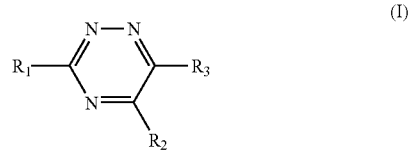
(I)

and an enantiomer, diastereomer, and salt thereof wherein:

$R_1$ is adamantyl, a 3-membered cycloalkyl or an 8- to 15-membered cycloalkyl, other than adamantyl, all of which may be optionally substituted with one or more $R_4$'s; provided that: (i) when $R_1$ is a 3-membered cycloalkyl, $T_4$ is not an optionally substituted indazolyl; and (ii) when $R_1$ is a 3-membered cycloalkyl and $R_4$ is halo, $R_2$ and $R_3$, together with the carbon atoms to which each is attached, do not form a substited phenyl or pyridyl ring;

$R_2$ is halo, alkyl, cycloalkyl, heteroaryl, heterocyclyl, $-NR_9C(=O)R_9$, $-NR_9C(=O)OR_9$, $-NR_9C(=O)NR_9R_9$, $-OC(=O)NR_9R_9$, $-C(=O)NR_9R_9$, $-C(=O)R_9$, or $-C(=O)OR_9$, wherein the alkyl, cycloalkyl, heteroaryl or heterocyclyl may be optionally substituted with one or more $R_4$'s; provided that $R_2$ cannot be a 5- or 6- membered substituted heteroaryl;

$R_3$ is halo, alkyl, cycloalkyl, heteroaryl, heterocyclyl, $-NR_9C(=O)R_9$, $-NR_9C(=O)OR_9$, $-NR_9C(=O)NR_9R_9$, $-OC(=O)NR_9R_9$, $-C(=O)NR_9R_9$, $-C(=O)R_9$, or $-C(=O)OR_9$, wherein the alkyl, cycloalkyl, heteroaryl or heterocyclyl may be optionally substituted with one or more $R_4$'s; provided that $R_3$ cannot be a 6-membered substituted heteroaryl; or $R_2$ $R_3$ are taken together with the carbon atoms to which each is attached to form a 4- to 15-membered mono-, bi- or tricyclic ring, wherein said ring may be optionally substituted with one or more $R_4$'s; provided that said ring cannot be a pyrimidinedionyl ring;

$R_4$, at each occurence, is independently selected from alkyl, aryl, cycloalkyl, heteroaryl, heterocyclyl, halo, $=O$, $-NH_2$, $-CN$, $-NO_2$, $-C(=O)OH$, $-C(=O)OR_{10}$, $-OCF_3$, $-OR_{10}$, $-OH$, $-SH$, $-SR_{10}$, $-C(=O)NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)H$, $-NR_9C(=O)R_{10}$, $-OC(=O)R_{10}$, $-OC(=O)NR_9R_9$, $-S(=O)R_{10}$, $-S(O)_2R_{10}$, $-NR_9C(=O)OR_8$, or $-NR_9S(O_2)R_8$, wherein the alkyl, aryl, cycloalkyl, heteroaryl, or heterocyclyl may be optionally substituted with one or more $R_5$'s;

$R_5$, at each occurence, is independently selected from alkyl, haloalkyl, aryl, cycloalkyl, heteroaryl, heterocyclyl, halo, $-NH_2$, $-CN$, $-NO_2$, $-C(=O)OH$, $-C(=O)OR_{10}$, $-OCF_3$, $-OR_{10}$, $-OH$, $-SH$, $-SR_{10}$, $-C(=O)NR_9, R_9$, $-NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)H$, $-NR_9C(=O)R_{10}$, $-OC(=O)R_{10}$, $-S(O)_2R_{10}$, $-NR_9C(=O)OR_8$ or $-NR_9S(O_2)R_8$;

$R_8$, at each occurence, is independently alkyl or aryl;

$R_9$, at each occurence, is independently hydrogen, alkyl, alkoxy, cycloalkyl, aryl, heteroaryl or heterocyclyl, wherein the heteroaryl or heterocyclyl contain 1-4 heteroatoms selected from N, O, and S; and $R_{10}$, at each occurence, is independently selected from alykl, aryl or heterocyclyl, wherein the heterocyclyl contains 1-4 heteroatoms selected from N, O, and S.

23. A pharmaceutical composition consisting of a compound of claim 19 and a pharmaceutically acceptable carrier.

24. A pharmaceutical composition consisting of a compound of claim 19, a pharmaceutically acceptable carrier and at least one additional therapeutic agent.

25. A method for treating or slowing the progression of diabetes, hyperglycemia, obesity, dyslipidemia, and hypertension, which comprises administering to a mammalian patient in need of treatment a therapeutically effective amoung of a compound of claim 19.

* * * * *

UNITED STATES PATENT AND TRADEMARK OFFICE
CERTIFICATE OF CORRECTION

| | | |
|---|---|---|
| PATENT NO. | : 7,834,178 B2 | |
| APPLICATION NO. | : 11/679898 | |
| DATED | : November 16, 2010 | |
| INVENTOR(S) | : Jun Li et al. | |

It is certified that error appears in the above-identified patent and that said Letters Patent is hereby corrected as shown below:

On the Title Page:

Item (56) References Cited, under OTHER PUBLICATIONS:

Banker et al. reference, change "Pharmaceutices" to -- Pharmaceutics --.

The reference should read:

-- Banker, G.S. et al, "Modern Pharmaceutics, 3ed.", Marcel Dekker, New York. 1996, pp. 451 and 596.* --.

In the Claims:

Claim 1:

Column 63, line 66, change "heteroaryl,all" to -- heteroaryl, all --.

Column 64, line 53, change "heterocylclyl" to -- heterocyclyl --.

Column 64, line 56, change "5 membered" to -- 5-membered --.

Column 64, line 57, change "R₃,together" to -- R₃, together --.

Column 64, line 59, change "substitued" to -- substituted --.

Column 65, line 2, change "6- membered" to -- 6-membered --.

Column 65, line 12, change "6- membered" to -- 6-membered --.

Signed and Sealed this
Twenty-first Day of June, 2011

David J. Kappos
*Director of the United States Patent and Trademark Office*

In the Claims:

Claim 1 (continued):

Column 65, line 16, change "tricylic" to -- tricyclic --.

Column 65, line 20, change "tricylic" to -- tricyclic --.

Column 65, line 38, change "maybe" to -- may be --.

Column 66, line 63, change "tricylic" to -- tricyclic --.

Column 66, line 67, change "tricylic" to -- tricyclic --.

Claim 3:

Column 68, line 43, after "$R_4$'s;" delete "or".

Claim 7:

Column 74, line 17, change "3- membered" to -- 3-membered --.

Column 74, line 18, change "Rhd 3," to -- $R_3$, --.

Column 74, lines 34 and 35, change "heteroaryl or" to -- heteroaryl; or --.

Claim 10:

Column 77, line 38, before "wherein", delete "or".

Claim 12:

Column 80, line 36, after "heteroaryl,", insert -- or --.

Claim 14:

Column 82, line 66, after "cycloalkyl," delete "aryl,".

Claim 17:

Column 84, line 10, change "The" to -- A --.

Claim 18:

Column 84, line 15, change "diabeties" to -- diabetes --.

Column 84, line 15, change "obesity" to -- obesity, --.

Column 84, line 36, change "$R_3$,together" to -- $R_3$, together --.

Column 84, line 65, change "4-to" to -- 4- to --.

Column 85, line 46, change "0- 5" to -- 0-5 --.

Column 86, lines 13 and 14, change "—OC(502O)$R_{14}$" to -- —OC(=O)$R_{14}$ --.

Column 86, line 15, change "—S(=—)$R_{14}$" to -- —S(=O)$R_{14}$ --.

Claim 21:

Column 89, line 27, change "consistig" to -- consisting --.

Claim 22:

Column 89, line 50, change "$T_4$" to -- $R_4$ --.

Column 89, line 53, change "substited" to -- substituted --.

Column 90, line 3, change "6- membered" to -- 6-membered --.

Column 90, line 11, change "$R_2$ $R_3$" to -- $R_2$ and $R_3$ --.

Column 90, line 16, change "occurence" to -- occurrence --.

Column 90, line 29, change "occurence" to -- occurrence --.

Column 90, line 39, change "occurence" to -- occurrence --.

Column 90, line 40, change "occurence" to -- occurrence --.

Column 90, line 44, change "occurence" to -- occurrence --.

Column 90, line 45, change "alykl" to -- alkyl --.

Claim 25:

Column 90, line 56, change "amoung" to -- amount --.